(12) United States Patent
Cone et al.

(10) Patent No.: US 6,278,038 B1
(45) Date of Patent: Aug. 21, 2001

(54) MAMMALIAN MELANOCORTIN RECEPTORS AND USES

(75) Inventors: Roger D. Cone, Oregon City, OR (US); Wenbiao Chen, Newton, MA (US); Malcolm J. Low, Portland, OR (US)

(73) Assignee: Oregon Health and Science University, Portland, OR (US)

(*) Notice: Subject to any disclaimer, the term of this patent is extended or adjusted under 35 U.S.C. 154(b) by 0 days.

(21) Appl. No.: 09/097,231

(22) Filed: Jun. 12, 1998

Related U.S. Application Data

(63) Continuation-in-part of application No. 08/706,281, filed on Sep. 4, 1996, now Pat. No. 6,100,048, which is a continuation-in-part of application No. 08/466,906, filed on Jun. 6, 1995, now Pat. No. 5,849,871, which is a division of application No. 07/886,979, filed on Apr. 10, 1992, now Pat. No. 5,532,347, which is a continuation-in-part of application No. 08/478,992, filed on Jun. 7, 1995, now Pat. No. 5,773,229, which is a division of application No. 08/077,673, filed on Jun. 15, 1993, which is a division of application No. 07/866,560, filed on Apr. 10, 1992, now Pat. No. 5,280,112, said application No. 09/097,231, filed on Jun. 12, 1998, is a continuation-in-part of application No. 08/044,812, filed on Apr. 8, 1993, now Pat. No. 5,837,521.

(60) Provisional application No. 60/050,063, filed on Jun. 13, 1997.

(51) Int. Cl.[7] .............................. A01K 67/00; C12N 5/10; C12N 15/00; C07K 1/00; G01N 33/566

(52) U.S. Cl. ................................. 800/3; 800/13; 800/18; 530/312; 530/350; 536/23.5; 435/7.21; 435/69.1; 435/320.1; 435/325

(58) Field of Search .................................. 435/7.21, 69.1, 435/320.1, 325; 530/350, 312, 351, 399; 536/23.5; 800/13, 3, 18

(56) References Cited

U.S. PATENT DOCUMENTS

| | | | |
|---|---|---|---|
| 4,683,195 | 7/1987 | Mullis et al. | 435/6 |
| 5,280,112 | 1/1994 | Cone et al. | 536/358 |
| 5,532,347 | 7/1996 | Cone et al. | 536/23.5 |
| B1 4,683,202 | 11/1990 | Mullis | 435/91 |

FOREIGN PATENT DOCUMENTS

| | | |
|---|---|---|
| WO9321315 | 10/1993 | (WO). |
| WO9321316 | 10/1993 | (WO). |

OTHER PUBLICATIONS

Wall RJ Theriogenology 45:57–68, 1996.*
(Kappel et al. Current Opinion in Biotechnology 3:358–353 1992.*
Viville, in Transgenic Animals, Houdebine (eds), Harwood academic publishers, France. pp. 307–321, 1997.*
Ahmed et al., "Isolation and partial purification of a melanocyte–stimulating hormone receptor from B16 murine melanoma cells. A novel approach using a cleavable biotinylated photoactivated ligand and streptavidin–coated magnetic beads," *The Biochemical Journal* 286:377–382 (Sep. 1, 1992).
Bergendahl et al., "Short–Term Starvation Decreases POMC mRNA but Does Not Alter GnRH mRNA in the Brain of Adult Male Rats," *Neuroendocrinol.* 56:913–920 (1992).
Bertling, "Transfection of a DNA/Protein Complex into Nuclei of Mammalian Cells Using Polyoma Capsids and Electroporation," *Bioscience Reports* 7:107–112 (1987).
Bost et al., "Molecular characterization of a corticotropin receptor," *Molecular and Cellular Endocrinology* 44:1–9 (1986).
Bost et al., "Similarity between the corticotropin (ACTH) receptor and a peptide encoded by an RNA that is complementary to ACTH mRNA," *PNAS* 82:1372–1375 (Mar. 1985).
Brady et al., "Altered Expression of Hypothalamic Neuropeptide mRNAs in Food–Restricted and Food–Deprived Rats," *Neuroendocrinol.* 52:441–447 (1990).
Buckley & Ramachandran, "Characterization of corticotropin receptors on adrenocortical cells," *Proc. Natl. Acad. Sci. USA* 78:7431–7435 (1981).
Chen & Okayama, "High–Efficiency Transformation of Mammalian Cells by Plasmid DNA," *Mol. Cell. Biol.* 7:2745–2752 (1987).

(List continued on next page.)

Primary Examiner—Deborah J. R. Clark
Assistant Examiner—Sumesh Kaushal
(74) Attorney, Agent, or Firm—McDonnell Boehnen Hulbert & Berghoff

(57) ABSTRACT

This invention provides methods and reagents for developing naturally-occurring and synthetic agonists and antagonists specific for a mammalian melanocortin receptor, and the use of such agonists and antagonists for treatment and alleviation of dysfunction and disease. The invention specifically provides reagents and methods for developing naturally-occurring and synthetic agonists and antagonists specific for a mammalian melanocortin receptor termed MC5-R. The naturally-occurring and synthetic agonists and antagonists specific for the MC5-R receptor are provided by the invention for the treatment, control, amelioration and alleviation of diseases, and dysfunctional and abnormal states related to thermoregulatory disorders, as well as other diseases relating to exocrine gland disorders, including lacrimal gland dysfunction and sebaceous gland disorders including acne and other skin problems. Also provided by the invention are nucleic acids, constructs, vectors and methods for producing an animal bearing a genetically-disrupted endogenous MC5-R melanocortin receptor, in both the heterozygous and homozygous condition, preferably a rodent and most preferably a mouse. Rodents bearing genetically disrupted MC5-R genes homozygously, termed "gene knockout"rodents in the art, are also advantageously provided.

13 Claims, 55 Drawing Sheets

OTHER PUBLICATIONS

Chen et al., "A Colorimetric Assay for Measuring Activation of $G_s$- and $G_\alpha$-Coupled Signaling Pathways," *Analyt. Biochem.* 226:349–354 (1995).

Chhajlani et al., "Molecular cloning and expression of the human melanocyte stimulating hormone receptor cDNA," *FEBS Letters* 309(3):417–420 (Sep. 14, 1992).

Chirgwin et al., "Isolation of Biologically Active Ribonucleic Acid for Sources Enriched in Ribonuclease," *Biochemistry* 18:5294–5299 (1979).

DeWied & Jolles, "Neuropeptides derived from pro–opiocortin: Behavioral, physiological and neurochemical effects," *Physiol. Rev.* 62:976–1059 (1982).

Dixon et al., "Structural features required for ligand binding to the β–adrenergic receptor," *EMBO J.* 6:3269–3275 (1987).

Eberle et al., "Receptor–specific antibodies by immunization with 'antisense' peptides?," *Peptide Research* 2(3):213–220 (1989).

Felgner et al., "Enhanced Gene Delivery and Mechanism Studies with a Novel Series of Cationic Lipid Formulations," *J. Biol. Chem.* 269:2550–2561 (1994).

Fink et al., "The CGTCA sequence motif is essential for biological activity of the vasoactive intestinal peptide gene cAMP–regulated enhancer," *Proc. Natl. Acad. Sci. USA* 85:6662–6666 (1988).

Gantz et al., "Molecular Cloning of a Novel Melanocortin Receptor," *J. Biol. Chem.* 268:8246–8250 (1993).

Gerst et al., "Dual Regulation of β–Melanotropin Receptor Function and Adenylate Cyclase by Calcium and Guanosine Nucleotides in the M2r Melanoma Cell Line," *Mol. Pharmacol.* 31:81–88 (1987).

Gilman, "A Protein Binding Assay for Adenosine 3':5'–Cyclic Monophosphate," *Proc. Natl. Acad. Sci. USA* 67:305–312 (1979).

Grahame–Smith et al., "Adenosine 3':5'–Monophosphate as the Intracellular Mediator of the Action of Adrenocorticotropic Hormone on the Adrenal Cortex," *J. Biol. Chem.* 242:5535–5541 (1967).

Gruber & Callahan, "ACTH–(4–10) through gamma–MSH: evidence for a new class of central autonomic nervous system–regulating peptides," *Am. Physiol. Soc.* 257:R681–R694 (1989).

Hanneman et al., "Peptides encoded by the pro–opiomelanocortin gene," in *Peptide Hormone as Prohormones*, G. Martinez, ed. (Ellis Horwood Ltd.: Chichester, UK) pp. 53–82 (1987).

Hofmann et al., "Radioactive probes for adrenocorticotropic hormone receptors," *Biochemistry* 25(6):1339–1346 (Mar. 25, 1986).

Hruby et al., "Cyclic Lactam α–Melanotropin Analogues of Ac–Nle$^4$–cyclo[Asp$^5$,D–Phe$^7$,Lys$^{10}$] α–Melanocyte–Stimulating Hormone–(4–10)–NH$_2$ with Bulky Aromatic Amino Acids at Position 7 Show High Antagonist Potency and Selectivity at Specific Melanocortin Receptors," *J. Med. Chem.* 38:3454–3461 (1995).

Kameyama et al., "Expression of melanocyte stimulating hormone receptors correlates with mammalian pigmentation, and can be modulated by interferons," *J. Cellular Physiology* 137(1):35–44 (Oct. 1988).

Karnik et al., "Cysteine residues 110 and 187 are essential for the formation of correct structure in bovine rhodopsin," *Proc. Natl. Acad. Sci. USA* 85:8459–8463 (1988).

Klein et al., "Pressor and cardioaccelerator effect of gamma MSH and related peptides," *Life Sci.* 36:769–775 (1985).

Labbe et al., "Molecular Cloning of a Mouse Melanocortin 5 Receptor Gene Widley Expressed in Peripheral Tissues," *Biochem.* 33:4543–4549 (1994).

Laursen and Belknap, "Intracerebroventricular Injections in Mice," *J. Pharmacol. Methods* 16:355–357 (1986).

Leiba et al., "The melanocortin receptor in the rat lacrimal gland: a model system for the study of MSH (melanocyte stimulating hormone) as a potential neurotransmitter," *European Journal of Pharmacology* 181(1–2):71–82 (May 31, 1990).

Libert et al., "Selective Amplification and Cloning of Four New Members of the G Protein–Coupled Receptor Family," *Science* 244:569 (1989).

Lin et al., "A γ–melanocyte stimulating hormone–like peptide causes reflex natriuresis after acute unilaterasl nephrectomy," *Hypertension* 10:619–627 (1987).

Ling et al., "Synthesis and biological activity of four gamma–melanotropin peptides derived from the cryptic region of the adrenocorticotropin/β–lipotropin precursor," *Life Sci.* 25:1773–1780 (1979).

Lu et al., "Agouti protein is an antagonist of the melanocyte–stimulating–hormone receptor," *Nature* 371:799–802 (1994).

Masu et al., "cDNA cloning of bovine substance–K receptor through oocyte expression system," *Nature* 329:836–838 (1987).

Matsuda et al., "Structure of a cannabinoid receptor and functional expression of the cloned cDNA," *Nature* 346:561–564 (1990).

Mertz et al., "Adrenocorticotropin receptors: Functional expression from rat adrenal mRNA in *Xenopus laevis* oocytes," *PNAS* 88:8525–8529 (1991).

Moore et al., *Endocrinology* 34:107–114 (1991).

Moutjoy et al., "Localization of the Melanocortin–4 Receptor (MC4–R) in Neuroendocrine and Autonomic Control Circuits in the Brain," *Mole. Endocrinol.* 8:1298–1308 (1994).

Mountjoy et al., "The cloning of a family of genes that encode the melanocortin receptors," *Science* 257:1248–1251 (1992).

Oelofsen & Ramachandran, "Studies of Corticotropin Receptors on Rat Adipocytes," *Arch. Biochem. Biophys.* 225:414–421 (1983).

Oki et al., "γ–MSH Fragments from ACTH–β–LPH Precursor Have an Affinity for Opiate Receptors," *Eur. J. Pharmacol.* 64:161–164 (1980).

Pawalek, "Studies on the Cloudman Melanoma Cell Line as a Model for the Action of MSH," *Yale J. Biol. Med.* 58:571–578 (1985).

Pawelek, "Factors Regulating Growth and Pigmentation of Melanoma Cells," *J. Invest. Dermatol.* 66:201–209 (1976).

Roselli–Rehfuss et al., "Identification of a receptor for γ melanotropin and other proopiomelanocortin peptides in the hypothalamus and limbic system," *Proc. Natl. Acad. Sci. USA* 90:8856–8860 (1993).

Saiki et al., "Primer–Directed Enzymatic Amplification of DNA with a Thermostable DNA Polymerase," *Science* 239:487–491 (1988).

Sambrook et al., 1990, *Molecular Cloning: A Laboratory Manual* (Cold Spring Harbor Press: New York).

Sanger et al., "DNA sequencing with chain–terminating inhibitors," *Proc. Natl. Acad. Sci. USA* 74:5463–5467 (1977).

Schild, "pA, A New Scale for the Measurement of Drug Antagonism," *Brit. J. Pharmacol.* 2:189–206 (1947).

Schimmer et al., "Adrenocorticotropin–Resistant Mutants of the Y1 Adrenal Cell Line Fail to Express the Adrenocorticotropin Receptor," *J. Cell Physiol.* 163:164–171 (1995).

Schimuze, "Thirty–five years of progress in the study of MSH," *Yale J. Biol. Med.* 58:561–570 (1985).

Shimuzu et al., "Effects of MSH on Food Intake, Body Weight and Coat Color of the Yellow Obese Mouse," *Life Sci.* 45:543–552 (1989).

Siegrist et al., "Characterization of Receptors for α–Melanocyte–stimulating Hormone on Human Melanoma Cells," *Cancer Research* 49:6352–6358 (Nov. 15, 1989).

Siegrist et al., "Quantification of MSH receptors on mouse melanoma tissue by receptor autoradiography," *J. Receptor Res.* 11:323–331 (1991).

Slominski et al., "Melanotropic activity of gamma MSH peptides in melanoma cells," *Life Sci.* 50:1103–1108 (1992).

Smithies et al., "Insertion of DNA sequences into the human chromosomal β–globin locus by homologous recombination," *Nature* 317:230–234 (1985).

Solca et al., "The receptor for α–melanotropin of mouse and human melanoma cells," *J. Biol. Chem.* 264:14277–14280 (1989).

Spindel et al., "Cloning and Functional Characterization of a Complementary DNA Encoding the Murine Fibroblast Bobmesin/Gastrin–Releasing Peptide Receptor," *Mol. Endocrinol.* 4:1956–1963 (1990).

Tatro & Reichlin, "Specific receptors for α–melanocyte–stimulating hormone are widely distributed in tissues of rodents," *Endocrinology* 121:1900–1907 (1987).

Tatro et al., "Melanotropin Receptors of Murine Melanoma Characterized in Cultured Cells and Demonstrated in Experimental Tumors in Situ," *Cancer Res.* 50:1237–1242 (1990).

Thomas & Capecchi, "Site–Directed Mutagenesis by Gene Targeting in Mouse Embryo–Derived Stem Cells," *Cell* 51:503–512 (1987).

*Tissue Culture*, Academic Press, Kruse & Patterson, editors (1973).

Tsujii et al., "Acetylation Alters the Feeding Response to MSH and Beta–Endorphin," *Brian Res. Bull.* 23:165–169 (1989).

Yen et al., "Obesity, diabetes, and neoplasia in yellow $A^{vy}$/–mice: ectopic expression of the agouti gene," *FASEB J.* 8:479–488 (1994).

Zhou et al., "Cloning and expression of human and rat $D_1$ dopamine receptors," *Nature* 347:76–80 (Sep. 1990).

* cited by examiner-

FIG. 1A

```
TTCCTGACAA GACT ATG TCC ACT CAG GAG CCC CAG AAG AGT CTT CTG GGT           50
                Met Ser Thr Gln Glu Pro Gln Lys Ser Leu Leu Gly
                 1               5                  10

TCT CTC AAC TCC AAT GCC ACC TCT CAC CTT GGA CTG GCC ACC AAC CAG           98
Ser Leu Asn Ser Asn Ala Thr Ser His Leu Gly Leu Ala Thr Asn Gln
            15              20                  25

TCA GAG CCT TGG TGC CTG TAT GTG TCC ATC CCA GAT GGC CTC TTC CTC          146
Ser Glu Pro Trp Cys Leu Tyr Val Ser Ile Pro Asp Gly Leu Phe Leu
        30              35                  40

AGC CTA GGG CTG GTG AGT CTG GTG GAG AAT GTG CTG GTT GTG ATA GCC          194
Ser Leu Gly Leu Val Ser Leu Val Glu Asn Val Leu Val Val Ile Ala
    45              50                  55                  60

ATC ACC AAA AAC CGC AAC CTG CAC TCG CCC ATG TAT TAC TTC ATC TGC          242
Ile Thr Lys Asn Arg Asn Leu His Ser Pro Met Tyr Tyr Phe Ile Cys
                 65                  70                  75

TGC CTG GCC CTG TCT GAC CTG ATG GTA AGT GTC AGC ATC GTG CTG GAG          290
Cys Leu Ala Leu Ser Asp Leu Met Val Ser Val Ser Ile Val Leu Glu
            80                  85                  90

ACT ACT ATC ATC CTG CTG CTG GAG GTG GGC ATC CTG GTG GCC AGA GTG          338
Thr Thr Ile Ile Leu Leu Leu Glu Val Gly Ile Leu Val Ala Arg Val
        95                 100                 105

GCT TTG GTG CAG CAG CTG GAC AAC CTC ATT GAC GTG CTC ATC TGT GGC          386
Ala Leu Val Gln Gln Leu Asp Asn Leu Ile Asp Val Leu Ile Cys Gly
    110                 115                 120

TCC ATG GTG TCC AGT CTC TGC TTC CTG GGC ATT ATT GCT ATA GAC CGC          434
Ser Met Val Ser Ser Leu Cys Phe Leu Gly Ile Ile Ala Ile Asp Arg
125                 130                 135                 140

TAC ATC TCC ATC TTC TAT GCG CTG CGT TAT CAC AGC ATC GTG ACG CTG          482
Tyr Ile Ser Ile Phe Tyr Ala Leu Arg Tyr His Ser Ile Val Thr Leu
                145                 150                 155

CCC AGA GCA CGA CGG GCT GTC GTG GGC ATC TGG ATG GTC AGC ATC GTC          530
Pro Arg Ala Arg Arg Ala Val Val Gly Ile Trp Met Val Ser Ile Val
                160                 165                 170
```

FIG. 1B

```
TCC AGC ACC CTC TTT ATC ACC TAC TAC AAG CAC ACA GCC GTT CTG CTC            578
Ser Ser Thr Leu Phe Ile Thr Tyr Tyr Lys His Thr Ala Val Leu Leu
        175                 180                 185

TGC CTC GTC ACT TTC TTT CTA GCC ATG CTG GCA CTC ATG GCG ATT CTG            626
Cys Leu Val Thr Phe Phe Leu Ala Met Leu Ala Leu Met Ala Ile Leu
        190                 195                 200

TAT GCC CAC ATG TTC ACG AGA GCG TGC CAG CAC GTC CAG GGC ATT GCC            674
Tyr Ala His Met Phe Thr Arg Ala Cys Gln His Val Gln Gly Ile Ala
205                 210                 215                 220

CAG CTC CAC AAA AGG CGG CGG TCC ATC CGC CAA GGC TTC TGC CTC AAG            722
Gln Leu His Lys Arg Arg Arg Ser Ile Arg Gln Gly Phe Cys Leu Lys
                225                 230                 235

GGT GCT GCC ACC CTT ACT ATC CTT CTG GGG ATT TTC TTC CTG TGC TGG            770
Gly Ala Ala Thr Leu Thr Ile Leu Leu Gly Ile Phe Phe Leu Cys Trp
            240                 245                 250

GGC CCC TTC TTC CTG CAT CTC TTG CTC ATC GTC CTC TGC CCT CAG CAC            818
Gly Pro Phe Phe Leu His Leu Leu Leu Ile Val Leu Cys Pro Gln His
                255                 260                 265

CCC ACC TGC AGC TGC ATC TTC AAG AAC TTC AAC CTC TTC CTC CTC CTC            866
Pro Thr Cys Ser Cys Ile Phe Lys Asn Phe Asn Leu Phe Leu Leu Leu
        270                 275                 280

ATC GTC CTC AGC TCC ACT GTT GAC CCC CTC ATC TAT GCT TTC CGC AGC            914
Ile Val Leu Ser Ser Thr Val Asp Pro Leu Ile Tyr Ala Phe Arg Ser
285                 290                 295                 300

CAG GAG CTC CGC ATG ACA CTC AAG GAG GTG CTG CTG TGC TCC TGG                959
Gln Glu Leu Arg Met Thr Leu Lys Glu Val Leu Leu Cys Ser Trp
                    305                 310                 315

TGATCAGAGG GCGCTGGGCA GAGGGTGACA GTGATATCCA GTGGCCTGCA TCTGTGAGAC         1019

CACAGGTACT CATCCCTTCC TGATCTCCAT TTGTCTAAGG GTCGACAGGA TGAGCTTTAA         1079

AATAGAAACC CAGAGTGCCT GGGGCCAGGA GAAAGGGTAA CTGTGACTGC AGGGCTCACC         1139

CAGGGCAGCT ACGGGAAGTG GAGGAGACAG GGATGGGAAC TCTAGCCCTG AGCAAGGGTC         1199

AGACCACAGG CTCCTGAAGA GCTTCACCTC TCCCCACCTA CAGGCAACTC CTGCTCAAGC         1259
C                                                                         1260
```

FIG. 2A

```
CCCGCATGTG GCCGCCCTCA ATGGAGGGCT CTGAGAACGA CTTTTAAAAC GCAGAGAAAA        60

AGCTCCATTC TTCCCAGACC TCAGCGCAGC CCTGGCCCAG GAAGGGAGGA GACAGAGGCC       120

AGGACGGTCC AGAGGTGTCG AAATGTCCTG GGAACCTGAG CAGCAGCCAC CAGGGAAGAG       180

GCAGGGAGGG AGCTGAGGAC CAGGCTTGGT TGTGAGAATC CCTGAGCCCA GGCGGTTGAT       240

GCCAGGAGGT GTCTGGACTG GCTGGGCCAT GCCTGGGCTG ACCTGTCCAG CCAGGGAGAG       300

GGTGTGAGGG CAGATCTGGG GGTGCCCAGA TGGAAGGAGG CAGGCATGGG GACACCCAAG       360

GCCCCCTGGC AGCACCATGA ACTAAGCAGG ACACCTGGAG GGGAAGAACT GTGGGGACCT       420

GGAGGCCTCC AACGACTCCT TCCTGCTTCC TGGACAGGAC T ATG GCT GTG CAG           473
                                             Met Ala Val Gln
                                               1
```

```
GGA TCC CAG AGA AGA CTT CTG GGC TCC CTC AAC TCC ACC CCC ACA GCC        521
Gly Ser Gln Arg Arg Leu Leu Gly Ser Leu Asn Ser Thr Pro Thr Ala
  5              10                 15                 20

ATC CCC CAG CTG GGG CTG GCT GCC AAC CAG ACA GGA GCC CGG TGC CTG        569
Ile Pro Gln Leu Gly Leu Ala Ala Asn Gln Thr Gly Ala Arg Cys Leu
             25                 30                 35

GAG GTG TCC ATC TCT GAC GGG CTC TTC CTC AGC CTG GGG CTG GTG AGC        617
Glu Val Ser Ile Ser Asp Gly Leu Phe Leu Ser Leu Gly Leu Val Ser
             40                 45                 50

TTG GTG GAG AAC GCG CTG GTG GTG GCC ACC ATC GCC AAG AAC CGG AAC        665
Leu Val Glu Asn Ala Leu Val Val Ala Thr Ile Ala Lys Asn Arg Asn
         55                 60                 65

CTG CAC TCA CCC ATG TAC TGC TTC ATC TGC TGC CTG GCC TTG TCG GAC        713
Leu His Ser Pro Met Tyr Cys Phe Ile Cys Cys Leu Ala Leu Ser Asp
         70                 75                 80

CTG CTG GTG AGC GGG ACG AAC GTG CTG GAG ACG GCC GTC ATC CTC CTG        761
Leu Leu Val Ser Gly Thr Asn Val Leu Glu Thr Ala Val Ile Leu Leu
 85                 90                 95                100

CTG GAG GCC GGT GCA CTG GTG GCC CGG GCT GCG GTG CTG CAG CAG CTG        809
Leu Glu Ala Gly Ala Leu Val Ala Arg Ala Ala Val Leu Gln Gln Leu
                105                110                115

GAC AAT GTC ATT GAC GTG ATC ACC TGC AGC TCC ATG CTG TCC AGC CTC        857
Asp Asn Val Ile Asp Val Ile Thr Cys Ser Ser Met Leu Ser Ser Leu
                120                125                130

TGC TTC CTG GGC GCC ATC GCC GTG GAC CGC TAC ATC TCC ATC TTC TAC        905
Cys Phe Leu Gly Ala Ile Ala Val Asp Arg Tyr Ile Ser Ile Phe Tyr
                135                140                145

GCA CTG CGC TAC CAC AGC ATC GTG ACC CTG CCG CGG GCG CCG CGA GCC        953
Ala Leu Arg Tyr His Ser Ile Val Thr Leu Pro Arg Ala Pro Arg Ala
    150                155                160
```

FIG. 2B

```
GTT GCG GCC ATC TGG GTG GCC AGT GTC GTC TTC AGC ACG CTC TTC ATC      1001
Val Ala Ala Ile Trp Val Ala Ser Val Val Phe Ser Thr Leu Phe Ile
165             170             175             180

GCC TAC TAC GAC CAC GTG GCC GTC CTG CTG TGC CTC GTG GTC TTC TTC      1049
Ala Tyr Tyr Asp His Val Ala Val Leu Leu Cys Leu Val Val Phe Phe
                185             190             195

CTG GCT ATG CTG GTG CTC ATG GCC GTG CTG TAC GTC CAC ATG CTG GCC      1097
Leu Ala Met Leu Val Leu Met Ala Val Leu Tyr Val His Met Leu Ala
            200             205             210

CGG GCC TGC CAG CAC GCC CAG GGC ATC GCC CGG CTC CAC AAG AGG CAG      1145
Arg Ala Cys Gln His Ala Gln Gly Ile Ala Arg Leu His Lys Arg Gln
        215             220             225

CGC CCG GTC CAC CAG GGC TTT GGC CTT AAA GGC GCT GTC ACC CTC ACC      1193
Arg Pro Val His Gln Gly Phe Gly Leu Lys Gly Ala Val Thr Leu Thr
    230             235             240

ATC CTG CTG GGC ATT TTC TTC CTC TGC TGG GGC CCC TTC TTC CTG CAT      1241
Ile Leu Leu Gly Ile Phe Phe Leu Cys Trp Gly Pro Phe Phe Leu His
245             250             255             260

CTC ACA CTC ATC GTC CTC TGC CCC GAG CAC CCC ACG TGC GGC TGC ATC      1289
Leu Thr Leu Ile Val Leu Cys Pro Glu His Pro Thr Cys Gly Cys Ile
            265             270             275

TTC AAG AAC TTC AAC CTC TTT CTC GCC CTC ATC ATC TGC AAT GCC ATC      1337
Phe Lys Asn Phe Asn Leu Phe Leu Ala Leu Ile Ile Cys Asn Ala Ile
        280             285             290

ATC GAC CCC CTC ATC TAC GCC TTC CAC AGC CAG GAG CTC CGC AGG ACG      1385
Ile Asp Pro Leu Ile Tyr Ala Phe His Ser Gln Glu Leu Arg Arg Thr
    295             300             305

CTC AAG GAG GTG CTG ACA TGC TCC TGG TGAGCGCGGT GCACGCGCTT            1432
Leu Lys Glu Val Leu Thr Cys Ser Trp
310             315

TAAGTGTGCT GGGCAGAGGG AGGTGGTGAT ATTGTGGTCT GGTTCCTGTG TGACCCTGGG    1492

CAGTTCCTTA CCTCCCTGGT CCCCGTTTGT CAAAGAGGAT GGACTAAATG ATCTCTGAAA    1552

GTGTTGAAGC GCGGACCCTT CTGGGCAGGG AGGGGTCCTG CAAAACTCCA GGCAGGACTT    1612

CTCACCAGCA GTCGTGGGAA C                                              1633
```

FIG. 3A

| | |
|---|---|
| ACAACACTTT ATATATATTT TTATAAATGT AAGGGGTACA AAGGTGCCAT TTTGTTACAT | 60 |
| GGATATACCG TGTAGTGGTG AAGCCTGGGC TTTTAGTGTA TCTGTCATCA GAATAACATA | 120 |
| CGTGTTACCC ATAGGAATTT CTCATCACCC GCCCCCTCCA CCCTTCGAGT CTCCAATGTC | 180 |
| CATTCCACAC TCTATATCCA CGTGTATGCA TATAGCTCCA CATATAAGTG AGAACATGTA | 240 |
| GTATTTGACT TCCTCTTTCT GAGTTATTTC ACTTTGATAA TGGCCTCCAC TTCCATCCAT | 300 |
| GTTGCTGCAA AAGACATGAC CTTATTCTTT TTGATAGCTG GGGAGTACTC CATTGTGTAT | 360 |
| ATGTACCACA TTTCTTTATC CATTCACCCA TTGAGAACAC TTAGTTGATT CCATATCTTT | 420 |
| GCTATTGTCA CTAGTGCTGC AATAAACATA CATGTGCAGG CTCCTTCTAA TATACTGATT | 480 |
| TATATTTTAT GGAGAGAGAT AGAGTTCTTA GCGAGTGTGC TGTTTATTTC TAGTGTACTT | 540 |
| GCAACTAATA TTCTGTATAC TCCCTTTAGG TGATTGGAGA TTTAACTTAG ATCTCCAGCA | 600 |
| AGTGCTACAA GAAGAAAAGA TCCTGAAGAA TCAATCAAGT TTCCGTGAAG TCAAGTCCAA | 660 |
| GTAACATCCC CGCCTTAACC ACAAGCAGGA GAA ATG AAG CAC ATT ATC AAC TCG | 714 |
|                                                                              Met Lys His Ile Ile Asn Ser<br>                                                                               1                       5 | |
| TAT GAA AAC ATC AAC AAC ACA GCA AGA AAT AAT TCC GAC TGT CCT CGT<br>Tyr Glu Asn Ile Asn Asn Thr Ala Arg Asn Asn Ser Asp Cys Pro Arg<br>          10                      15                        20 | 762 |
| GTG GTT TTG CCG GAG GAG ATA TTT TTC ACA ATT TCC ATT GTT GGA GTT<br>Val Val Leu Pro Glu Glu Ile Phe Phe Thr Ile Ser Ile Val Gly Val<br>    25                        30                        35 | 810 |
| TTG GAG AAT CTG ATC GTC CTG CTG GCT GTG TTC AAG AAT AAG AAT CTC<br>Leu Glu Asn Leu Ile Val Leu Leu Ala Val Phe Lys Asn Lys Asn Leu<br>  40                        45                        50                        55 | 858 |
| CAG GCA CCC ATG TAC TTT TTC ATC TGT AGC TTG GCC ATA TCT GAT ATG<br>Gln Ala Pro Met Tyr Phe Phe Ile Cys Ser Leu Ala Ile Ser Asp Met<br>                    60                        65                        70 | 906 |
| CTG GGC AGC CTA TAT AAG ATC TTG GAA AAT ATC CTG ATC ATA TTG AGA<br>Leu Gly Ser Leu Tyr Lys Ile Leu Glu Asn Ile Leu Ile Ile Leu Arg<br>          75                      80                        85 | 954 |
| AAC ATG GGC TAT CTC AAG CCA CGT GGC AGT TTT GAA ACC ACA GCC GAT<br>Asn Met Gly Tyr Leu Lys Pro Arg Gly Ser Phe Glu Thr Thr Ala Asp<br>          90                      95                        100 | 1002 |
| GAC ATC ATC GAC TCC CTG TTT GTC CTC TCC CTG CTT GGC TCC ATC TTC<br>Asp Ile Ile Asp Ser Leu Phe Val Leu Ser Leu Leu Gly Ser Ile Phe<br>105                        110                        115 | 1050 |

FIG. 3B

```
AGC CTG TCT GTG ATT GCT GCG GAC CGC TAC ATC ACC ATC TTC CAC GCA      1098
Ser Leu Ser Val Ile Ala Ala Asp Arg Tyr Ile Thr Ile Phe His Ala
120                 125                 130                 135

CTG CGG TAC CAC AGC ATC GTG ACC ATG CGC CGC ACT GTG GTG GTG CTT      1146
Leu Arg Tyr His Ser Ile Val Thr Met Arg Arg Thr Val Val Val Leu
                140                 145                 150

ACG GTC ATC TGG ACG TTC TGC ACG GGG ACT GGC ATC ACC ATG GTG ATC      1194
Thr Val Ile Trp Thr Phe Cys Thr Gly Thr Gly Ile Thr Met Val Ile
            155                 160                 165

TTC TCC CAT CAT GTG CCC ACA GTG ATC ACC TTC ACG TCG CTG TTC CCG      1242
Phe Ser His His Val Pro Thr Val Ile Thr Phe Thr Ser Leu Phe Pro
        170                 175                 180

CTG ATG CTG GTC TTC ATC CTG TGC CTC TAT GTG CAC ATG TTC CTG CTG      1290
Leu Met Leu Val Phe Ile Leu Cys Leu Tyr Val His Met Phe Leu Leu
    185                 190                 195

GCT CGA TCC CAC ACC AGG AAG ATC TCC ACC CTC CCC AGA GCC AAC ATG      1338
Ala Arg Ser His Thr Arg Lys Ile Ser Thr Leu Pro Arg Ala Asn Met
200                 205                 210                 215

AAA GGG GCC ATC ACA CTG ACC ATC CTG CTC GGG GTC TTC ATC TTC TGC      1386
Lys Gly Ala Ile Thr Leu Thr Ile Leu Leu Gly Val Phe Ile Phe Cys
                220                 225                 230

TGG GCC CCC TTT GTG CTT CAT GTC CTC TTG ATG ACA TTC TGC CCA AGT      1434
Trp Ala Pro Phe Val Leu His Val Leu Leu Met Thr Phe Cys Pro Ser
            235                 240                 245

AAC CCC TAC TGC GCC TGC TAC ATG TCT CTC TTC CAG GTG AAC GGC ATG      1482
Asn Pro Tyr Cys Ala Cys Tyr Met Ser Leu Phe Gln Val Asn Gly Met
        250                 255                 260

TTG ATC ATG TGC AAT GCC GTC ATT GAC CCC TTC ATA TAT GCC TTC CGG      1530
Leu Ile Met Cys Asn Ala Val Ile Asp Pro Phe Ile Tyr Ala Phe Arg
    265                 270                 275

AGC CCA GAG CTC AGG GAC GCA TTC AAA AAG ATG ATC TTC TGC AGC AGG      1578
Ser Pro Glu Leu Arg Asp Ala Phe Lys Lys Met Ile Phe Cys Ser Arg
280                 285                 290                 295

TAC TGG TAGAATGGCT GATCCCTGGT TTTAGAATCC ATGGGAATAA CGTTGCCAAG       1634
Tyr Trp

TGCCAGAATA GTGTAACATT CCAACAAATG CCAGTGCTCC TCACTGGCCT TCCTTCCCTA    1694
ATGGATGCAA GGATGACCCA CCAGCTAGTG TTTCTGAATA CTATGGCCAG GAACAGTCTA    1754
TTGTAGGGGC AACTCTATTT GTGACTGGAC AGATAAAACG TGTAGTAAAA GAAGGATAGA    1814
ATACAAAGTA TTAGGTACAA AAGTAATTAG GTTTGCATTA CTTATGACAA ATGCATTACT    1874
TTTGCACCAA TCTAGTAAAA CAGCAATAAA AATTCAAGGG CTTTGGGCTA AGGCAAAGAC    1934
TTGCTTTCCT GTGGACATTA ACAAGCCAGT TCTGAGGCGG CCTTTCCAGG TGGAGGCCAT    1994
TGCAGCCAAT TTCAGAGT                                                  2012
```

FIG. 4A

| | |
|---|---|
| GGGGCCAGAA AGTTCCTGCT TCAGAGCAGA AGATCTTCAG CAAGAACTAC AAAGAAGAAA | 60 |
| AGATTCTGGA GAATCAATCA AGTTTCCTGT CAAGTTCCAG TAACGTTTCT GTCTTAACTG | 120 |
| CACACAGGAA AG ATG AAA CAC ATT CTC AAT CTG TAT GAA AAC ATC AAC | 168 |
|                     Met Lys His Ile Leu Asn Leu Tyr Glu Asn Ile Asn | |
|                      1                 5               10 | |
| AGT ACA GCA AGA AAT AAC TCA GAC TGT CCT GCT GTG ATT TTG CCA GAA | 216 |
| Ser Thr Ala Arg Asn Asn Ser Asp Cys Pro Ala Val Ile Leu Pro Glu | |
|         15               20               25 | |
| GAG ATA TTT TTC ACA GTA TCC ATT GTT GGG GTT TTG GAG AAC CTG ATG | 264 |
| Glu Ile Phe Phe Thr Val Ser Ile Val Gly Val Leu Glu Asn Leu Met | |
|      30               35               40 | |
| GTC CTT CTG GCT GTG GCC AAG AAT AAG AGT CTT CAG TCG CCC ATG TAC | 312 |
| Val Leu Leu Ala Val Ala Lys Asn Lys Ser Leu Gln Ser Pro Met Tyr | |
| 45               50               55               60 | |
| TTT TTC ATC TGC AGC TTG GCT ATT TCC GAT ATG CTG GGG AGC CTG TAC | 360 |
| Phe Phe Ile Cys Ser Leu Ala Ile Ser Asp Met Leu Gly Ser Leu Tyr | |
|            65                   70               75 | |
| AAG ATT TTG GAA AAC GTT CTG ATC ATG TTC AAA AAC ATG GGT TAC CTC | 408 |
| Lys Ile Leu Glu Asn Val Leu Ile Met Phe Lys Asn Met Gly Tyr Leu | |
|               80                   85               90 | |
| GAG CCT CGA GGC AGT TTT GAA AGC ACA GCA GAT GAT GTG GTG GAC TCC | 456 |
| Glu Pro Arg Gly Ser Phe Glu Ser Thr Ala Asp Asp Val Val Asp Ser | |
|                95               100              105 | |
| CTG TTC ATC CTC TCC CTT CTC GGC TCC ATC TGC AGC CTG TCT GTG ATT | 504 |
| Leu Phe Ile Leu Ser Leu Leu Gly Ser Ile Cys Ser Leu Ser Val Ile | |
| 110                   115              120 | |
| GCC GCT GAC CGC TAC ATC ACA ATC TTC CAC GCT CTG CAG TAC CAC CGC | 552 |
| Ala Ala Asp Arg Tyr Ile Thr Ile Phe His Ala Leu Gln Tyr His Arg | |
| 125                   130               135             140 | |
| ATC ATG ACC CCC GCA CCG TGC CCT CGT CAT CTG ACG GTC CTC TGG GCA | 600 |
| Ile Met Thr Pro Ala Pro Cys Pro Arg His Leu Thr Val Leu Trp Ala | |
|                  145              150             155 | |
| GGC TGC ACA GGC AGT GGC ATT ACC ATC GTG ACC TTC TCC CAT CAC GTC | 648 |
| Gly Cys Thr Gly Ser Gly Ile Thr Ile Val Thr Phe Ser His His Val | |
|                 160                165           170 | |
| CCC ACA GTG ATC GCC TTC ACA GCG CTG TTC CCG CTG ATG CTG GCC TTC | 696 |
| Pro Thr Val Ile Ala Phe Thr Ala Leu Phe Pro Leu Met Leu Ala Phe | |
|               175              180             185 | |
| ATC CTG TGC CTC TAC GTG CAC ATG TTC CTG CTG GCC CGC TCC CAC ACC | 744 |
| Ile Leu Cys Leu Tyr Val His Met Phe Leu Leu Ala Arg Ser His Thr | |
|          190               195              200 | |
| AGG AGG ACC CCC TCC CTT CCC AAA GCC AAC ATG AGA GGG GCC GTC ACA | 792 |
| Arg Arg Thr Pro Ser Leu Pro Lys Ala Asn Met Arg Gly Ala Val Thr | |
| 205                   210               215             220 | |

FIG. 4B

```
CTG ACT GTC CTG CTC GGG GTC TTC ATT TTC TGT TGG GCA CCC TTT GTC        840
Leu Thr Val Leu Leu Gly Val Phe Ile Phe Cys Trp Ala Pro Phe Val
            225                 230                 235

CTT CAT GTC CTC TTG ATG ACA TTC TGC CCA GCT GAC CCC TAC TGT GCC        888
Leu His Val Leu Leu Met Thr Phe Cys Pro Ala Asp Pro Tyr Cys Ala
            240                 245                 250

TGC TAC ATG TCC CTC TTC CAG GTG AAT GGT GTG TTG ATC ATG TGT AAT        936
Cys Tyr Met Ser Leu Phe Gln Val Asn Gly Val Leu Ile Met Cys Asn
            255                 260                 265

GCC ATC ATC GAC CCC TTC ATA TAT GCC TTT CGG AGC CCA GAG CTC AGG        984
Ala Ile Ile Asp Pro Phe Ile Tyr Ala Phe Arg Ser Pro Glu Leu Arg
            270                 275                 280

GTC GCA TTC AAA AAG ATG GTT ATC TGC AAC TGT TAC CAG TAGAATGATT        1033
Val Ala Phe Lys Lys Met Val Ile Cys Asn Cys Tyr Gln
285                 290                 295

GGTCCCTGAT TTTAGGAGCC ACAGGGATAT ACTGTCAGGG ACAGAGTAGC GTGACAGACC     1093

AACAACACTA GGACT                                                      1108
```

FIG. 5A

| | |
|---|---:|
| GGCTGTAACT GTAGCAACCG GTGTTGGGTG GGGATGAGAA GAGACCAGAG AGAGAGAGGG | 60 |
| TCAGAGCGAC AGGGGATGAG ACAGGCTGGT CAGAGTCTGC ACTGATTGTT GGAGACGCAA | 120 |
| AGGAAAGTTT TTTCTATGTC TCCAACCTCC CCCTCCTCCC CCGTTTCTCT CTGGAGAAAC | 180 |
| TAAAATCTAG ACTGGACAGC ATCCACAAGA GAAGCACCTA GAAGAAGATT TTTTTTTCCC | 240 |
| AGCAGCTTGC TCAGGACCCT GCAGGAGCTG CAGCCGGAAC TGGTCCCGCC GATAACC | 297 |

```
ATG AAC TCT TCC TGC TGC CCG TCC TCC TCT TAT CCG ACG CTG CCT AAC      345
Met Asn Ser Ser Cys Cys Pro Ser Ser Ser Tyr Pro Thr Leu Pro Asn
 1               5                  10                  15

CTC TCC CAG CAC CCT GCA GCC CCC TCT GCC AGC AAC CGG AGT GGC AGT      393
Leu Ser Gln His Pro Ala Ala Pro Ser Ala Ser Asn Arg Ser Gly Ser
            20                  25                  30

GGG TTC TGC GAG CAG GTT TTC ATC AAG CCA GAG GTC TTC CTG GCA CTG      441
Gly Phe Cys Glu Gln Val Phe Ile Lys Pro Glu Val Phe Leu Ala Leu
        35                  40                  45

GGC ATC GTC AGT CTG ATG GAA AAC ATC CTG GTG ATC CTG GCT GTG GTG      489
Gly Ile Val Ser Leu Met Glu Asn Ile Leu Val Ile Leu Ala Val Val
    50                  55                  60

AGG AAC GGC AAC CTG CAC TCC CCC ATG TAC TTC TTC CTG CTG AGC CTG      537
Arg Asn Gly Asn Leu His Ser Pro Met Tyr Phe Phe Leu Leu Ser Leu
65                  70                  75                  80

CTG CAG GCC GAC ATG CTG GTG AGC CTG TCC AAC TCC CTG GAG ACC ATC      585
Leu Gln Ala Asp Met Leu Val Ser Leu Ser Asn Ser Leu Glu Thr Ile
            85                  90                  95

ATG ATC GTG GTT ATC AAC AGC GAC TCC CTG ACC TTG GAG GAC CAA TTC      633
Met Ile Val Val Ile Asn Ser Asp Ser Leu Thr Leu Glu Asp Gln Phe
            100                 105                 110

ATC CAG CAC ATG GAC AAC ATC TTC GAC TCT ATG ATC TGC ATC TCC CTG      681
Ile Gln His Met Asp Asn Ile Phe Asp Ser Met Ile Cys Ile Ser Leu
            115                 120                 125

GTG GCC TCC ATC TGC AAC CTC CTG GCC ATC GCC GTG GAC AGG TAC GTC      729
Val Ala Ser Ile Cys Asn Leu Leu Ala Ile Ala Val Asp Arg Tyr Val
            130                 135                 140

ACC ATC TTC TAT GCC CTC CGT TAC CAC AGC ATC ATG ACG GTT AGG AAA      777
Thr Ile Phe Tyr Ala Leu Arg Tyr His Ser Ile Met Thr Val Arg Lys
145                 150                 155                 160

GCC CTC TCC TTG ATC GTG GCC ATC TGG GTC TGC TGT GGC ATC TGC GGC      825
Ala Leu Ser Leu Ile Val Ala Ile Trp Val Cys Cys Gly Ile Cys Gly
            165                 170                 175

GTG ATG TTC ATC GTC TAC TCC GAG AGC AAG ATG GTC ATC GTG TGC CTC      873
Val Met Phe Ile Val Tyr Ser Glu Ser Lys Met Val Ile Val Cys Leu
            180                 185                 190
```

FIG. 5B

```
ATC ACC ATG TTC TTC GCC ATG GTG CTC CTC ATG GGC ACC CTG TAC ATC            921
Ile Thr Met Phe Phe Ala Met Val Leu Leu Met Gly Thr Leu Tyr Ile
        195                 200                 205

CAC ATG TTC CTC TTC GCC AGG CTG CAC GTC CAG CGC ATC GCG GCA CTG            969
His Met Phe Leu Phe Ala Arg Leu His Val Gln Arg Ile Ala Ala Leu
    210                 215                 220

CCA CCT GCT GAC GGG GTA GCC CCG CAG CAG CAC TCG TGC ATG AAG GGG           1017
Pro Pro Ala Asp Gly Val Ala Pro Gln Gln His Ser Cys Met Lys Gly
225                 230                 235                 240

GCC GTC ACC ATC ACC ATC CTG CTG GGG GTT TTC ATC TTC TGC TGG GCG           1065
Ala Val Thr Ile Thr Ile Leu Leu Gly Val Phe Ile Phe Cys Trp Ala
            245                 250                 255

CCT TTC TTC CTC CAC CTG GTC CTC ATC ATC ACC TGC CCC ACC AAC CCC           1113
Pro Phe Phe Leu His Leu Val Leu Ile Ile Thr Cys Pro Thr Asn Pro
                260                 265                 270

TAC TGC ATC TGC TAC ACG GCG CAC TTC AAC ACC TAC CTG GTT CTC ATC           1161
Tyr Cys Ile Cys Tyr Thr Ala His Phe Asn Thr Tyr Leu Val Leu Ile
        275                 280                 285

ATG TGC AAC TCT GTC ATC GAC CCC CTC ATC TAC GCC TTC CGC AGC CTG           1209
Met Cys Asn Ser Val Ile Asp Pro Leu Ile Tyr Ala Phe Arg Ser Leu
    290                 295                 300

GAG CTG CGA AAC ACC TTC AAG GAG ATT CTC TGC GGT TGC AAT GGC ATG           1257
Glu Leu Arg Asn Thr Phe Lys Glu Ile Leu Cys Gly Cys Asn Gly Met
305                 310                 315                 320

AAC GTG GGC TAGGAACCCC CGAGGAGGTG TTCCACGGCT AGCCAAGAGA                   1306
Asn Val Gly

GAAAAGCAAT GCTCAGGTGA GACACAGAAG GG                                       1338
```

FIG. 6A

```
AGCTTCCGAG AGGCAGCCGA TGTGAGCATG TGCGCACAGA TTCGTCTCCC AATGGCATGG        60

CAGCTTCAAG GAAAATTATT TTGAACAGAC TTGAATGCAT AAGATTAAAG TTAAAGCAGA       120

AGTGAGAACA AGAAAGCAAA GAGCAGACTC TTTCAACTGA GAATGAATAT TTTGAAGCCC       180

AAGATTTTAA AGTGATGATG ATTAGAGTCG TACCTAAAAG AGACTAAAAA CTCCATGTCA       240

AGCTCTGGAC TTGTGACATT TACTCACAGC AGGCATGGCA ATTTTAGCCT CACAACTTTC       300

AGACAGATAA AGACTTGGAG GAAATAACTG AGACGACTCC CTGACCCAGG AGGTTAAATC       360

AATTCAGGGG GACACTGGAA TTCTCCTGCC AGC ATG GTG AAC TCC ACC CAC CGT        414
                                    Met Val Asn Ser Thr His Arg
                                     1                   5
```

| | | | | | | | | | | | | | | | | |
|---|---|---|---|---|---|---|---|---|---|---|---|---|---|---|---|---|
|GGG|ATG|CAC|ACT|TCT|CTG|CAC|CTC|TGG|AAC|CGC|AGC|AGT|TAC|AGA|CTG| 462|
|Gly|Met|His|Thr|Ser|Leu|His|Leu|Trp|Asn|Arg|Ser|Ser|Tyr|Arg|Leu| |
| | |10| | | |15| | | | |20| | | | | |
|CAC|AGC|AAT|GCC|AGT|GAG|TCC|CTT|GGA|AAA|GGC|TAC|TCT|GAT|GGA|GGG| 510|
|His|Ser|Asn|Ala|Ser|Glu|Ser|Leu|Gly|Lys|Gly|Tyr|Ser|Asp|Gly|Gly| |
| |25| | | | |30| | | | |35| | | | | |
|TGC|TAC|GAG|CAA|CTT|TTT|GTC|TCT|CCT|GAG|GTG|TTT|GTG|ACT|CTG|GGT| 558|
|Cys|Tyr|Glu|Gln|Leu|Phe|Val|Ser|Pro|Glu|Val|Phe|Val|Thr|Leu|Gly| |
|40| | | | |45| | | | |50| | | | |55| |
|GTG|ATC|AGC|TTG|TTG|GAG|AAT|ATC|TTA|GTG|ATT|GTG|GCA|ATA|GCC|AAG| 606|
|Val|Ile|Ser|Leu|Leu|Glu|Asn|Ile|Leu|Val|Ile|Val|Ala|Ile|Ala|Lys| |
| | | | | |60| | | | |65| | | | |70| |
|AAC|AAG|AAT|CTG|CAT|TCA|CCC|ATG|TAC|TTT|TTC|ATC|TGC|AGC|TTG|GCT| 654|
|Asn|Lys|Asn|Leu|His|Ser|Pro|Met|Tyr|Phe|Phe|Ile|Cys|Ser|Leu|Ala| |
| | | | |75| | | | |80| | | | |85| | |
|GTG|GCT|GAT|ATG|CTG|GTG|AGC|GTT|TCA|AAT|GGA|TCA|GAA|ACC|ATT|ATC| 702|
|Val|Ala|Asp|Met|Leu|Val|Ser|Val|Ser|Asn|Gly|Ser|Glu|Thr|Ile|Ile| |
| | | |90| | | | |95| | | | |100| | | |
|ATC|ACC|CTA|TTA|AAC|AGT|ACA|GAT|ACG|GAT|GCA|CAG|AGT|TTC|ACA|GTG| 750|
|Ile|Thr|Leu|Leu|Asn|Ser|Thr|Asp|Thr|Asp|Ala|Gln|Ser|Phe|Thr|Val| |
| | |105| | | | |110| | | | |115| | | | |
|AAT|ATT|GAT|AAT|GTC|ATT|GAC|TCG|GTG|ATC|TGT|AGC|TCC|TTG|CTT|GCA| 798|
|Asn|Ile|Asp|Asn|Val|Ile|Asp|Ser|Val|Ile|Cys|Ser|Ser|Leu|Leu|Ala| |
|120| | | | |125| | | | |130| | | | |135| |
|TCC|ATT|TGC|AGC|CTG|CTT|TCA|ATT|GCA|GTG|GAC|AGG|TAC|TTT|ACT|ATC| 846|
|Ser|Ile|Cys|Ser|Leu|Leu|Ser|Ile|Ala|Val|Asp|Arg|Tyr|Phe|Thr|Ile| |
| | | | |140| | | | |145| | | | |150| | |
|TTC|TAT|GCT|CTC|CAG|TAC|CAT|AAC|ATT|ATG|ACA|GTT|AAG|CGG|GTT|GGG| 894|
|Phe|Tyr|Ala|Leu|Gln|Tyr|His|Asn|Ile|Met|Thr|Val|Lys|Arg|Val|Gly| |
| | | |155| | | | |160| | | | |165| | | |
|ATC|AGC|ATA|AGT|TGT|ATC|TGG|GCA|GCT|TGC|ACG|GTT|TCA|GGC|ATT|TTG| 942|
|Ile|Ser|Ile|Ser|Cys|Ile|Trp|Ala|Ala|Cys|Thr|Val|Ser|Gly|Ile|Leu| |
| | |170| | | | |175| | | | |180| | | | |

FIG. 6B

```
TTC ATC ATT TAC TCA GAT AGT AGT GCT GTC ATC ATC TGC CTC ATC ACC        990
Phe Ile Ile Tyr Ser Asp Ser Ser Ala Val Ile Ile Cys Leu Ile Thr
    185             190                 195

ATG TTC TTC ACC ATG CTG GCT CTC ATG GCT TCT CTC TAT GTC CAC CTG       1038
Met Phe Phe Thr Met Leu Ala Leu Met Ala Ser Leu Tyr Val His Leu
200             205                 210                 215

TTC CTG ATG GCC AGG CTT CAC ATT AAG AGG ATT GCT GTC CTC CCC GGC       1086
Phe Leu Met Ala Arg Leu His Ile Lys Arg Ile Ala Val Leu Pro Gly
                220                 225                 230

ACT GGT GCC ATC CGC CAA GGT GCC AAT ATG AAG GGA GCG ATT ACC TTG       1134
Thr Gly Ala Ile Arg Gln Gly Ala Asn Met Lys Gly Ala Ile Thr Leu
            235                 240                 245

ACC ATC CTG ATT GGC GTC TTT GTT GTC TGC TGG GCC CCA TTC TTC CTC       1182
Thr Ile Leu Ile Gly Val Phe Val Val Cys Trp Ala Pro Phe Phe Leu
        250                 255                 260

CAC TTA ATA TTC TAC ATC TCT TGT CCT CAG AAT CCA TAT TGT GTG TGC       1230
His Leu Ile Phe Tyr Ile Ser Cys Pro Gln Asn Pro Tyr Cys Val Cys
    265                 270                 275

TTC ATG TCT CAC TTT AAC TTG TAT CTC ATA CTG ATC ATG TGT AAT TCA       1278
Phe Met Ser His Phe Asn Leu Tyr Leu Ile Leu Ile Met Cys Asn Ser
280             285                 290                 295

ATC ATC GAT CCT CTG ATT TAT GCA CTC CGG AGT CAA GAA CTG AGG AAA       1326
Ile Ile Asp Pro Leu Ile Tyr Ala Leu Arg Ser Gln Glu Leu Arg Lys
                300                 305                 310

ACC TTC AAA GAG ATC ATC TCT TCC TAT CCC CTG GGA GGC CTT TGT GAC       1374
Thr Phe Lys Glu Ile Ile Ser Ser Tyr Pro Leu Gly Gly Leu Cys Asp
            315                 320                 325

TTG TCT AGC AGA TAT TAAATGGGGA CAGAGCACGC AATATAGGAA CATCCATAAG       1429
Leu Ser Ser Arg Tyr
                330

AGACTTTTTC ACTCTTACCC TACCTGAATA TTCTACTTCT GCAACAGCTT TCTCTTCCGT     1489

GTAGGGTACT GGTTGAGATA TCCATTGTGT AAATTTAAGC CTATGATTTT TAATGAGAAA     1549

AAATGCCCAG TCTCTGTATT ATTTCCAATC TCATGCTACT TTTTTGGCCA TAAAATATGA     1609

ATCTATGTTA TAGGTTGTAG GCACTGTGGA TTTACAAAAA GAAAAGTCCT TATTAAAAGC     1669

```
ATG AAC TCC TCC TCC ACC CTG ACT GTA TTG AAT CTT ACC CTG AAC GCC          48
Met Asn Ser Ser Ser Thr Leu Thr Val Leu Asn Leu Thr Leu Asn Ala
 1               5                  10                  15

TCA GAG GAT GGC ATT TTA GGA TCA AAT GTC AAG AAC AAG TCT TTG GCC          96
Ser Glu Asp Gly Ile Leu Gly Ser Asn Val Lys Asn Lys Ser Leu Ala
                 20                  25                  30

TGT GAA GAA ATG GGC ATT GCC GTG GAG GTG TTC CTG ACC CTG GGT CTC         144
Cys Glu Glu Met Gly Ile Ala Val Glu Val Phe Leu Thr Leu Gly Leu
             35                  40                  45

GTC AGC CTC TTA GAG AAC ATC CTG GTC ATT GGG GCC ATA GTA AAG AAC         192
Val Ser Leu Leu Glu Asn Ile Leu Val Ile Gly Ala Ile Val Lys Asn
         50                  55                  60

AAA AAC CTG CAC TCA CCC ATG TAC TTC TTT GTG GGC AGC TTA GCC GTG         240
Lys Asn Leu His Ser Pro Met Tyr Phe Phe Val Gly Ser Leu Ala Val
 65                  70                  75                  80

GCC GAC ATG CTG GTG AGC ATG TCC AAT GCC TGG GAG ACT GTC ACC ATA         288
Ala Asp Met Leu Val Ser Met Ser Asn Ala Trp Glu Thr Val Thr Ile
                 85                  90                  95

TAC TTG CTA AAT AAT AAA CAC CTG GTG ATA GCC GAC ACC TTT GTG CGA         336
Tyr Leu Leu Asn Asn Lys His Leu Val Ile Ala Asp Thr Phe Val Arg
            100                 105                 110

CAC ATC GAC AAC GTG TTC GAC TCC ATG ATC TGC ATC TCT GTG GTG GCC         384
His Ile Asp Asn Val Phe Asp Ser Met Ile Cys Ile Ser Val Val Ala
            115                 120                 125

TCG ATG TGC AGT TTG CTG GCC ATT GCG GTG GAT AGG TAC ATC ACC ATC         432
Ser Met Cys Ser Leu Leu Ala Ile Ala Val Asp Arg Tyr Ile Thr Ile
130                 135                 140

TTC TAT GCC TTG CGC TAC CAC CAC ATC ATG ACC GCG AGG CGC TCG GGG         480
Phe Tyr Ala Leu Arg Tyr His His Ile Met Thr Ala Arg Arg Ser Gly
145                 150                 155                 160

GTG ATC ATC GCC TGC ATT TGG ACC TTC TGC ATA AGC TGC GGC ATT GTT         528
Val Ile Ile Ala Cys Ile Trp Thr Phe Cys Ile Ser Cys Gly Ile Val
                165                 170                 175

TTC ATC ATC TAC TAT GAG TCC AAG TAT GTG ATC ATT TGC CTC ATC TCC         576
Phe Ile Ile Tyr Tyr Glu Ser Lys Tyr Val Ile Ile Cys Leu Ile Ser
            180                 185                 190

ATG TTC TTC ACC ATG CTG TTC TTC ATG GTG TCT CTG TAT ATA CAC ATG         624
Met Phe Phe Thr Met Leu Phe Phe Met Val Ser Leu Tyr Ile His Met
        195                 200                 205

TTC CTC CTG GCC CGG AAC CAT GTC AAG CGG ATA GCA GCT TCC CCC AGA         672
Phe Leu Leu Ala Arg Asn His Val Lys Arg Ile Ala Ala Ser Pro Arg
210                 215                 220

TAC AAC TCC GTG AGG CAA AGG ACC AGC ATG AAG GGG GCT ATT ACC CTC         720
Tyr Asn Ser Val Arg Gln Arg Thr Ser Met Lys Gly Ala Ile Thr Leu
225                 230                 235                 240
```

FIG. 7B

```
ACC ATG CTA CTG GGG ATT TTC ATT GTC TGC TGG TCT CCC TTC TTT CTT      768
Thr Met Leu Leu Gly Ile Phe Ile Val Cys Trp Ser Pro Phe Phe Leu
            245                 250                 255

CAC CTT ATC TTA ATG ATC TCC TGC CCT CAG AAC GTC TAC TGC TCT TGC      816
His Leu Ile Leu Met Ile Ser Cys Pro Gln Asn Val Tyr Cys Ser Cys
            260                 265                 270

TTT ATG TCT TAC TTC AAC ATG TAC CTT ATA CTC ATC ATG TGC AAC TCC      864
Phe Met Ser Tyr Phe Asn Met Tyr Leu Ile Leu Ile Met Cys Asn Ser
            275                 280                 285

GTG ATC GAT CCT CTC ATC TAC GCC CTC CGC AGC CAA GAG ATG CGG AGG      912
Val Ile Asp Pro Leu Ile Tyr Ala Leu Arg Ser Gln Glu Met Arg Arg
            290                 295                 300

ACC TTT AAG GAG ATC GTC TGT TGT CAC GGA TTC CGG CGA CCT TGT AGG      960
Thr Phe Lys Glu Ile Val Cys Cys His Gly Phe Arg Arg Pro Cys Arg
305                 310                 315                 320

CTC CTT GGC GGG TAT TAA                                              978
Leu Leu Gly Gly Tyr  *
            325
```

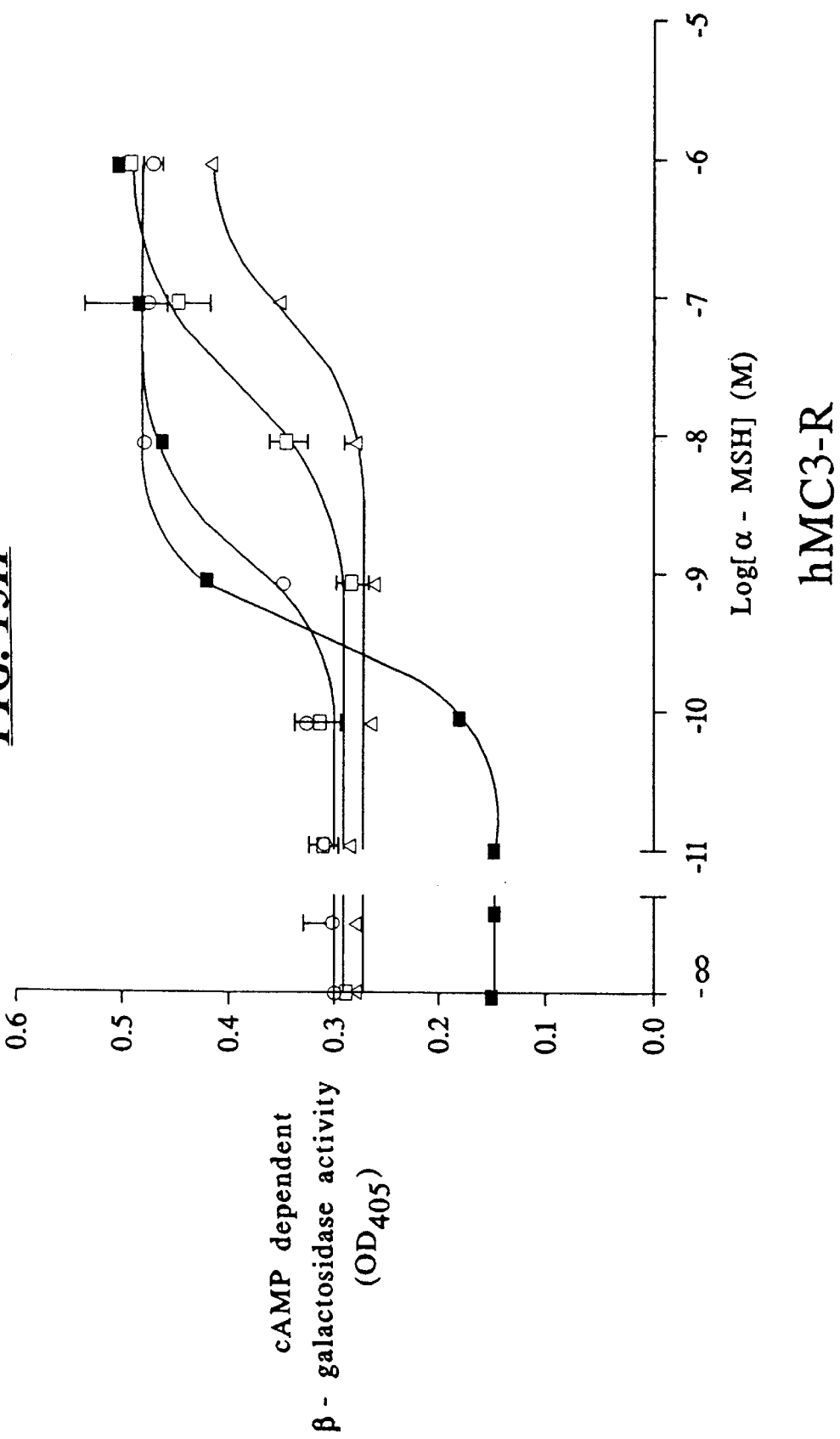

*FIG. 19A*
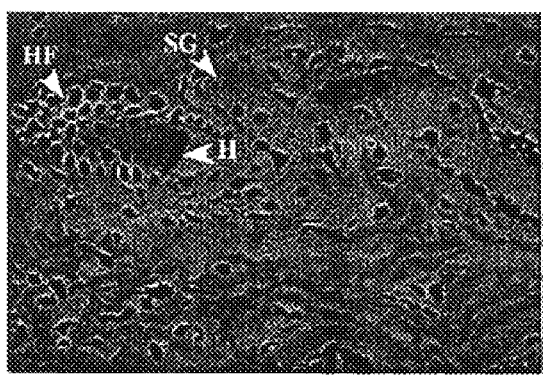
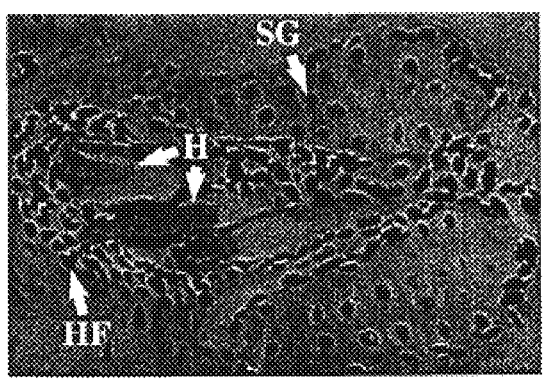
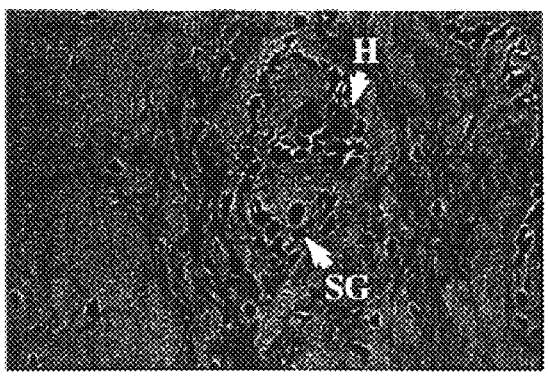
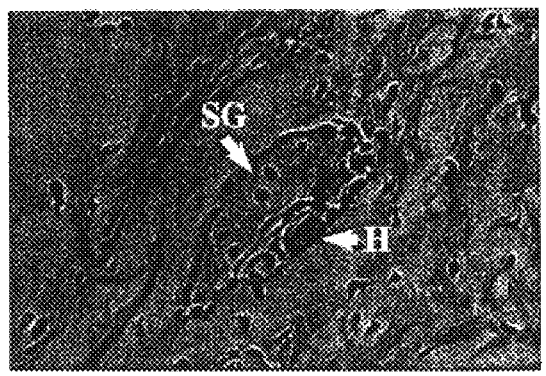

MC5-R Expression in Mouse Tissues

MC5-R coding
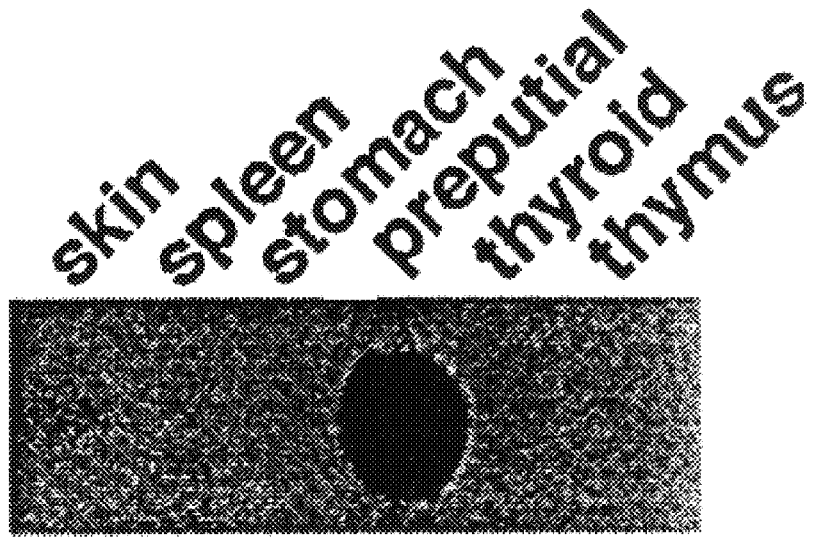
18S rRNA
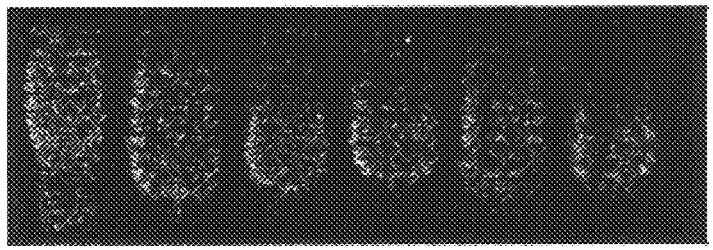
*FIG. 19D*

MC5R
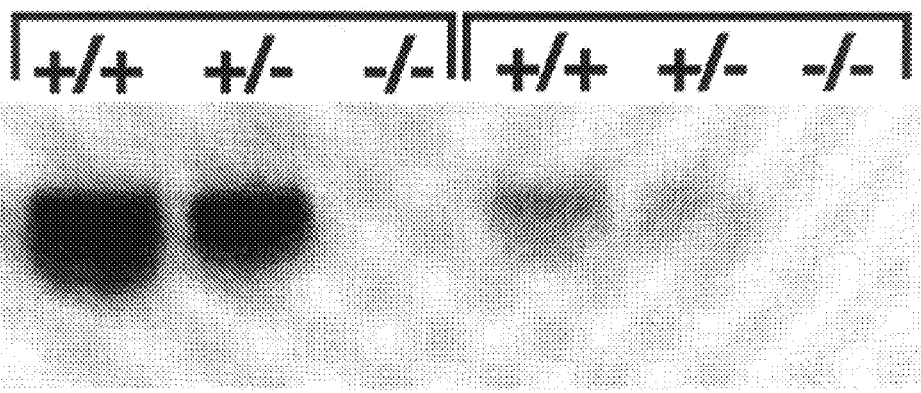
β-actin
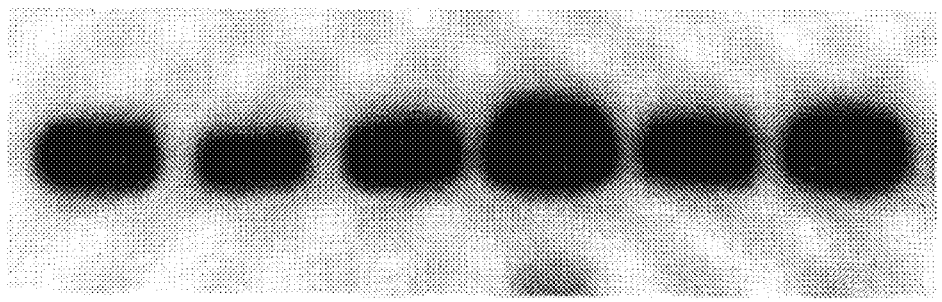
*FIG. 19E*

Dose Response of ACTH-stimulated Protein Secretion

Absorbance Spectrum of Harderian Gland Extracts

MAMMALIAN MELANOCORTIN RECEPTORS AND USES

This application is a continuation of U.S. Ser. No. 60/050,063, filed Jun. 13, 1997, which is a continuation-in-part of U.S. Ser. No. 08/706,281, filed Sep. 4, 1996 now U.S. Pat. No. 6,100,048, which is a continuation-in-part of U.S. Ser. No. 08/466,906, filed Jun. 6, 1995, now U.S. Pat. No. 5,849,871, which is a divisional of U.S. Ser. No. 07/886,979, filed Apr. 10, 1992, now U.S. Pat. No. 5,532,347, issued Jul. 2, 1996. This application is also a continuation-in-part of U.S. Ser. No. 08/478,992, filed Jun. 7, 1995, now U.S. Pat. No. 5,773,229, which is a divisional of U.S. Ser. No. 08/077,673, filed Jun. 15, 1993, which is a divisional of U.S. Ser. No. 07/866,560, filed Apr. 10, 1992, now U.S. Pat. No. 5,280,112, issued Jan. 18, 1994. This application is also a continuation-in-part of U.S. Ser. No. 08/044,812, filed Apr. 8, 1993 now U.S. Pat. No. 5,837,521.

This invention was made with government support under P01HD30236 by the National Institutes of Health. The government has certain rights in the invention.

BACKGROUND OF THE INVENTION

1. Field of the Invention

This invention relates to melanocortin receptors from mammalian species and the genes corresponding to such receptors. Specifically, the invention relates to the use of mammalian melanocortin receptors for the development of naturally-occurring and synthetic agonists and antagonists specific for a mammalian melanocortin receptor, and the use of such agonists and antagonists for treatment and alleviation of dysfunction and disease. Specifically, the invention relates to development of naturally-occurring and synthetic agonists and antagonists specific for a mammalian melanocortin receptor termed MC5-R (see U.S. Pat. No. 5,622,860, incorporated by reference). Such naturally-occurring and synthetic agonists and antagonists specific for the MC5-R receptor are provided for the treatment, control, amelioration and alleviation of diseases, and dysfunctional and abnormal states related to thermoregulatory disorders, as well as other diseases relating to exocrine gland disorders, including lacrimal gland dysfunction and sebaceous gland disorders including acne and other skin problems. Also provided by the invention are nucleic acids, constructs, vectors and methods for producing an animal having homozygous disruption of both endogenous MC5-R melanocortin receptors, preferably a rodent and most preferably a mouse. Such rodents, termed "gene knockout"rodents in the art, are also advantageously provided.

2. Background of the Invention

The proopiomelanocortin (POMC) gene product is processed to produce a large number of biologically active peptides. Two of these peptides, α-melanocyte stimulating hormone (αMSH), and adrenocorticotropic hormone (ACTH) have well-understood roles in control of melanocyte and adrenocortical function, respectively. Both of these hormones are also found in a variety of forms with unknown functions, for example, γ-melanocyte stimulating hormone (γMSH), which has little or no ability to stimulate pigmentation (Ling et al., 1979, Life Sci. 25:1773–1780; Slominski et al., 1992, Life Sci. 50:1103–1108). A melanocortin receptor gene specific for each of the αMSH, ACTH and γMSH hormones has been discovered by some of the present inventors (see U.S. Pat. Nos. 5,280,112 and 5,532,347 and U.S. application Ser. No. 08/044,812, incorporated by reference herein). In addition, two other melanocortin receptor genes have been discovered by some of the present inventors (see Lu et al, 1994, Nature 371:799–802, Mountjoy et al., 1994, Molec. Endocrinol. 8:1298–1308) and others (see U.S. Pat. No. 5,622,860; Gantz et al., 1993, J Biol. Chem. 268:15174–15179 and Labbe et al., 1994, Biochem. 33:4543–4549). Thus far, the biological activities of the melanocortin peptides appear to be mediated by a family of five G protein coupled receptors (see Cone, 1996 for a review).

Along with the well-recognized activities of αMSH in melanocytes and ACTH in adrenal and pituitary glands, the melanocortin peptides also have a diverse array of biological activities in other tissues, including the brain and immune system, and bind to specific receptors in these tissues with a distinct pharmacology (see Hanneman et al., in Peptide Hormone as Prohormones, G. Martinez, ed. (Ellis Horwood Ltd.: Chichester, UK) pp. 53–82; DeWied & Jolles, 1982, Physiol. Rev. 62:976–1059 for reviews). For example, POMC neurons are present in only two regions of the brain, the arcuate nucleus of the hypothalamus, and the nucleus of the solitary tract of the brain stem. Neurons from both sites project to a number of hypothalamic nuclei, including the paraventricular nucleus, lateral hypothalamic area, and ventromedial hypothalamic nucleus. A complete understanding of these peptides and their diverse biological activities requires the isolation and characterization of their corresponding receptors. Some biochemical studies have been reported in the prior art.

Shimuze, 1985, Yale J. Biol. Med. 58:561–570 discusses the physiology of melanocyte stimulating hormone.

Tatro & Reichlin, 1987, Endocrinology 121:1900–1907 disclose that MSH receptors are widely distributed in rodent tissues.

Sola et al., 1989, J Biol. Chem. 264:14277–14280 disclose the molecular weight characterization of mouse and human MSH receptors linked to radioactively and photoaffinity labeled MSH analogues.

Siegrist et al., 1991, J Receptor Res. 11:323–331 disclose the quantification of receptors on mouse melanoma tissue by receptor autoradiography.

Cone & Mountjoy, U.S. Pat. No. 5,532,347, issued Jul. 2, 1996, disclose the isolation of human and mouse α-MSH receptor genes and uses thereof (incorporated herein by reference).

Cone & Mountjoy, U.S. Pat. No. 5,280,112, issued Jan. 18, 1994, disclose the isolation of human and bovine ACTH receptor genes and uses thereof (incorporated herein by reference).

Mountjoy et al., 1992, Science 257:1248–1251 disclose the isolation of cDNAs encoding mammalian ACTH and MSH receptor proteins.

Cone et al., U.S. Ser. No. 08/044,812, filed Apr. 8, 1993, disclose the isolation of rat γ-MSH receptor genes and uses thereof (incorporated herein by reference).

The distribution of expression of the known melanocortin receptors has largely fit expectations regarding the known biological activities of the melanocortin peptide ligands encoded by the POMC gene. The MC1-R, or classical MSH receptor, is expressed almost exclusively in melanocytes (Chhajlani and Wikberg, 1992, FEBS Lett. 309:417–420; Mountjoy et al., 1992, ibid.), where it regulates melanin synthesis. The MC2-R, or classical ACTH receptor, is expressed primarily in the adrenal cortex (Mountjoy et al., 1992, ibid.), where it regulates adrenocortical steroidogenesis (although this receptor is also expressed in adipocytes, explaining the ability of ACTH to stimulate lipolysis). The MC3-R and MC4-R are expressed mainly in the central nervous system in regions that are well-correlated with presumptive terminal fields originating from the two groups of POMC cell bodies in the arcuate nucleus of the hypothalamus and the nucleus of the solitary tract of the brainstem (Mountjoy et al., 1994, ibid.; Roselli-Rehfuss et al., 1993, *Proc. Natl. Acad. Sci. USA* 90:8856–8860). Recently, it has been shown that MC3-R and MC4-R regulate feeding behavior and metabolism (Fan et al., 1997, *Nature* 385:165–168; Huszar et al., 1997, *Cell* 88:131–141), grooming behavior (Adan et al., 1994), body temperatures (Tatro et al., 1990, *Cancer Res.* 50:1237–1242), and cardiovascular tone (Li et al., 1996, *J. Neurosci.* 16:5182–5188); see also U.S. patent application Ser. No. 08/706,281, filed Sep. 4, 1996 and incorporated by reference herein.

Numerous peripheral effects of POMC peptides have been reported. For example, removal of the neurointermediate lobe of the pituitary (which produces the POMC peptides) was demonstrated to decrease sebaceous lipid production (Thody and Shuster, 1973, *Nature* 245:207–209). The reduction was fully restored by concomitant A-MSH and androgen administration (Ebling et al., 1975, *J. Endocrinol.* 66:407–412). The lipid content of the preputial gland (a specialized sebaceous gland implicated in pheromone production in rodents; Bronson and Caroom, 1971, *J. Reprod. Fertil.* 25:279–282; Chipman and Alberecht, 1974, *J. Reprod. Fertil.* 38:91–96; Orsulak and Gawienowski, 1972, *Biol. Reproduc.* 6:219–223) has been shown to be stimulated by α-MSH. Injection of α-MSH has been shown to elicit several behavioral changes in the conspecific animals, including altered sexual attraction in male rats (Thody and Wilson, 1983, *Physiol. Behav.* 31:67–72), and modified aggression in male mice due to olfactory cues presumably from the preputial gland (Nowell et al., 1980, *Physiol. Behav.* 24:5–9). High affinity ACTH and MSH binding sites have also been reported to regulate lipolysis in adipocytes (Oelofsen and Ramachandran, 1983, *Arch. Biochem. Biophys.* 225:414–421; Ramachandran et al., 1976, *Biochim. Biophys. Acta* 428:339–346) and protein secretion in the lacrimal gland (Jahn, 1982, *Eur. J. Biochem.* 126:623–629; Tatro and Reichlin, 1987, ibid.).

The systemic effects of pituitary-derived peptides have been attributed to ACTH-mediated adrenocortical glucocorticoid production. The primary role of serum-derived ACTH is the regulation of adrenocortical glucocorticoid production. In response to physical or psychological stress, hypothalamic corticotropin releasing hormone stimulates the production of ACTH by anterior pituitary cells. Serum ACTH is elevated 3–5 fold, producing a subsequent 10–100 fold elevation in circulating cortisol or corticosterone. Glucocorticoids then support the response to stress, serving to stimulate hepatic gluconeogenesis and elevate blood glucose, and mobilize amino acid stores from muscle and fatty acids from adipose tissue. Glucocorticoids also have an important role in the resolution of immune responses, acting on numerous cell types to reduce inflammation.

One of the melanocortin receptors, termed MC-5, has been found by the present inventors to be widely-distributed in peripheral tissues, raising the possibility of non-steroidally mediated systemic effects of MSH/ACTH peptides. This receptor has been cloned from human, mouse, rat, and sheep, and is highly conserved, being approximately 80% identical amongst the mammals. Furthermore, the MC5-R is highly responsive to both α-MSH and ACTH, as determined by $EC_{50}$ values for elevation of intracellular cAMP or activation of adenylate cyclase. Further investigation by the present inventors has demonstrated high levels of MC5-R gene expression in multiple exocrine tissues, including the Harderian, preputial, lacrimal, and sebaceous glands in rodents. The MC5-R has also been shown to be required for the production of porphyrins by the Harderian gland, and physiological concentrations of ACTH were demonstrated to regulate protein secretion by the lacrimal gland via binding to MC5-R.

The present inventors have now produced a mouse by targeted disruption of the MC5-R gene with a severe defect in water repulsion and thermoregulation due to decreased production of sebaceous lipids. Analysis of these mice revealed a requirement for MC5-R gene expression in multiple exocrine glands in vivo for the production of a diverse set of products, including lipids, proteins, and porphyrins, and suggested the existence of a coordinated system for the regulation of exocrine gland function by melanocortin peptides, related to thermoregulatory homeostasis, tear production and the production of skin and hair oils. Thus, these results produced for the first time in the art a need for the development of MC5-R receptor agonists and antagonists for the regulation of such biological processes and for the alleviation of diseases, dysfunctions and abnormal conditions related to exocrine gland function.

SUMMARY OF THE INVENTION

The present invention relates to the cloning, expression and functional characterization of mammalian melanocortin receptor genes, particularly mammalian MC5-R receptor genes, and most preferably human MC5-R receptor genes. The invention provides methods for identifying and producing naturally-occurring and synthetic agonists and antagonists specific for the MC5-R receptor gene for the treatment, control, amelioration and alleviation of diseases, dysfunctional and abnormal states related to thermoregulatory disorders and diseases, and for exocrine gland-related disorders, including lacrimal gland dysfunction and sebaceous gland disorders including acne and other skin problems. Also provided by the invention are nucleic acids, constructs, vectors and methods for producing an animal having homozygous disruption of both endogenous MC-5 melanocortin receptors, preferably a rodent and most preferably a mouse. Such rodents, termed "gene knockout" rodents in the art, are also advantageously provided.

In a first aspect is provided a method for assaying any test compound for binding to a mammalian melanocortin receptor. This method of the invention comprises the steps of:

(a) providing a first primary eukaryotic cell culture derived from a tissue in an animal wherein the melanocortin receptor is expressed in the tissue from the animal;

(b) providing a second primary eukaryotic cell culture derived from the tissue of subpart (a), but derived from an animal carrying a disrupted genetic sequence encoding the melanocortin receptor wherein the disrupted allele cannot produce the melanocortin receptor in the cell;

(c) contacting the eukaryotic cell culture of subpart (a) and the eukaryotic cell culture of subpart (b) with the test compound;

(d) detecting binding of the test compound to the cells of the eukaryotic cell culture of subpart (a) and the eukaryotic cell culture of subpart (b); and (e) comparing binding of the test compound to the cells of the eukaryotic cell culture of subpart (a) with binding of the test compound to cells of the eukaryotic cell culture of subpart (b).

In a preferred embodiment, the melanocortin receptor is MC5-R. In a preferred embodiment, the test compound is detectably labeled, most preferably with a radioisotope, a fluorescent label, a hapten, an enzymatic label or an antigenic label. In other preferred embodiments of the invention, detection of binding of the test compound is accomplished by detecting the production of a metabolite, most preferably cyclic adenosine monophosphate (cAMP) that is produced by the cell upon binding of the test compound to the melanocortin receptor. The invention also provides additional methods wherein the eukaryotic cell cultures of subpart (a) or subpart (b) further comprise a recombinant expression construct encoding a cAMP responsive element (CRE) transcription factor binding site operatively linked to a nucleic acid sequence encoding a protein that produces a detectable metabolite. In these embodiments, binding of the test compound to the melanocortin receptor produces expression of the protein that acts on a substrate in the cell to produce a detectable metabolite. Preferred embodiments of such aspects of the invention include cells comprising a recombinant expression construct encoding β-galactosidase, wherein expression of β-galactosidase is induced in the cell upon binding of the test compound to the melanocortin receptor.

Additionally, it is preferred that the cells of subpart (b) comprise a genetically disrupted melanocortin receptor gene that is in a heterozygous condition and most preferably in a homozygous condition.

In another aspect of the methods of the invention, the following additional steps are included:

(f) contacting the cells of the eukaryotic cell culture of subparts (a) and (b) with a detectably-labeled, previously-characterized melanocortin receptor agonist or antagonist prior to contacting the eukaryotic cell cultures with the test compound;

(g) comparing binding the detectably labeled melanocortin agonist or antagonist in the presence and absence of the test compound for each of the eukaryotic cell cultures of subparts (a) and (b); and (h) comparing inhibition of binding of the detectably-labeled melanocortin receptor agonist of antagonist by the test compound to the cells of the eukaryotic cell culture of subpart (a) with inhibition of binding of the detectably-labeled melanocortin receptor agonist of antagonist by the test compound to cells of the eukaryotic cell culture of subpart (b).

In a preferred embodiment, the melanocortin receptor is MC5-R. In preferred embodiments, the detectably-labeled, previously-characterized melanocortin receptor agonist or antagonist is detectably labeled with a radioisotope, a fluorescent label, a hapten, an enzymatic label or an antigenic label. In other preferred embodiments of the invention, detection of binding of the test compound is accomplished by detecting the production of a metabolite, most preferably cAMP that is produced by the cell upon binding of the test compound to the melanocortin receptor. The invention also provides additional methods wherein the eukaryotic cell cultures of subpart (a) or subpart (b) further comprise a recombinant expression construct encoding a CRE transcription factor binding site operatively linked to a nucleic acid sequence encoding a protein that produces a detectable metabolite. In these embodiments, binding of the test compound to the melanocortin receptor produces expression of the protein that acts on a substrate in the cell to produce a detectable metabolite. Preferred embodiments of such aspects of the invention include cells comprising a recombinant expression construct encoding P-galactosidase, wherein expression of β-galactosidase is induced in the cell upon binding of the test compound to the melanocortin receptor.

In these aspects the invention it is also preferred that the cells of subpart (b) comprise a genetically disrupted melanocortin receptor gene that is in a heterozygous condition and most preferably in a homozygous condition.

The invention also provides a recombinant expression construct comprising a portion of a nucleic acid encoding a melanocortin receptor gene, covalently linked to a nucleic acid comprising 5' or 3' untranslated sequence flanking the melanocortin receptor gene, a first selectable marker covalently linked immediately adjacent to the portion of the nucleic acid encoding the melanocortin receptor gene, and a second selectable marker covalently linked distal to the portion of the nucleic acid encoding the melanocortin receptor gene, wherein introduction of the recombinant expression construct into a eukaryotic cell produces a cell having a genetically disrupted endogenous melanocortin receptor gene by homologous recombination of the recombinant expression construct into the endogenous melanocortin receptor gene. In preferred embodiments, the melanocortin gene is MC5-R, the first selectable marker comprises a nucleic acid encoding a neo, $hyg^R$, or gpt gene and the second selectable marker comprises a nucleic acid encoding a herpesvirus thymidine kinase gene.

The invention also provides eukaryotic cells transformed with the recombinant expression constructs of the invention, most preferably embryonic stem cells, wherein the cells comprise a genetically disrupted endogenous melanocortin receptor gene by homologous recombination of the recombinant expression construct into the endogenous melanocortin receptor gene.

Also provided are transgenic animals comprising a cell in a tissue of the animal, most preferably a germ cell, wherein an endogenous melanocortin receptor gene is disrupted by homologous recombination of a recombinant expression construct of the invention into the endogenous melanocortin receptor gene. In preferred embodiments, the disrupted endogenous melanocortin receptor gene is MC5-R, preferably in a heterozygous condition and most preferably in a homozygous condition.

The invention also provides methods for assaying a test compound for binding to a mammalian melanocortin receptor the following steps:

(a) providing a cell panel comprising a first mammalian cell comprising a recombinant expression construct encoding a mammalian melanocortin receptor that is the MC 1-R receptor, a second mammalian cell comprising a recombinant expression construct encoding a mammalian melanocortin receptor that is the MC2-R receptor, a third mammalian cell comprising a recombinant expression construct encoding a mammalian melanocortin receptor that is the MC3-R receptor, a fourth mammalian cell comprising a recombinant expression construct encoding a mammalian melanocortin receptor that is the MC4-R receptor, wherein each mammalian cell expresses the melanocortin receptor encoded by the recombinant expression construct comprising the cell, and a fifth mammalian cell culture comprising a primary eukaryotic cell culture derived from a tissue in an animal expressing a mammalian melanocortin receptor that is the MC5-R receptor;

(b) contacting each of the cells of the panel with an agonist or antagonist of the mammalian melanocortin receptor in an amount sufficient to produce a detectable metabolite in the cells that bind the agonist or antagonist, in the presence or absence of a test compound; and (c) detecting the amount of the metabolite produced in each cell in the panel in the presence of the test compound with the amount of the metabolite produced in each cell in the absence of each test compound.

Panels of cells according to subpart (a) are also provided by the invention.

The invention advantageously provides methods and reagents for detecting, characterizing and developing melanocortin receptor agonists and antagonists, most preferably MC5-R receptor agonists and antagonists, for producing pharmaceutical compositions for the alleviations of exocrine gland-related disorders, including but not limited to acne, other sebaceous gland skin disorders and diseases and lacrimal gland disorders such as "dry eye" condition. The production of mice homozygous for a genetically-disrupted melanocortin receptor, most preferably MC5-R receptor, enables the production of primary and immortalized cell and tissue cultures from such animals that can be used in comparison with similarly produced cultures from wild-type and heterozygous melanocortin disrupted mice for precise analysis and characterization of melanocortin receptor agonists and antagonists. The methods of the invention also enable the production of equivalent mice homozygous for genetically-disrupted melanocortin receptors of the other known melanocortin receptor types, and the use of such mice in cognate methods for developing agonist and antagonist compounds and pharmaceutical compositions specific for each of the known melanocortin receptors. In addition, the methods of the present invention can be used with any cell surface receptor, including additional and as yet uncharacterized melanocortin receptors.

Specific preferred embodiments of the present invention will become evident from the following more detailed description of certain preferred embodiments and the claims.

DESCRIPTION OF THE DRAWINGS

FIGS. 1A and 1B illustrate the nucleotide (SEQ ID No.: 3) and amino acid (SEQ ID No.: 4) sequence of the mouse melanocyte stimulating hormone receptor gene (MC1-R).

FIGS. 2A and 2B illustrate the nucleotide (SEQ ID No.: 5) and amino acid (SEQ ID No.: 6) sequence of the human melanocyte stimulating hormone receptor gene (MC 1-R).

FIGS. 3A and 3B illustrate the nucleotide (SEQ ID No.:7) and amino acid (SEQ ID No.:8) sequence of the human adrenocorticotropic hormone receptor gene (MC2-R).

FIGS. 4A and 4B illustrate the nucleotide (SEQ ID No.: 9) and amino acid (SEQ ID No.: 10) sequence of the bovine adrenocorticotropic hormone receptor gene (MC2-R).

FIGS. 5A and 5B illustrate the nucleotide (SEQ ID No.: 11) and amino acid (SEQ ID No.: 12) sequence of the rat melanocortin-3 receptor (MC3-R).

FIGS. 6A and 6B illustrate the nucleotide (SEQ ID No.:15) and amino acid (SEQ ID No.:16) sequence of the human melanocortin-4 receptor gene (MC4-R).

FIGS. 7A and 7B illustrate the nucleotide (SEQ ID No.: 17) and amino acid (SEQ ID No.: 18) sequence of the rat melanocortin-5 receptor gene (MC5-R).

FIGS. 15A through 15H illustrate the results of the β-galactosidase-coupled, colorimetric melanocortin receptor binding assay using cells expressing each of the MC1-R, MC3-R, MC4-R or MC5-R receptors and contacted with αMSH or a variety of αMSH analogues.

FIG. 18A illustrate that MC5-RKO mice dry more slowly after a 3 minute swim. The picture taken about 15 minutes after swimming in 32° C. water. The two wet mice on the left are MC5-RKO mice. The other two are wild-type mice. FIG. 18B shows impaired water repulsion in MC5-RKO mice. MC5-RKO mice absorb more water during the swim than wild-type controls. Removal of hair lipids with 5% SDS wash increases water absorption in wild-type mice. FIG. 18C shows that increased water absorption induces hypothermia in MC5-RKO mice and in shampooed wild-type mice. FIG. 18D shows MC5-RKO and shampooed wild-type mice exhibit hypothermia in cold air. Mice were put in 5–6° C. cold room without bedding in a Plexiglas cage. Colonic temperature was measured every 30 minutes. FIG. 18E shows reduced sebum production by 15–20% in MC5-RKO mice. FIG. 18F shows significant deficit in sterol ester lipids in the MC5-RKO mouse. Hair lipids are extracted as described in Example 5. Lipids were resolved in Silica Gel 60 plate (20×20 cm) with hexanes/benzenes (55:45, v/v). Each lane contained 150 µg of total lipids.

FIGS. 19A through 19E are in situ hybridization assays showing that MC5-R is highly abundant in exocrine glands and present at low levels in a number of other tissues. FIG. 19A shows that MC5-R is specifically expressed in sebaceous gland in the skin. Five µM sections were made from paraffin-embedded skin tissues. After proteinase K digestion and acetylation, the sections were probed with antisense (FIG. 19A, Panels A though C) or sense (FIG. 19A, Panel D) riboprobe of the deleted region in MC5-RKO mice. Hybridization of MC5-R was found in wild-type skin (FIG. 19A, Panels A and C) but not in MC5-RKO skin (FIG. 19A, Panel B). No hybridization was detected by sense probe of the same sequence in mild-type skin (FIG. 19A, Panel D).

FIG. 19B illustrates the results of northern analysis showing MC5-R mRNA is expressed at low levels in a number of neuronal and non-neuronal tissues. Forty µg of total RNA was loaded in each lane (10 µg for pituitary, thyroid adrenal).

FIG. 19C illustrates the results of northern analysis showing MC5-R mRNA is highly expressed in preputial, Harderian and lacrimal glands. Ten µg of total RNA is loaded in each lane.

FIG. 19D illustrates the results of northern analysis showing MC5-R mRNA levels in preputial gland are much higher than in the skin. Twenty ug of total RNA was loaded in each lane.

FIG. 19E illustrates the results of northern analysis showing MC5-R mRNA is not present in preputial and Harderian gland of MC5-RKO mice. Ten µg of total RNA was loaded in each lane. The membrane-bound RNA was probed with the 650 bp Apa I/Msc I MC5-R-derived fragment specifically deleted in MC5-RKO mice.

FIG. 20A shows that specific binding sites are present in plasma membrane of Harderian gland, preputial gland and lacrimal gland. The crude membranes were prepared as described in Example 5. The specific binding activity in different tissues does not necessarily represent the levels of expression, as the purity of the membrane preparation may be different between samples form different tissue.

FIG. 20B shows NDP-α-MSH binding is markedly decreased in the spinal cord of MC5-RKO mice.

FIG. 20C shows lack of α-MSH and NDP-α-MSH regulated cAMP production in preputial glands from MC5-RKO mice. Glands were excised and incubated with DMEM containing α-MSH (50 µM), NDP-α-MSH (100 µM), or the two combined. Twenty minutes later, the glands were snap frozen in liquid nitrogen and subsequently homogenized in 60% ethanol. After centrifugation, the cAMP supernatant was vacuum dried. The quantity of cAMP in each sample was determined by a cAMP RIA kit purchased from NEN.

FIG. 20D shows lack of α-MSH and NDP-α-MSH regulated cAMP production in Harderian glands from MC5-RKO mice.

FIG. 22A is a comparison of UV illuminated fluorescence between extracts from Harderian gland of individual MC5-RKO mice and wild-type or heterozygous controls. FIG. 22B is a comparison of porphyrins from a pair of Harderain gland by scanning spectrophotometry, wherein one-quarter of the total extracts from individual pairs of glands in 0.5 ml 0.25 N HCl was scanned. The two absorbance peaks at 402 and 550 nm are characteristics of porphyrins.

DETAILED DESCRIPTION OF THE PREFERRED EMBODIMENTS

Figure 8:
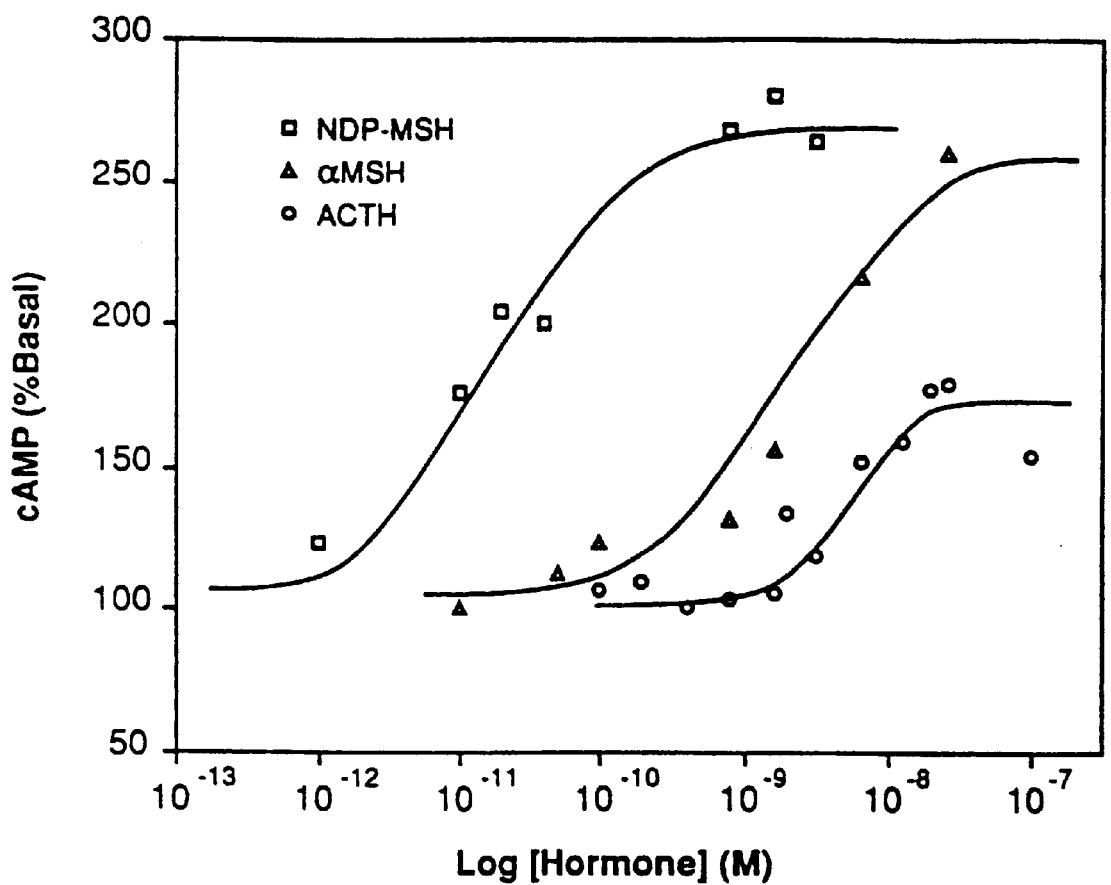
FIG. 8 shows a graph of intracellular cAMP accumulation resulting from melanocyte stimulating hormone receptor agonist binding in human 293 cells transfected with αMSH receptor-encoding recombinant expression construct.

The term "melanocortin receptor" as used herein reference to proteins having the biological activity of any of the disclosed melanocortin receptors, including the MC1-R (SEQ ID Nos.: 3, 4, 5 and 6, also disclosed in co-owned U.S. Pat. No. 5,532,347, incorporated by reference), MC2-R (ACTH; SEQ ID Nos.: 7, 8, 9 and 10, also disclosed in co-owned U.S. Pat. No. 5,554,729, incorporated by reference), MC3-R (SEQ ID Nos.: 11 and 12, also disclosed in co-owned U.S. Ser. No. 08/044,812, incorporated by reference), MC4-R (SEQ ID Nos.: 15 and 16) or MC5-R (SEQ ID Nos.: 17 and 18) receptors, as well as naturally-occurring and genetically-engineered allelic variations in these sequences. In particular, primary and immortalized cultures of mammalian cells expressing native melanocortin receptors, as well as mammalian cells produced as described herein by recombinant genetic techniques and expressing heterologous melanocortin receptors, are encompassed by this invention. For the purposes of this invention, the terms "native" and "endogenous" will be understood to describe melanocortin receptor gene expression in cells expressing the naturally-occurring melanocortin gene incorporated as part of the cells of chromosome and inherited without intervention by man. In contrast, the term "heterologous" or "genetically engineered" when applied to a melanocortin receptor gene will be understood to encompass melanocortin receptor genes and sequences introduced into a cell by genetic engineering or other means, thereby providing the cell with the capacity to express a hitherto unexpressed gene derived from another cell, and preferably a melanocortin receptor gene from a different mammalian species.

Cloned nucleic acid provided by the present invention may encode MC receptor proteins of any species of origin, including, for example, mouse, rat, rabbit, cat, and human, but preferably the nucleic acid provided by the invention encodes MC receptors of mammalian, most preferably rodent and human, origin.

The production of proteins such as the MC receptors from cloned genes by genetic engineering means is well known in this art. The discussion which follows is accordingly intended as an overview of this field, and is not intended to reflect the full state of the art.

DNA which encodes MC receptors may be obtained, in view of the instant disclosure, by chemical synthesis, by screening reverse transcripts of mRNA from appropriate cells or cell line cultures, by screening genomic libraries from appropriate cells, or by combinations of these procedures, as illustrated below. Screening of mRNA or genomic DNA may be carried out with oligonucleotide probes generated from the MC receptor gene sequence information provided herein. Probes may be labeled with a detectable group such as a fluorescent group, a radioactive atom or a chemiluminescent group in accordance with known procedures and used in conventional hybridization assays, as described in greater detail in the Examples below. In the alternative, MC receptor gene sequences may be obtained by use of the polymerase chain reaction (PCR) procedure, with the PCR oligonucleotide primers being produced from the MC receptor gene sequences provided herein. See U.S. Pat. Nos. 4,683,195 to Mullis et al. and 4,683,202 to Mullis.

MC receptor proteins may be synthesized in cells from tissues that endogenously express any particular melanocortin receptor species. In particular, primary and immortalized cells are derived from tissues and organs of a mammal to provide cultures of such cells for use with the methods of the invention as disclosed herein, using methods well known in the art. See *Tissue Culture*, Academic Press, Kruse & Patterson, editors (1973). Any primary or immortalized culture expressing an endogenous (as opposed to heterologous or genetically-engineered) melanocortin receptor can be used, provided such cells produce an amount of the melanocortin receptor protein that is detectable using receptor binding assays as described herein and known in the art.

Alternatively, host cells transformed with a recombinant expression construct comprising a nucleic acid encoding each of the receptors disclosed herein can be used to provide a homogeneous culture of MC receptor expressing cells. Recombinant expression constructs comprising the MC receptor coding sequences as disclosed herein can also be comprised of a vector that is a replicable DNA construct. Vectors are used herein either to amplify DNA encoding an MC receptor and/or to express DNA which encodes an MC receptor. For the purposes of this invention, a recombinant expression construct is a replicable DNA construct in which a DNA sequence encoding an MC receptor is operably linked to suitable control sequences capable of effecting the expression of the receptor in a suitable host cell. The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation. Amplification vectors do not require expression control domains. All that is needed is the ability to replicate in a host, usually conferred by an origin of replication, and a selection gene to facilitate recognition of transformants. See, Sambrook et al., 1990, *Molecular Cloning: A Laboratory Manual* (Cold Spring Harbor Press: New York).

Also specifically provided by the invention are reporter expression constructs comprising a nucleic acid encoding a protein capable of expressing a detectable phenotype, such as the production of a detectable reporter molecule, in a cell expressing the construct. Such constructs can be used for producing recombinant mammalian cell lines in which the reporter construct is stably expressed. Most preferably, however, the reporter construct is provided and used to induce transient expression over an experimental period of from about 18 to 96 hrs in which detection of the reporter protein produced detectable metabolite comprises an assay. Such reporter expression constructs are also provided wherein induction of expression of the reporter construct is controlled by a responsive element operatively linked to the coding sequence of the reporter protein, so that expression is induced only upon proper stimulation of the responsive element. Exemplary of such a responsive element is a cAMP responsive element (CRE), which induces expression of the reporter protein as a result of an increase in intracellular cAMP concentration. In the context of the present invention, such a stimulus is associated with melanocortin receptor binding, so that a reporter construct comprising one or more CREs is induced to express the reporter protein upon binding of a receptor agonist to a MC receptor in a recombinantly transformed mammalian cell. Preferably, such reporter gene constructs are genetically engineered into cells expressing a melanocortin receptor of the invention, either heterologous or endogenous as these terms have been defined herein, thereby providing a recombinant cell capable of producing a detectable product upon agonist or antagonist receptor binding to the melanocortin receptor expressed by the cell.

Vectors useful for practicing the present invention include plasmids, viruses (including phage), retroviruses, and particularly integratable DNA fragments (i.e., fragments integratable into the host genome by homologous recombination). The vector may replicate and function independently of the host genome, or more preferably, may, in some instances, integrate into the genome itself. Suitable vectors will contain replicon and control sequences which are derived from species compatible with the intended expression host. Transformed host cells are cells which have been transformed or transfected with recombinant expression constructs made using recombinant DNA techniques and comprising mammalian MC receptor-encoding sequences. Preferred host cells are human 293 cells. Preferred host cells for the MC-2 (ACTH) receptor are Y1 cells (subclone OS3 or Y6). Transformed host cells are chosen that are capable of expressing functional MC receptor protein introduced using the recombinant expression construct. When expressed, the mammalian MC receptor protein will typically be located in the host cell membrane. See, Sambrook et at., ibid.

Cultures of cells derived from multicellular organisms are a desirable host for recombinant MC receptor protein synthesis. In principal, any higher eukaryotic cell culture is workable, whether from vertebrate or invertebrate culture. However, mammalian cells are preferred, as illustrated in the Examples. Propagation of such cells in cell culture has become a routine procedure. See *Tissue Culture*, Academic Press, Kruse & Patterson, editors (1973). Examples of useful host cell lines are human 293 cells, VERO and HeLa cells, Chinese hamster ovary (CHO) cell lines, mouse Y1 (subclone OS3), and W1138, BHK, COS-7, CV, and MDCK cell lines. Human 293 cells are preferred.

Cells expressing mammalian MC receptor proteins made endogenously or from heterologous cloned genes genetically engineered in accordance with the present invention may be used for screening agonist and antagonist compounds for MC receptor activity. Competitive binding assays are well known in the art and are described in the Examples below. Such assays are useful for drug screening of MC receptor agonist and antagonist compounds, as detected in receptor binding assays as described below.

The invention also provides membrane preparation from cells expressing MC receptors either endogenously or as the result of transformation with a recombinant expression construct, as described herein, useful for screening agonist or antagonist compounds for MC receptor binding activity, or for determining the amount of a MC receptor agonist or antagonist drug in a solution (e.g., blood plasma or serum). For example, cells expressing a melanocortin receptor protein, most preferably an MC5-R receptor protein, either endogenously or as the result of transformation with a recombinant expression construct of the present invention, are obtained according to the methods of the invention, the cells lysed, and the membranes from those cells used to screen compounds for MC receptor binding activity. Competitive binding assays in which such procedures may be carried out are well known in the art. By selection of host cells that express only one endogenous melanocortin receptor, or that do not ordinarily express a melanocortin receptor and are transformed with a recombinant expression construct of the invention encoding such a melanocortin receptor, preferably from a heterologous mammalian species, pure preparations of membranes containing only that melanocortin receptor can be obtained. Further, membranes obtained from such cells can be used in binding studies wherein the drug dissociation activity is monitored.

Alternatively, intact cells can be used to detect, monitor and characterize melanocortin receptor agonists and antagonists by assaying for a cellular product, either naturally-occurring or encoded by a reporter gene genetically engineered into the recipient cell, that is produced by the cell upon melanocortin receptor binding. These and other receptor-binding assays, including assays detecting transcription of a gene sensitive to melanocortin receptor agonist binding, binding of radiolabeled agonist or antagonist species to a melanocortin receptor or competition binding variations thereof, and the detection of an enzymatic or antigenic activity mediated by a protein produced as the result of melanocortin receptor binding are provided by the invention and will be understood in the art as being equivalent to the methods explicitly disclosed herein.

Also provided by the methods of the invention are reagents and methods for producing an animal, preferably a rodent and most preferably a mouse, bearing a homozygous disruption of both allelic copies of a particular melanocortin receptor, resulting in genetic ablation of the particular melanocortin receptor gene. Preferably, the melanocortin receptor is the MC5-R receptor and most preferably the melanocortin receptor is the mouse MC5-R receptor. Reagents provided by the invention include so-called "knockout" recombinant genetic constructs comprising a defective, most preferably a deleted, species of the melanocortin receptor encoding sequences, additional homologous sequences 5' and 3' from the defective coding sequences, and selectable markers for selecting clones of cells bearing the construct. Such selectable markers can be any known selectable gene, such as the genes for neomycin resistance, hygromycin resistance, the guanine phosphotransferase gene of *E. coli* (Ecogpt) and others known in the art. Particularly preferred are constructs comprising a herpesvirus thymidine kinase gene introduced in an orientation that permits selection against transformed or transfected cells having the construct incorporated randomly (as opposed to specifically by homologous recombination) into the host cell DNA. These constructs of the invention are provided to maximize the likelihood that recombinant cells will incorporate the construct DNA into host cell genomic DNA by homologous recombination that disrupts at least one allele of the target MC receptor.

Also provided by the invention are cultures of cells transformed with such "knockout" recombinant genetic constructs, preferably stem cells and most preferably embryonic stem (ES) cells capable of being introduced into a mammalian blastocyst and being incorporated into the cells of the organism upon development. The invention therefore also provides such transgenic animals produced thereby, most preferably having at least one of the endogenous melanocortin receptor genes disrupted by homologous recombination by the "knockout" recombinant genetic construct. The invention also provides colonies of inbred and outbred mice bearing a disrupted species of a melanocortin receptor in heterozygous (i.e., on only one chromosome) or homozygous (i.e., on both homologous chromosomes) condition, most preferably wherein the cells in the tissues of the animals bearing the disrupted species include germ cells (i.e., sperm cells, egg cells and their progenitors), thereby providing genetic transmission of the disrupted allele by mating. Most preferred are so-called "knockout" mice bearing the disrupted melanocortin receptor gene in their germ cells in the homozygous condition.

The invention also provides primary and immortalized cell cultures derived from tissues and organs of melanocortin "knockout" rodents, preferably mice, provided by the invention. Preferably, such rodents are mice bearing disrupted alleles of the melanocortin MC5-R receptor in the homozygous conditions, thereby providing primary and immortalized cell and organ cultures that are functionally and genetically null for MC5-R receptor expression. Such primary and immortalized cell and organ cultures thereby provide means and assays for comparing the effects of agonist and antagonist binding to cells endogenously or heterologously expressing the MC5-R receptor and developmentally equivalent cells that cannot express this receptor due to the homozygous engineered MC5-R gene disruption. Use of said primary and immortalized cell and organ cultures in assays for detecting and characterizing melanocortin receptor binding to agonist and antagonist compounds is provided by the invention.

Thus, the invention provides a variety of methods that are screening assays for detecting and characterizing agonists and antagonists of melanocortin receptor, most preferably MC5-R receptors.

The invention also provides an assay system, comprising a panel of cells expressing each of the known melanocortin receptors either endogenously or as recombinant mammalian cells heterologously expressing each of the MC receptors disclosed herein, wherein the panel is constructed of at least one cell line expressing an MC receptor, most preferably an MC5-R receptor. The invention provides such panels also comprising a detection means for detecting receptor agonist or antagonist binding, such as the reporter expression constructs described herein, and using direct binding and competition binding assays as described in the Examples below. In the use of this panel, each MC receptor is assayed for agonist or antagonist patterns of binding a test compound, and a characteristic pattern of binding for all MC receptors is thereby determined for each test compound. This pattern is then compared with known MC receptor agonists and antagonists to identify new compounds having a pattern of receptor binding activity associated with a particular behavioral or physiological effect.

The invention provides an in vitro assay to characterize MC5-R agonists/antagonists as a preliminary and economical step towards developing exocrine gland modulating drugs for use in vivo.

The MC receptor binding agonists, antagonists and analogues provided using the methods of the invention, and in particular those analogues that are MC5-R receptor agonists, antagonists or analogues are provided to be used in methods of treating, controlling, ameliorating and alleviating diseases, and dysfunctional and abnormal states related to thermoregulatory disorders, as well as other diseases relating to exocrine gland disorders, including lacrimal gland dysfunction and sebaceous gland disorders including acne and other skin problems. Specific examples of uses for the MC receptor binding analogues of the invention include but are not limited to treatment of skin disorders such as acne and other diseases related to the over- or under-production of sebaceous gland products; for the treatment of ocular disorders related to the production or lack thereof of tears and ocular lubrication; and diseases and disorders in animals related to estrus, mating, gestation or other pheromone-related disorders.

The Examples which follow are illustrative of specific embodiments of the invention, and various uses thereof. They set forth for explanatory purposes only, and are not to be taken as limiting the invention.

EXAMPLE 1

Isolation of an αMSH Receptor Probe by Random PCR Amplification of Human Melanoma cDNA Using Degenerate Oligonucleotide Primers In order to clone novel G-protein coupled receptors, cDNA prepared from RNA from human melanoma cells was used as template for a polymerase chain reaction (PCR)-based random cloning experiment. PCR was performed using a pair of degenerate oligonucleotide primers corresponding to the putative third and sixth membrane regions of G-protein coupled receptors (Libert et al., 1989, *Science* 244:569–72; Zhou et al., 1990, *Nature* 347:76–80). The PCR products obtained in this experiment were characterized by nucleotide sequencing. Two novel sequences representing novel G-protein-coupled receptors were identified.

PCR amplification was performed as follows. Total RNA was isolated from a human melanoma tumor sample by the guanidinium thiocyanate method (Chirgwin et al., 1979, *Biochemistry* 18:5294–5299). Double-stranded cDNA was synthesized from total RNA with murine reverse transcriptase (BRL, Gaithersburg, Md.) by oligo-dT priming (Sambrook et al., ibid.). The melanoma cDNA mixture was then subjected to 45 cycles of PCR amplification using 500 picomoles of degenerate oligonucleotide primers having the following sequence:
Primer III (sense):
GAGTCGACCTGTG(C/T)G(C/T)(C/G)AT(C/T)(A/G)CIIT(G/T)GAC(C/A)G(C/G)TAC (SEQ ID NO: 1)
and
Primer VI (antisense):
CAGAATTCAG(T/A)AGGGCAICCAGCAGAI(G/C)(G/A)(T/C)GAA (SEQ ID NO: 2)
in 100 μL of a solution containing 50 mM Tris-HCI (pH 8.3), 2.5 mM MgCl$_2$, 0.01% gelatin, 200 μM each dNTP, and 2.5 Units of Taq polymerase (Saiki et al., 1988, *Science* 239:487–491). These primers were commercially synthesized by Research Genetics Inc. (Huntsville, Ala.). Each PCR amplification cycle consisted of incubations at 94° C. for 1 min (denaturation), 45° C. for 2 min (annealing), and 72° C. for 2 min (extension).

Amplified products of the PCR reaction were extracted with phenol/chloroform and precipitated with ethanol. After digestion with EcoRI and SalI, the PCR products were separated on a 1.2% agarose get. A slice of this gel, corresponding to PCR products of 300 basepairs (bp) min size, was cut out and purified using glass beads and sodium iodide, and the insert was then cloned into a pBKS cloning vector (Stratagene, LaJolla, Calif.).

A total of 172 of such pBKS clones containing inserts were sequenced using Sequenase (U.S. Biochemical Corp., Cleveland, Ohio) by the dideoxynucleotide chain termination method (Sanger et al., 1977, *Proc. Natl. Acad. Sci. USA* 74:5463–5467). Two types of sequences homologous to other G-protein coupled receptors were identified.

EXAMPLE 2A

Isolation of a Mouse αMSH (MC1-R) Receptor cDNA

Probes isolated in Example 1 were used to screen a Cloudman melanoma cDNA library in order to isolate a full-length cDNA corresponding to the cloned probe. One clone was isolated from a library of 5×10$^7$ clones screened as described below. This clone contained an insert of 2.6 kilobases (kb). The nucleotide sequence of the complete coding region was determined (see co-owned U.S. Pat. No. 5,532,347, incorporated by reference); a portion of this cDNA comprising the coding region was sequenced and is shown in FIGS. 1A and 1B (SEQ ID Nos: 3&4).

EXAMPLE 2B

Isolation of a Human αMSH (MC1-R) Receptor cDNA

In order to isolate a human counterpart of the murine melanocyte αMSH receptor gene disclosed in Example 2A and in co-owned U.S. Pat. No. 5,532,347, a human genomic library was screened at high stringency (50% formamide, 42° C.) using the human PCR fragments isolated as described in Example 1. An isolated genomic clone was determined to encode an human MSH receptor (SEQ ID NO: 5.; FIGS. 2A and 2B). The human MSH receptor has a predicted amino acid sequence (SEQ ID NO: 6) that is 75% identical and collinear with the mouse αMSH receptor cDNA sequence. The predicted molecular weight of the human MSH receptor is 34.7 kD.

EXAMPLE 2C

Isolation of a Human ACTH (MC2-R) Receptor cDNA

For cloning the ACTH receptor (MC2-R), a human genomic library was screened at high stringency (50% formamide, 1M NaCl, 50 mM Tris-HCl, pH 7.5, 0.1% sodium pyrophosphate, 0.2% sodium dodecyl sulfate, 100 μg/mL salmon sperm DNA, 10×Denhardt's solution, 42° C.), using the human PCR fragments isolated as described in Example 1 herein and U.S. Pat. No. 5,280,112, incorporated by reference. A genomic clone was isolated that encodes a highly related G-coupled receptor protein (SEQ ID No: 7 and FIGS. 3A and 3B). The predicted amino acid sequence (SEQ ID NO: 8) of this clone is 39% identical and also collinear, excluding the third intracellular loop and carboxy-terminal tail, with the human MSH receptor gene product. The predicted molecular weight of this ACTH receptor is 33.9 kilodaltons (kD). This clone was identified as encoding an MC2-R receptor based on its high degree of homology to the murine and human MSH receptors, and the pattern of expression in different tissue types, as described in Example 3 in U.S. Pat. No. 5,280,112, incorporated by reference herein.

EXAMPLE 2D

Isolation of a Bovine ACTH (MC2-R) Receptor cDNA

A bovine genomic DNA clone encoding the bovine counterpart of the MC2-R (ACTH) receptor was isolated from a bovine genomic library, essentially as described in Example 2C above, and its nucleotide sequence determined (as shown in FIGS. 4A and 4B; SEQ ID Nos: 9 & 10).

EXAMPLE 2E

Isolation of a Rat γ-MSH (MC3-R) Receptor cDNA

The mouse αMSH receptor cDNA isolated as described in Example 2A and co-owned U.S. Pat. No. 5,532,347 was used to screen a rat hypothalamus cDNA library at low stringency (30% formamide, 5×SSC, 0.1% sodium pyrophosphate, 0.2% sodium dodecyl sulfate, 100 g/mL salmon sperm DNA, and 10% Denhardt's solution) at 42° C. for 18 h. A 1 kb cDNA clone was isolated and sequenced as described in co-owned U.S. Pat. No. 5,532,347, and this clone used to re-screen the rat hypothalamus cDNA library at high stringency (same conditions as above except that formamide was present at 45%). A cDNA clone approximately 2.0 kb in length was isolated and analyzed as described in co-pending U.S. application Ser. No. 08/044,812, incorporated by reference; a portion of this cDNA comprising the coding region was sequenced and is shown in FIGS. 5A and 5B (SEQ ID Nos: 11 & 12).

EXAMPLE 2F

Isolation of a Human MC4-R Receptor DNA

For cloning the MC4-R receptor, a human genomic library was screened at moderate stringency (40% formamide, 1M NaCl, 50 mM Tris-HCl, pH 7.5, 0.1% sodium pyrophosphate, 0.2% sodium dodecyl sulfate, 100 μg/mL salmon sperm DNA, 10× Denhardt's solution, 42° C.), using rat PCR fragments isolated as described in Example 1 herein, with the exception that the following primers were used for PCR:

Primer II (sense):
GAGTCGACC(A/G)CCCATGTA(C/T)T(AGT)(C/T)TTCATCTG (SEQ ID No.:13)
and
Primer VII (antisense):
CAGAATTCGGAA(A/G)GC(A/G)TA(G/T)ATGA(A/G)GGGGTC (SEQ ID No.:14).

A genomic clone was isolated that encodes a highly-related G-coupled receptor protein (SEQ ID No.:15 and FIGS. 6A and 6B) on a 1.9 kb HindIII fragment. The predicted amino acid sequence (SEQ ID No.:16) of this clone shares 55–61% sequence identity with human MC3-R and MC5-R receptors, and 46–47% sequence identity with the human MC1-R and MC2-R (ACTH) receptors.

EXAMPLE 2G

Isolation of a Mouse MC5-R Receptor cDNA

One million clones from a mouse 129SVJ genomic library comprising 5 million clones constructed in the λFixII vector (Stratagene) were screened at low stringency (hybridization in 40% formamide at 42° C., washing performed in 0.5×SSC at 60° C., as described above in Example 2E) using radio-labeled probes from the rat MC3-R and MC4-R receptors, as described in Examples 2E and 2F. Positively-hybridizing clones were isolated and sequenced, and the sequences obtained were compared to previously-isolated melanocortin receptor clones. One clone, comprising a previously-unknown sequence, was determined to encode the MC5-R melanocortin receptor. The nucleotide and amino acid sequences of this receptor are shown in FIGS. 7A and 7B (SEQ ID Nos.: 17 & 18).

EXAMPLE 3

Construction of a Recombinant Expression Construct, DNA Transfection and Functional Expression of the MCR Gene Products In order to produce recombinant mammalian cells expressing each of the melanocortin receptors of Example 2, cDNA or the coding exons from genomic DNA from each receptor were cloned into a mammalian expression construct, the resulting recombinant expression construct transfected into human 293 cells, that do not express an endogenous melanocortin receptor protein, and cell lines generated that expressed the melanocortin receptor proteins in cellular membranes at the cell surface.

The mouse αMSH receptor was cloned by excising the entire coding region of the MSH R (MC1-R) cDNA insert comprising a 2.1 kb fragment and subcloning this fragment into the BamHI/XhoI sites of pcDNA/neo expression vector (Invitrogen, San Diego, Calif.). The resulting plasmid was prepared in large-scale through one cycle of CsCl gradient ultracentrifugation, and 20 μg of the plasmid transfected into each 100 mm dish of 293 cells using the calcium phosphate method (see Chen & Okayama, 1987, *Mol Cell. Biol.* 7:2745–2752). After transfection, cells were cultured in DMEM media supplemented with 10% calf serum in a 3% $CO_2$ atmosphere at 37° C. Selection was performed with neomycin (G418; GIBCO, Long Island, N.Y.) at a concentration of 1000 μg/mL; selection was started 72 hr after transfection and continued for 3 weeks.

The αMSH receptor is known to couple to G-proteins and thereby activate adenyl cyclase, increasing intracellular levels of cAMP (see Buckley & Ramachandran, 1981, *Proc. Natl. Acad Sci. USA* 78:7431–7435; Grahame-Smith et al., 1967, *J Biol. Chem* 242:5535–5541; Mertz & Catt, 1991, *Proc. Natl. Acad. Sci. USA* 88:8525–8529; Pawalek et al., 1976, *Invest. Dermatol.* 66:200–209). This property of cells expressing the αMSH receptor was used analyze expression of the αMSH receptor in cell colonies transfected with the expression vectors described herein as follows. Cells (~1× $10^6$) were plated in 6-well dishes, washed once with DMEM containing 1% bovine serum albumin (BSA) and 0.5 mM isobutylmethylxanthine (IBMX, a phosphodiesterase inhibitor), then incubated for 45 minutes at 37° C. with varying concentrations of the melanotropic peptides αMSH, βMSH, γMSH, the MSH peptide analogue Nle$^4$, D-Phe$^7$-αMSH (NDP-MSH), and ACTH. Following hormone treatment, the cells were washed twice with phosphate buffered saline and intracellular cAMP extracted by lysing the cells with 1 mL of 60% ethanol. Intracellular cAMP concentrations were determined using an assay (Amersham) which measures the ability of cAMP to displace 8-$^3$H-cAMP from a high affinity cAMP binding protein (see Gilman, 1970, *Proc. Natl. Acad. Sci. USA* 67:305–312).

The results of these experiments are shown in FIG. 8. The abscissa indicates the concentration of each hormone and the ordinate indicates the percentage of basal intracellular cAMP concentration achieved by each treatment. Points indicate the mean of duplicate incubations; the standard error did not exceed 15% for any data point. None of the peptides tested induced any change in intracellular cAMP in cells containing the vector alone. Cells expressing the murine αMSH receptor responded to melanotropic peptides with a 2–3 fold elevation of intracellular cAMP, similar to levels of cAMP induced by these peptides in the Cloudman cell line (see Pawalek, 1985, *Yale J Biol. Med.* 58:571–578). The $EC_{50}$ values determined for αMSH ($2.0 \times 10^{-9}$ M), ACTH ($8.0 \times 10^{-9}$ M) and the superpotent MSH analogue NDP-MSH ($2.8 \times 10^{-11}$ M), correspond closely to reported values (see Tatro et al., 1990) ibid.). As expected, the βMSH peptide had an $EC_{50}$ value comparable to αMSH, while γMSH had little or no activity (see Slominski et al., 1992, *Life Sci.* 50:1103–1108), confirming the identity of this receptor as a melanocyte αMSH receptor.

Figure 9:
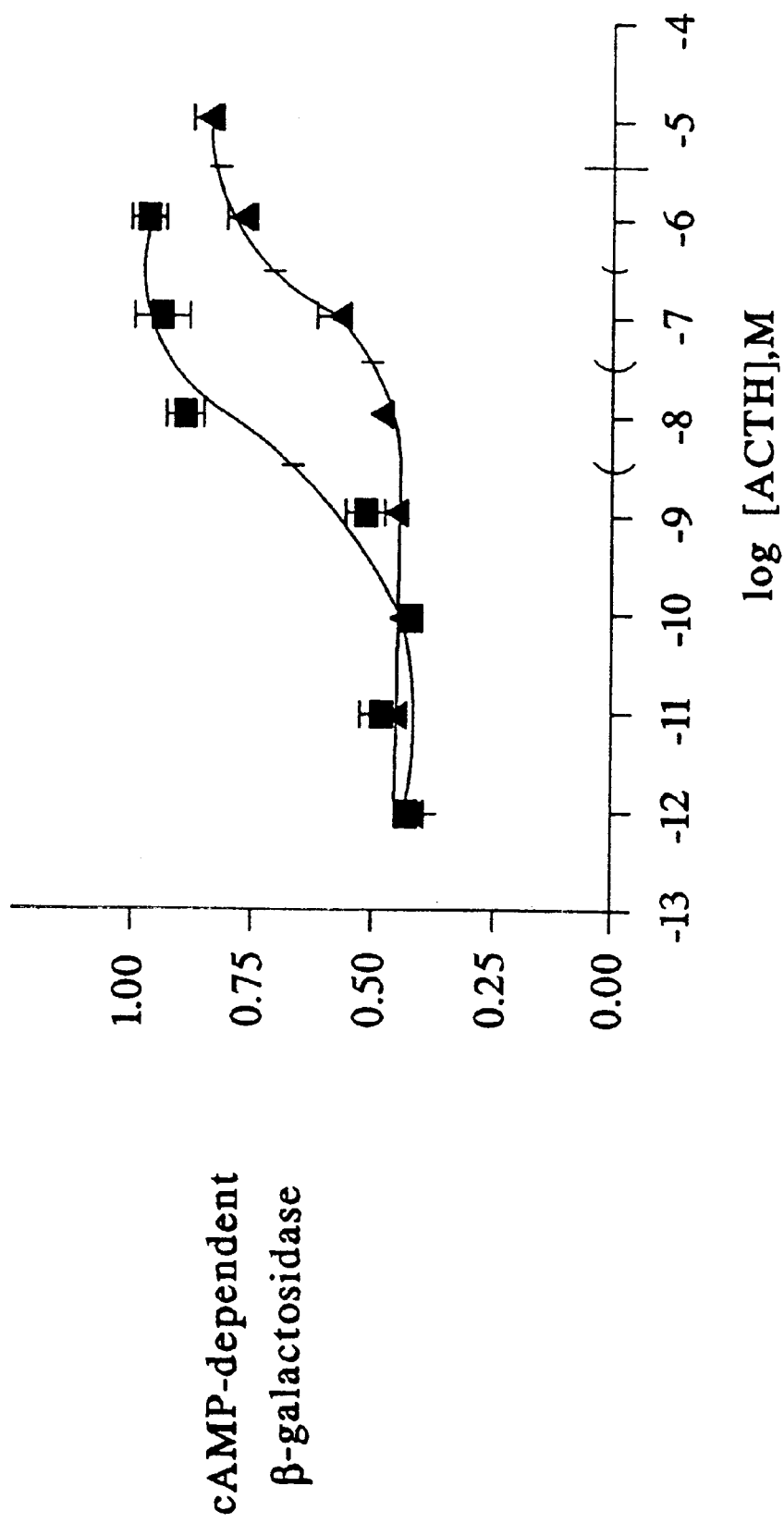
FIG. 9 illustrates the cAMP response of mouse Y1 cells to binding of melanocortin peptides to human melanocortin-2 (ACTH) receptor, as measured using the β-galactosidase assay described in Example 3.

A similar series of experiments were performed using mouse Y1 cells (subclone OS3; Schimmer et al., 1995, *J. Cell. Physiol.* 163:164–171) expressing the human and bovine MC2-R (ACTH) receptor clones of Examples 2C and 2D. These results are shown in FIG. 9, where the extent of cAMP responsive element-linked β-galactosidase activity (see below) is shown with increasing concentrations of ACTH.

The entire coding region of the MC3-R receptor cDNA insert, obtained as described in Example 2E above and in co-pending U.S. Ser. No. 08/044,812, was contained in a 2.0 kb restriction enzyme digestion fragment and was cloned into the BamHI/XhoI sites of pcDNA/neo I expression vector (Invitrogen, San Diego, Calif.). The resulting plasmid was prepared in large-scale through one cycle of CsCl gradient ultracentrifugation and 20 μg pcDNA/MC3-R receptor DNA were transfected into 293 cells by calcium phosphate co-precipitation using standard techniques, and plasmid-containing cells selected in G418-containing media.

Specific binding of melanocortin peptides to cells expressing the MC3-R receptor was demonstrated by competition experiments using $^{125}$I-labeled Nle$^4$-D-Phe$^7$-α-MSH (NDP-MSH, as described in Tatro et al, 1990, ibid.). Suspended cells ($2 \times 10^5$) were incubated at 37° C. with 500,000 cpm of labeled peptide for 10 min in binding buffer (Ham's F10 media plus 10 mM HEPES, pH 7.2, 0.25% bovine serum albumin, 500K IU/mL aprotinin, 100 μg/mL bacitracin and 1 mM 1,10-phenanthroline) in the presence or absence of the indicated concentrations of peptides. Maximum labeling was achieved within 10 min.

Figure 10:
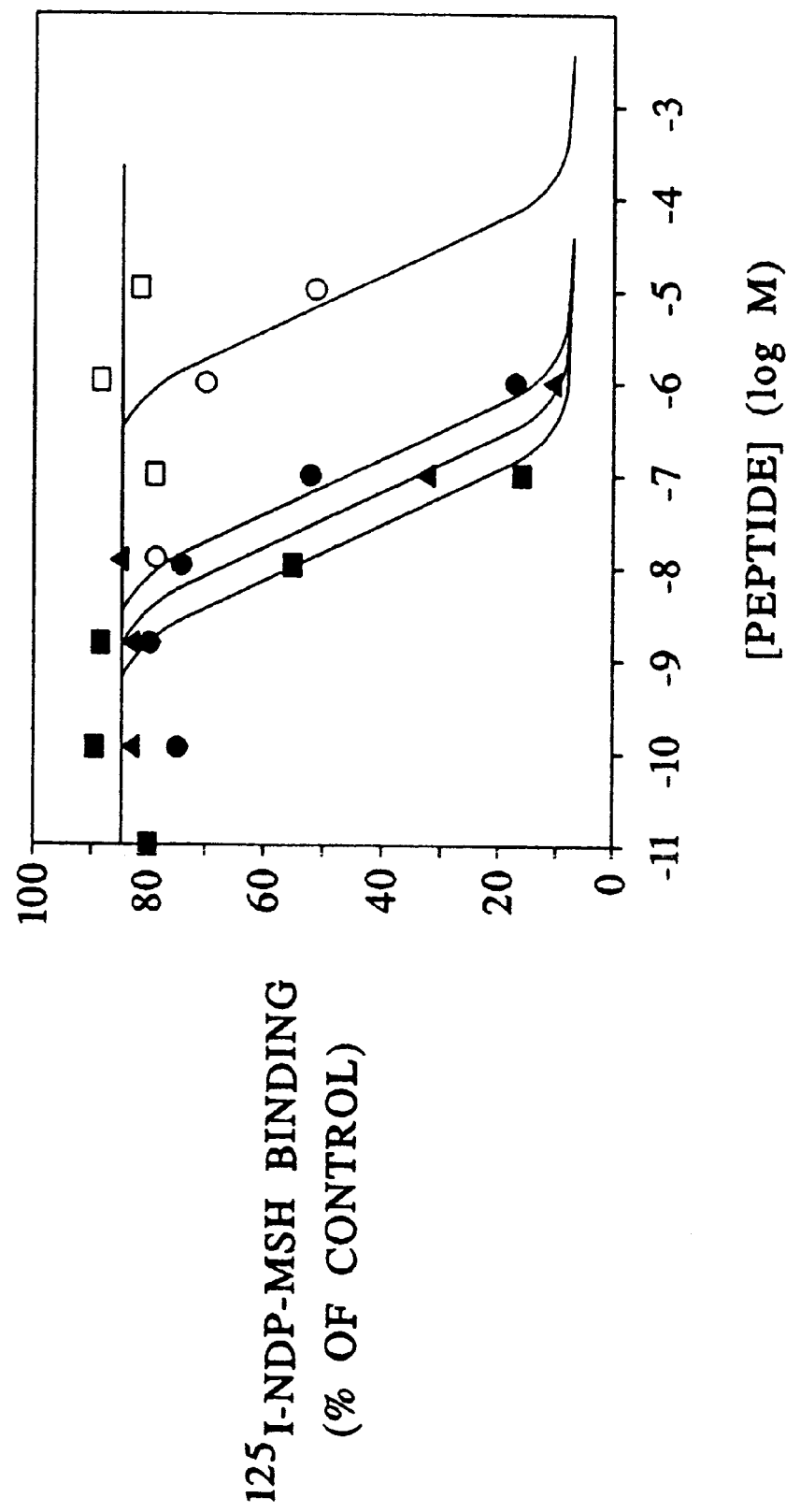
FIG. 10 illustrates the results of competition binding experiments of melanocortin peptides to cells expressing a recombinant expression construct encoding the rat melanocortin-3 receptor.

The results of these experiments are shown in FIG. 10. Labeled NDP-MSH binding to cells expressing the MC3-R receptor, produced as described above, is inhibited by competition with unlabeled peptides known to be melanocortin receptor agonists, having a relative order of potency as follows:

NDP-MSH>γ-MSH>α-MSH>ACTH$_{4-10}$>>>ORG2766.

Approximate $K_i$ values derived from this experiment are as shown in Table 1:

TABLE I

| Agonist | $K_i$ (approx.) |
|---|---|
| NDP-MSH | $2 \times 10^{-8}$ |
| γ-MSH | $5 \times 10^{-8}$ |
| α-MSH | $1 \times 10^{-7}$ |
| ACTH$_{4-10}$ | $8 \times 10^{-5}$ | cAMP production assays as described above were also used to analyze expression of MC3-R in cells transfected with the expression vectors described herein as follows. Cells (~$5 \times 10^6$) were plated in 6-well dishes, washed once with DMEM containing 1% bovine serum albumin (BSA) and 0.5 mM IBMX (a phosphodiesterase inhibitor), then incubated for 1 h at 37° C. with varying concentrations of the melanotropic peptides αMSH, γ$_3$MSH, γMSH, the MSH peptide analogues Nle-D-Phe$^7$-αMSH (NDP-MSH), ACTH$_{4-10}$ and ACTH$_{1-39}$. Following hormone treatment, the cells were washed twice with phosphate buffered saline and intracellular cAMP extracted by lysing the cells with 1 mL of 60% ethanol. Intracellular cAMP concentrations were determined using an assay which measures the ability of cAMP to displace (8-$^3$H)-cAMP from a high affinity cAMP binding protein (see Gilman, 1979, ibid.).

Figure 11A:
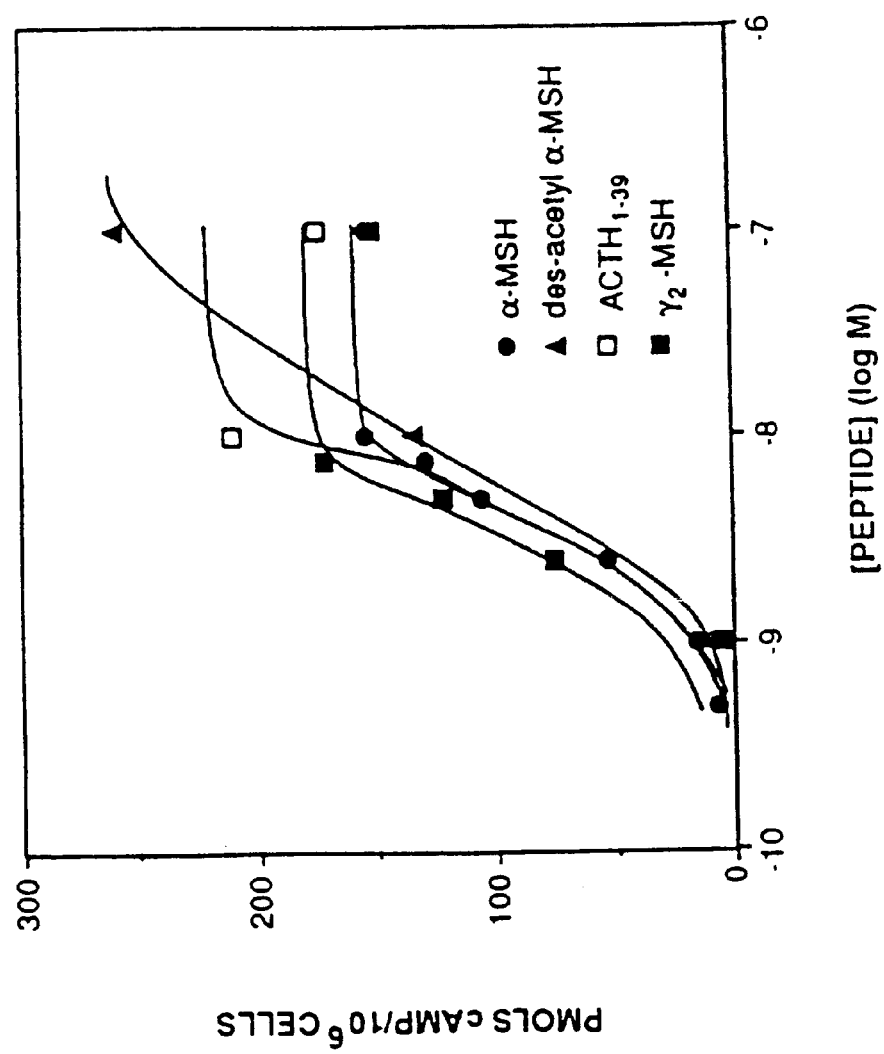
FIGS. 11A through 11C illustrate the results of experiment showing intracellular cAMP accumulation caused by receptor-ligand binding in human 293 cells expressing the MC3-R receptor.
Figure 11B:
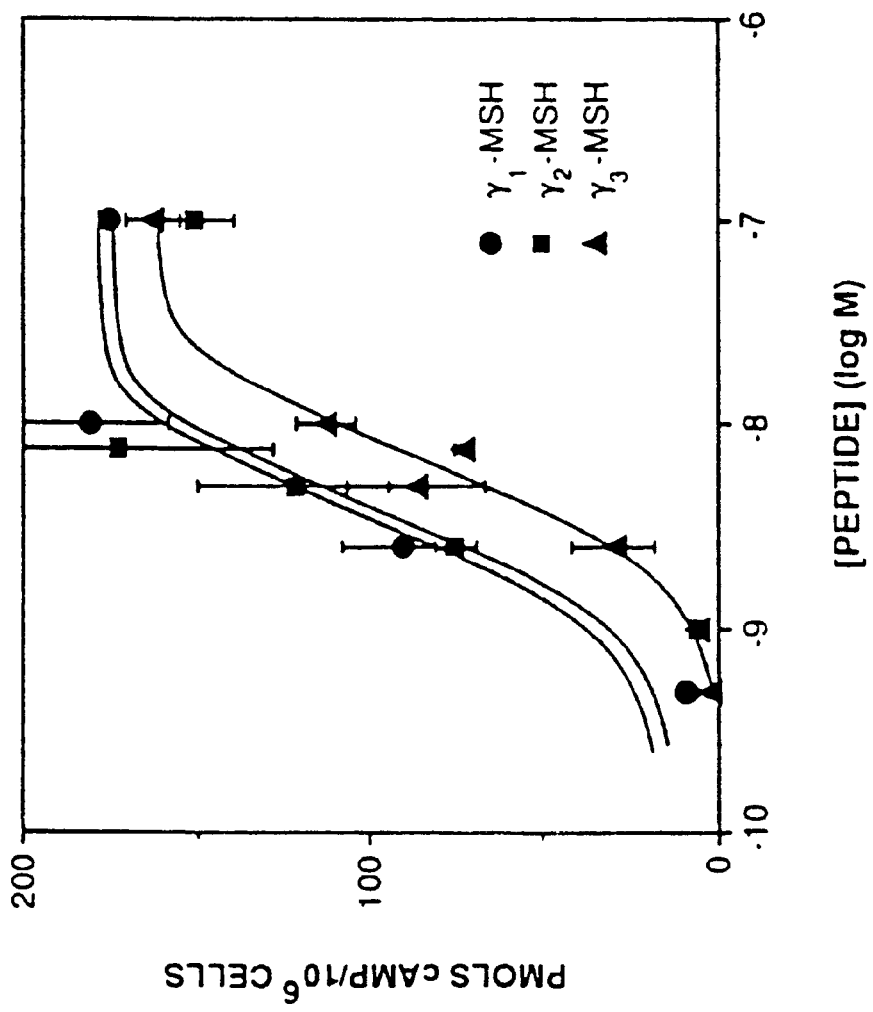
Figure 11C:
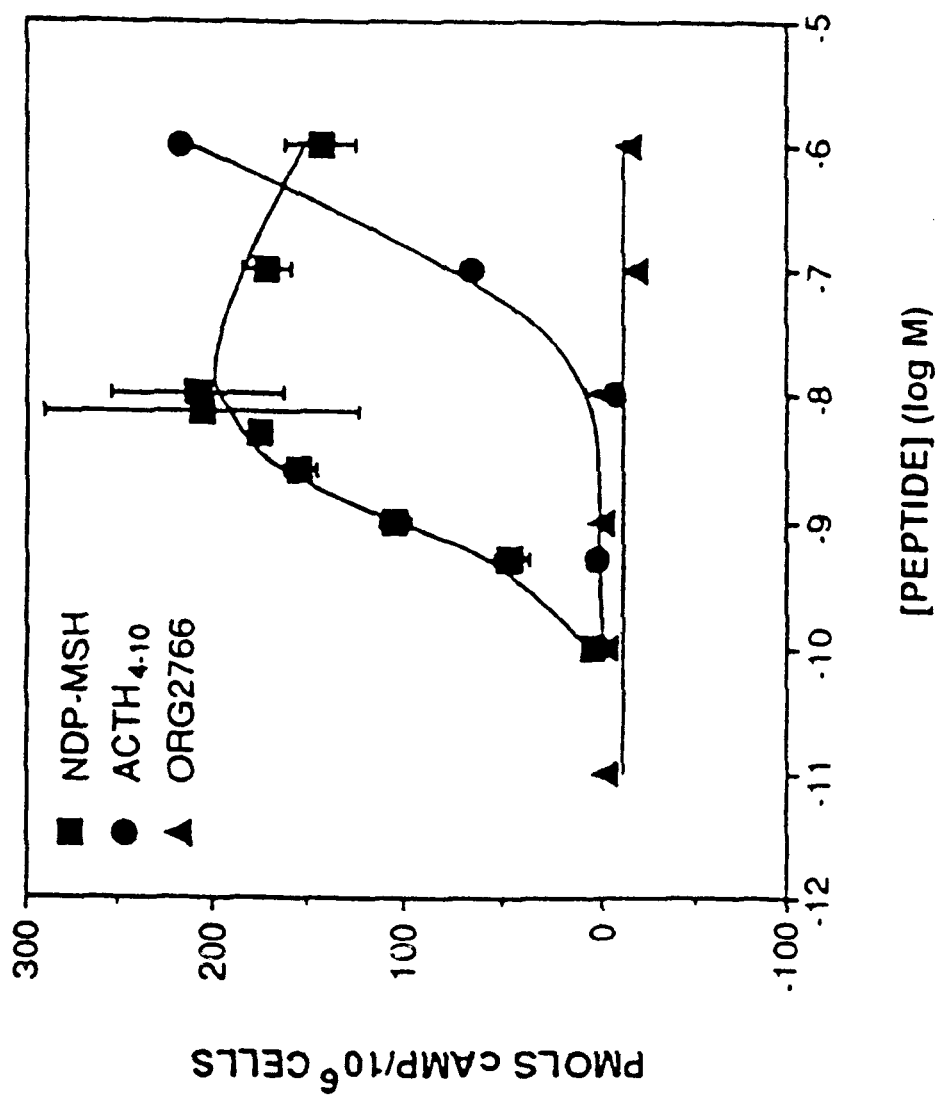

The results of these experiments are shown in FIGS. 11A through 11C. The abscissa indicates the concentration of each hormone and the ordinate indicates the percentage of basal intracellular cAMP concentration achieved by each treatment. Points indicate the mean of duplicate incubations; the standard error did not exceed 15% for any data point. FIG. 11A depicts the results of experiments using peptides found in vivo; FIG. 11B depicts results found with γ-MSH variants; and FIG. 11C shows results of synthetic melanocortin analogues. None of the peptides tested induced any change in intracellular cAMP in cells containing the vector alone. Cells expressing rat MC3-R responded strongly to every melanotropic peptide containing the MSH code sequence His-Phe-Arg-Trp, with up to a 60-fold elevation of intracellular cAMP levels. $EC_{50}$ values ranged from 1–50 nM. The most potent ligand and the one having the lowest $EC_{50}$ was found to be γMSH. The order of potency for the naturally occurring melanocortins was found to be:

$EC_{50}$ values for these compounds are shown in Table II:

TABLE II

| Agonist | $EC_{50}$ |
|---|---|
| NDP-MSH | $1 \times 10^{-9}$ |
| γ$_1$-MSH | $3 \times 10^{-9}$ |
| γ$_2$-MSH | $3 \times 10^{-9}$ |
| α-MSH | $4 \times 10^{-9}$ |
| ACTH$_{1-39}$ | $4 \times 10^{-9}$ |
| γ$_3$-MSH | $6 \times 10^{-9}$ |
| desacetyl-α-MSH | $8 \times 10^{-9}$ |
| ACTH$_{4-10}$ | $1 \times 10^{-7}$ |

Additionally, a synthetic melanocortin peptide (ORG2766), known to have the greatest activity in vivo in stimulation of retention of learned behavior and in stimulation of neural regeneration, was unable to stimulate MC3-R-mediated cAMP production, and was also inactive as an antagonist. The results strongly indicate that this peptide does not bind to MC3-R protein.

Figure 12:
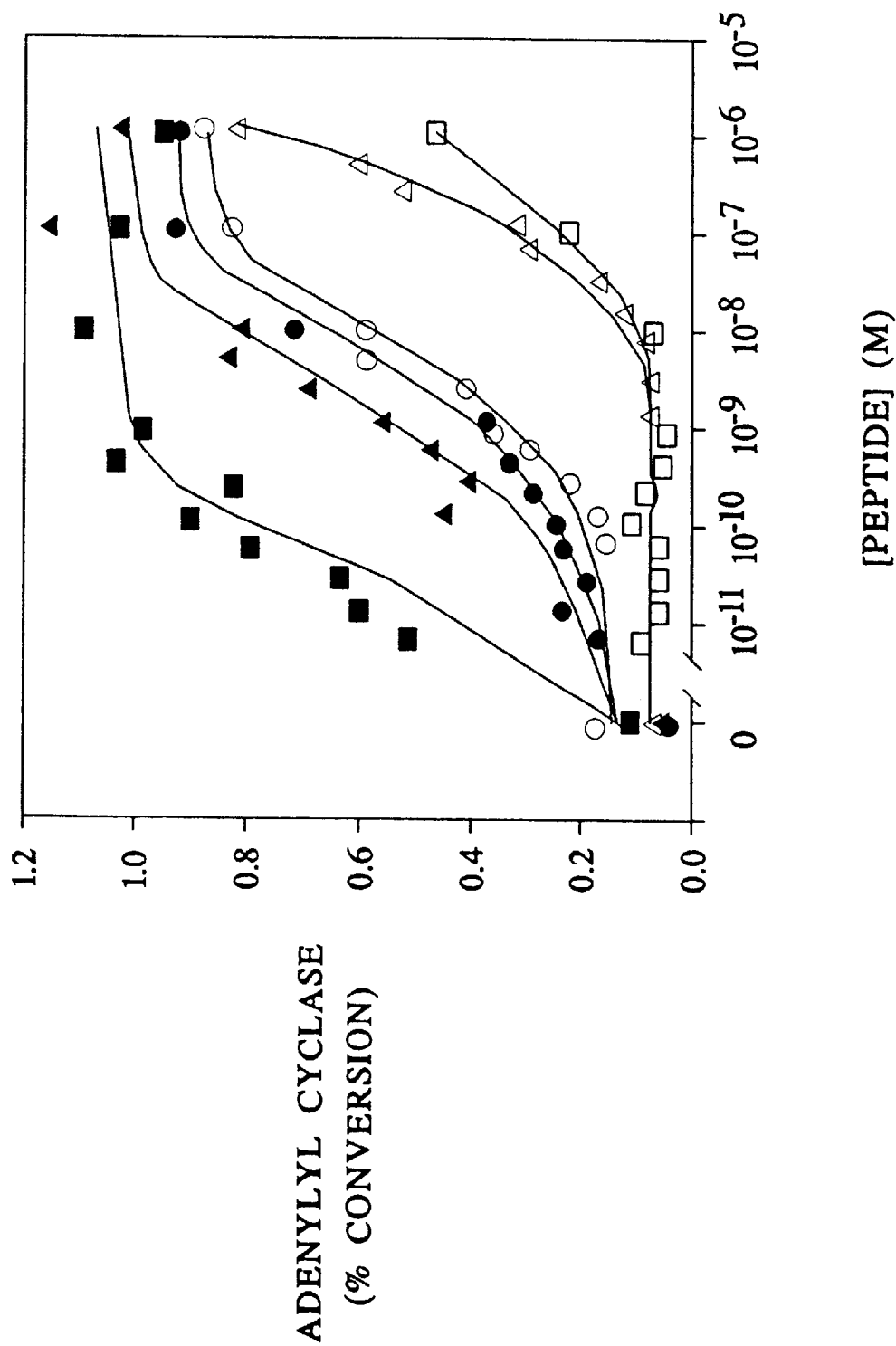
FIG. 12 shows a graph of intracellular cAMP accumulation resulting from melanocortin peptide binding to human melanocortin-4 receptor agonists in human 293 cells transfected with a MC4-R receptor-encoding recombinant expression construct.

The MC4-R receptor was cloned in a 1.9 kb HindIII genomic DNA fragment after PCR amplification of a lambda phage clone into pcDNAI/Neo (Invitrogen). This plasmid was stably introduced into human 293 cells by calcium phosphate co-precipitation using standard techniques, and plasmid-containing cells selected in G418 containing media. Specificity of receptor-hormone binding was assayed using adenylate cylcase activity as described above. The MC4-R receptor was found to couple to adenylate cyclase activity having the following pattern of agonist affinity:

NDP-MSH>des-acetyl-α-MSH>/=ACTH$_{1-39}$>/=α-MSH>>γ$_2$-MSH=ACTH$_{4-10}$ whereas the synthetic ACTH$_{4-9}$ analogue ORG2766 showed no detectable binding to the MC4-R receptor. The results of adenylate cyclase activity assays are shown in FIG. 12. EC$_{50}$ values for each of the tested MC4-R receptor agonists are as shown in Table III:

TABLE III

| Agonist | EC$_{50}$ |
|---|---|
| NDP-MSH | $1.1 \times 10^{-11}$ |
| desacetyl-α-MSH | $4.9 \times 10^{-10}$ |
| ACTH$_{1-39}$ | $6.8 \times 10^{-10}$ |
| α-MSH | $1.5 \times 10^{-9}$ |
| γ$_2$-MSH | $>10^{-7}$ |
| ACTH$_{4-10}$ | $>10^{-7}$ |

A 1.6 kb ApaI-HindIII fragment comprising the entire coding sequence of the mouse MC5-R melanocortin receptor disclosed in Example 2G above was cloned into the pcDNA/neo expression vector (Invitrogen) after PCR amplification of the lambda phage clone. This plasmid was stably introduced into human 293 cells by calcium phosphate co-precipitation using standard techniques, and plasmid-containing cells selected in G418 containing media. Specificity of receptor-hormone binding was assayed using adenylate cylcase activity as described above. The MC5-R receptor was found to couple to adenylate cyclase activity having the following pattern of agonist affinity:

α-MSH>βMSH>>γ-MSH

Figure 13:
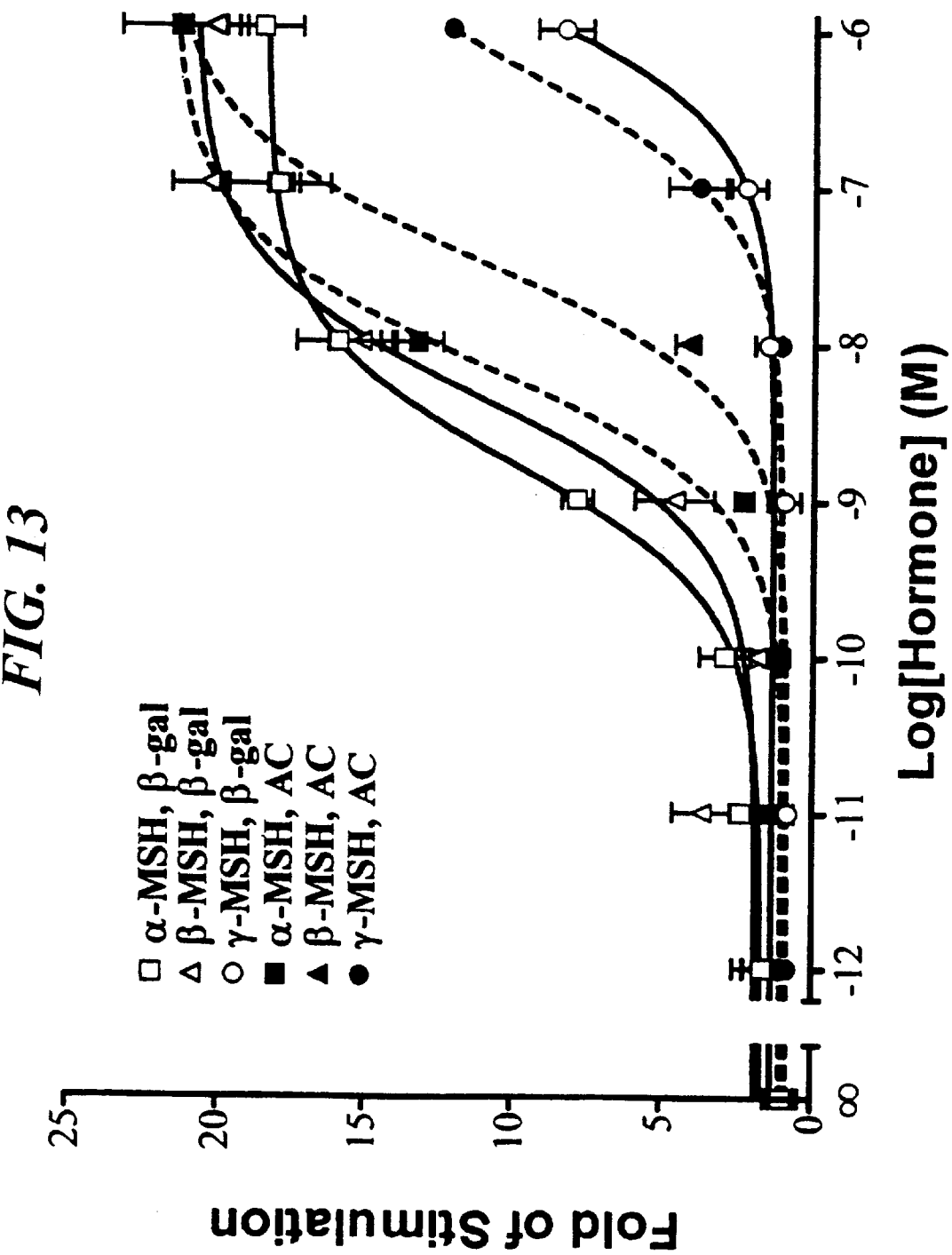
FIG. 13 illustrates the results of cAMP accumulation (AC) and cAMP-dependent β-galactosidase (β-gal) assays of melanocortin peptide binding to a rat melanocortin-5 receptor.

The results of adenylate cyclase activity assays (AC) and cAMP-dependent β-galactosidase (β-gal) assay are shown in FIG. 13. EC$_{50}$ values for each of the tested MC5-R receptor agonists are: α-MSH=$1.7 \times 10^{-9}$M, and βMSH=$5 \times 10^{-9}$M.

A. Use of a reporter gene construct to detect melanocortin receptor binding

Recombinant cells prepared as described above were used to characterize receptor binding of melanocortin analogues as described in co-owned and co-pending U.S. Ser. No. 08/706,281, filed Sep. 4, 1996, incorporated by reference herein.

Figure 14:
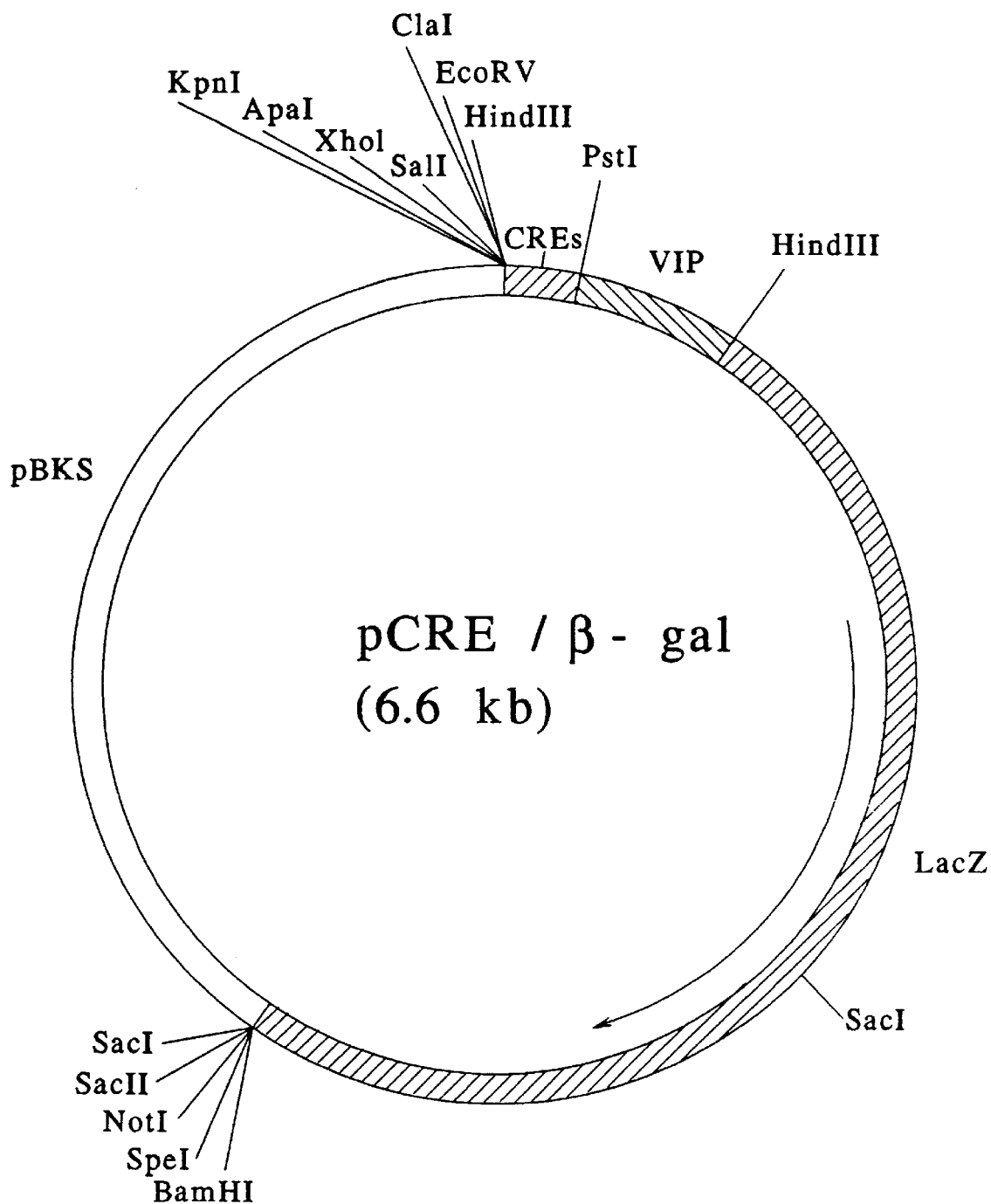
FIG. 14 illustrates the structure of the pCRE/ β-gal plasmid.

Briefly, melanocortin receptor analogues were tested using a calorimetric assay developed by some of the instant inventors (Chen et al., 1995, *Analyt. Biochem.* 226:349–354, incorporated by reference). A series of concatamers of the synthetic oligonucleotide:

5'-GAATTCGACGTCACAGTATGACGGCCATGG-3' (SEQ ID No.: 19)

was produced by self-annealing and ligation, producing a tandem tetramer. This fragment was cloned upstream of a fragment of the human vasoactive intestinal peptide (−93 to +152; see Fink et al., 1988, *Proc. Natl. Acad. Sci. USA* 85:6662–6666). This hybrid promoter was then cloned upstream of the β-galactosidase gene from *E. coli*. The resulting plasmid construct is shown in FIG. 14 and termed pCRE/β-gal.

Transient transfection of the pCRE/β-gal plasmid into mammalian cells was described as follows. Cells at between 40–60% confluency (corresponding to about 1.5 million cells/ 6 cm tissue culture dish) were incubated with Opti-MEM (GIBCO) And then contacted with a pCRE/β-gal-lipofectin complex which was prepared as follows. 3 μg plasmid DNA and 20 μL lipofectin reagent (GIBCO) were each diluted into 0.5 mL Opti-MEM media and then mixed together. This mixture was incubated at room temperature for 15–20 min, and then the mixture (1 mL) added to each 6 cm plate. Transfected plates were incubated at 37° C. for 5–24 h, after which time the plates were washed and incubated with DMEM media (GIBCO) and the cells split equally into a 96-well culture plate.

To assay melanocortin receptor analogue binding, human 293 cells expressing each of the melanocortin receptors MC1-R, MC3-R, MC4-R and MC5-R, and mouse Y1 cells expressing the MC2-R receptor, were transiently transfected with pCRE/β-gal as described above and assayed as follows. Two days after transfection, cells were stimulated with hormones specific for each receptor or hormone analogue by incubation for 6 h at 37° C. with a mixture comprising $10^{-12}$ to $10^{-6}$ M hormone or analogue, 0.1 mg/mL bovine serum albumin and 0.1 mM IBMX in DMEM. The effect of hormone or analogue binding was determined by β-galactosidase assay according to the method of Felgner et al. (1994, *J. Biol. Chem.* 269:2550–2561). Briefly, media was aspirated from culture wells and 50 μL lysis buffer (0.25M Tris-HCl, pH 8, 0.1% Triton X-100) added to each well. Cell lysis was enhanced by one round of freezing and thawing the cell/lysis buffer mixture. 10 μL aliquots were sampled from each well for protein determination using a commercially-available assay (Bio-Rad, Hercules, Calif.). The remaining 40 μL from each well was diluted with 40 μL phosphate buffered saline/ 0.5% BSA and 150 μL substrate buffer (60 mM sodium phosphate, 1 mM MgCl$_2$, 10 mM KCl, 5 mM β-mercaptoethanol, 200 μg/μL o-nitrophenyl-β-D-galactopyranoside) added. Plates were incubated at 37° C. for 1 h and then absorbance at 405 nm determines using a 96-well plate reader (Molecular Devices, Sunnyvale, Calif.). A series of two-fold dilutions ranging from 20 ng of purified β-galactosidase protein (Sigma Chemical Co., St. Louis, Mo.) were assayed in parallel in each experiment to enable conversion of OD$_{405}$ to known quantities of β-galactosidase protein.

Figure 15A:
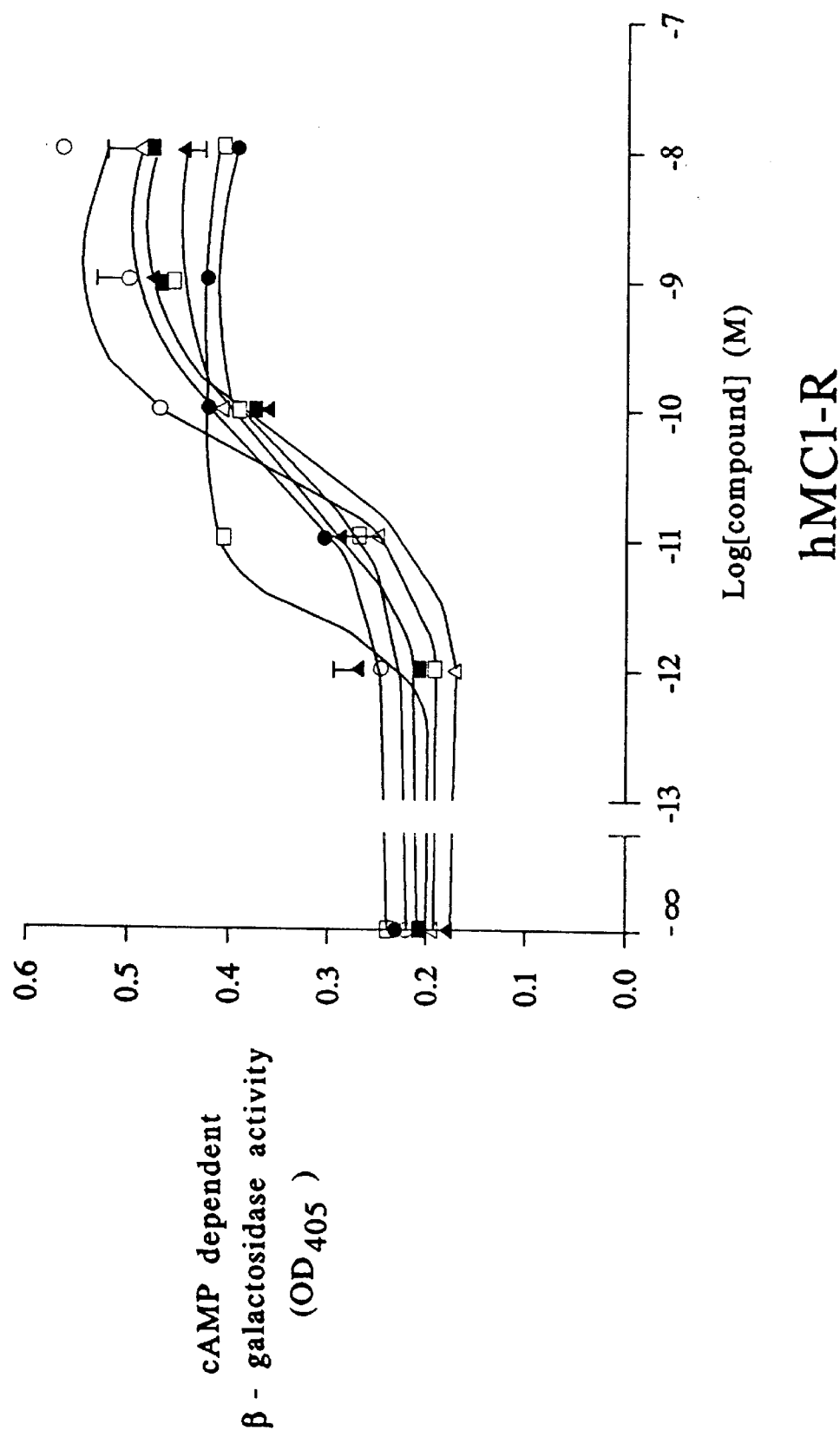
Figure 15B:
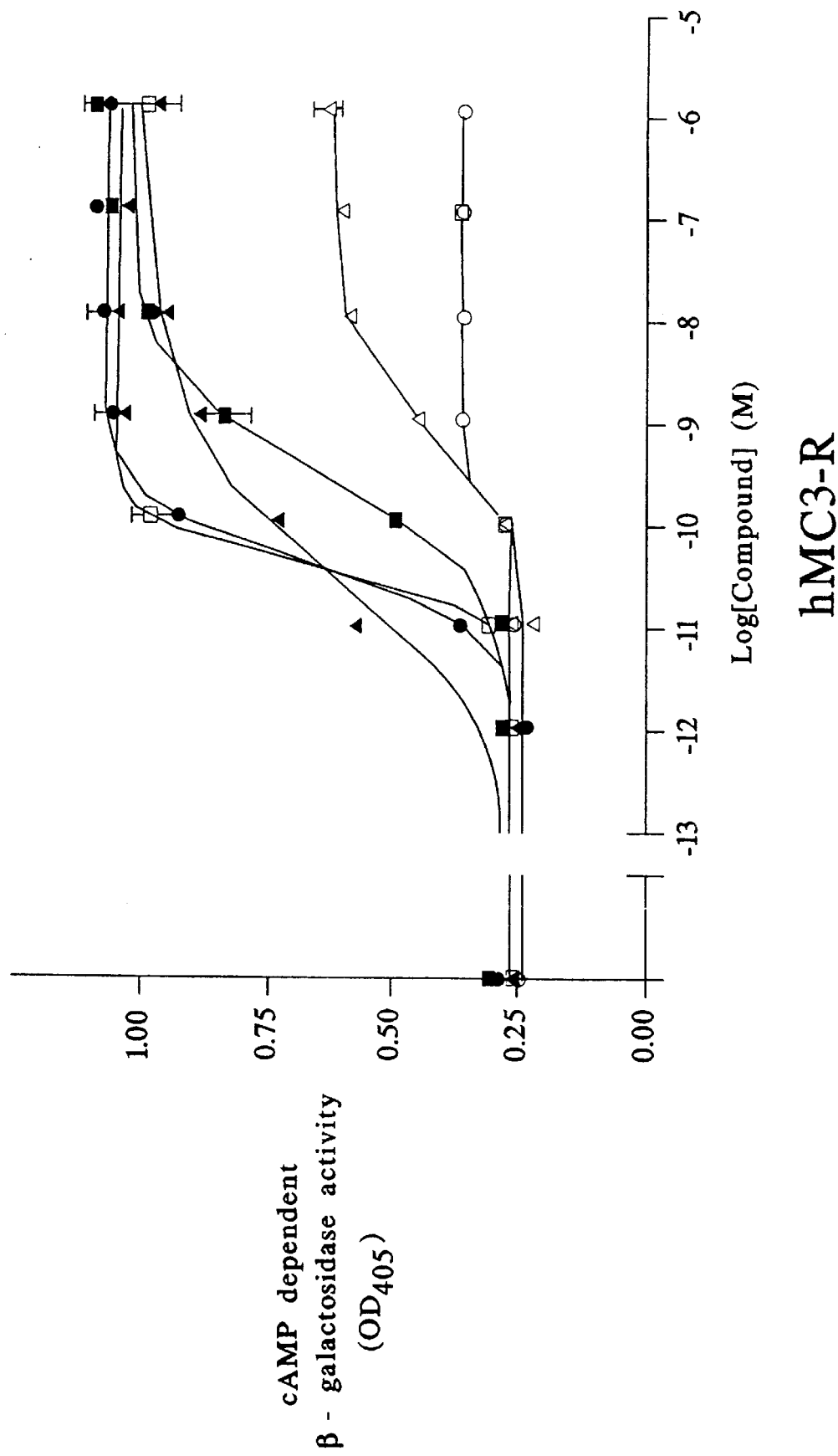
Figure 15C:
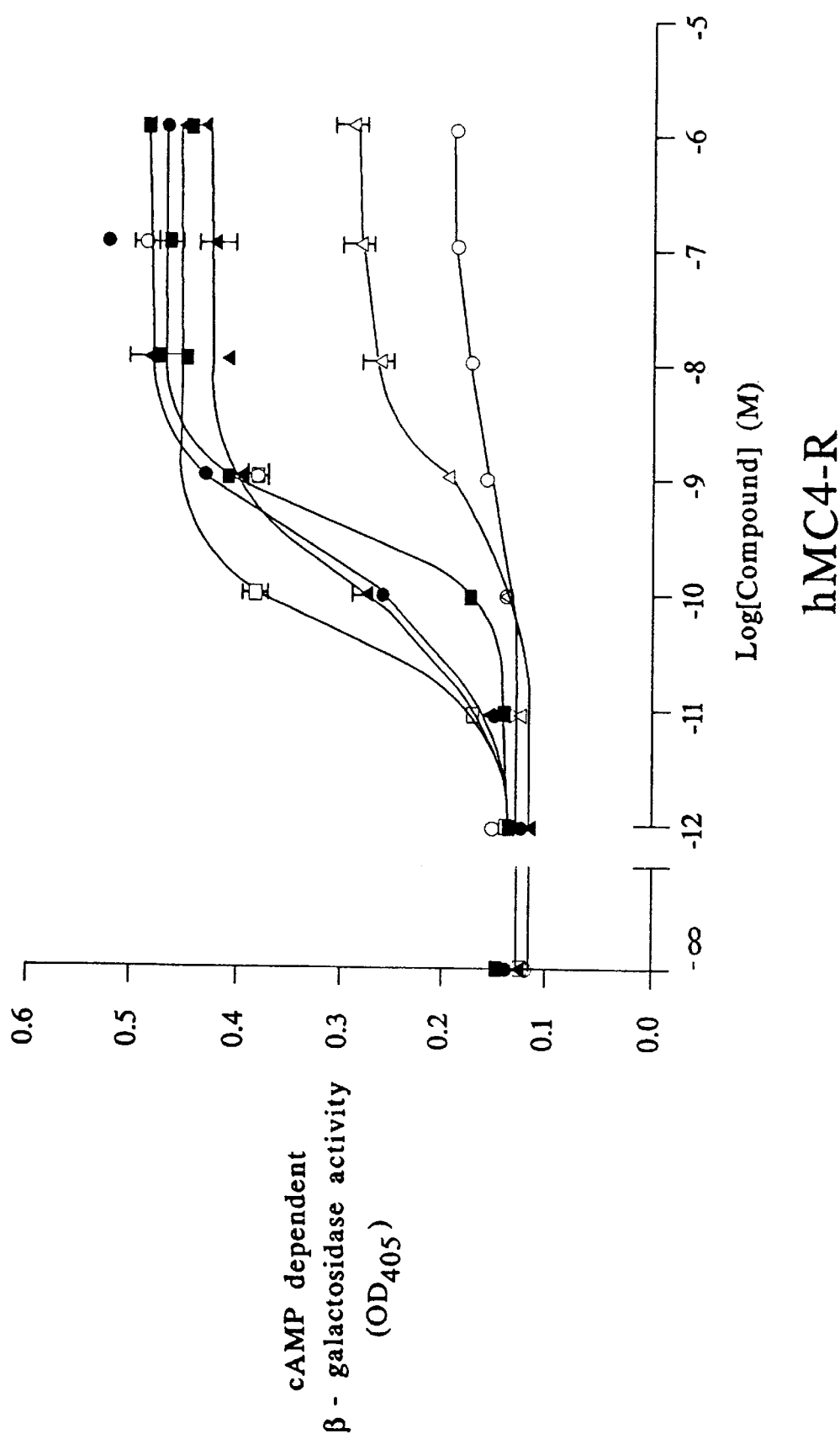
Figure 15D:
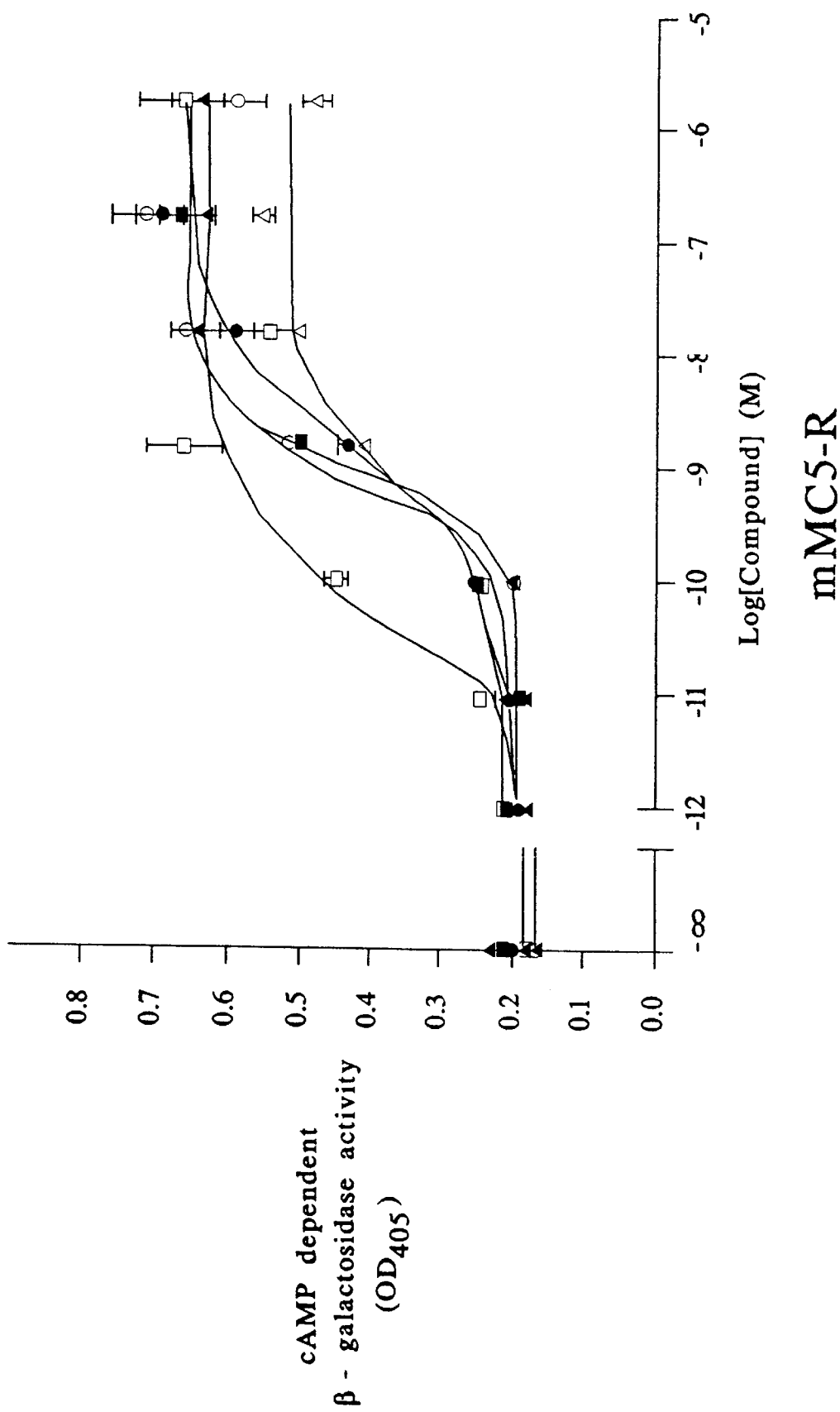
Figure 15E:
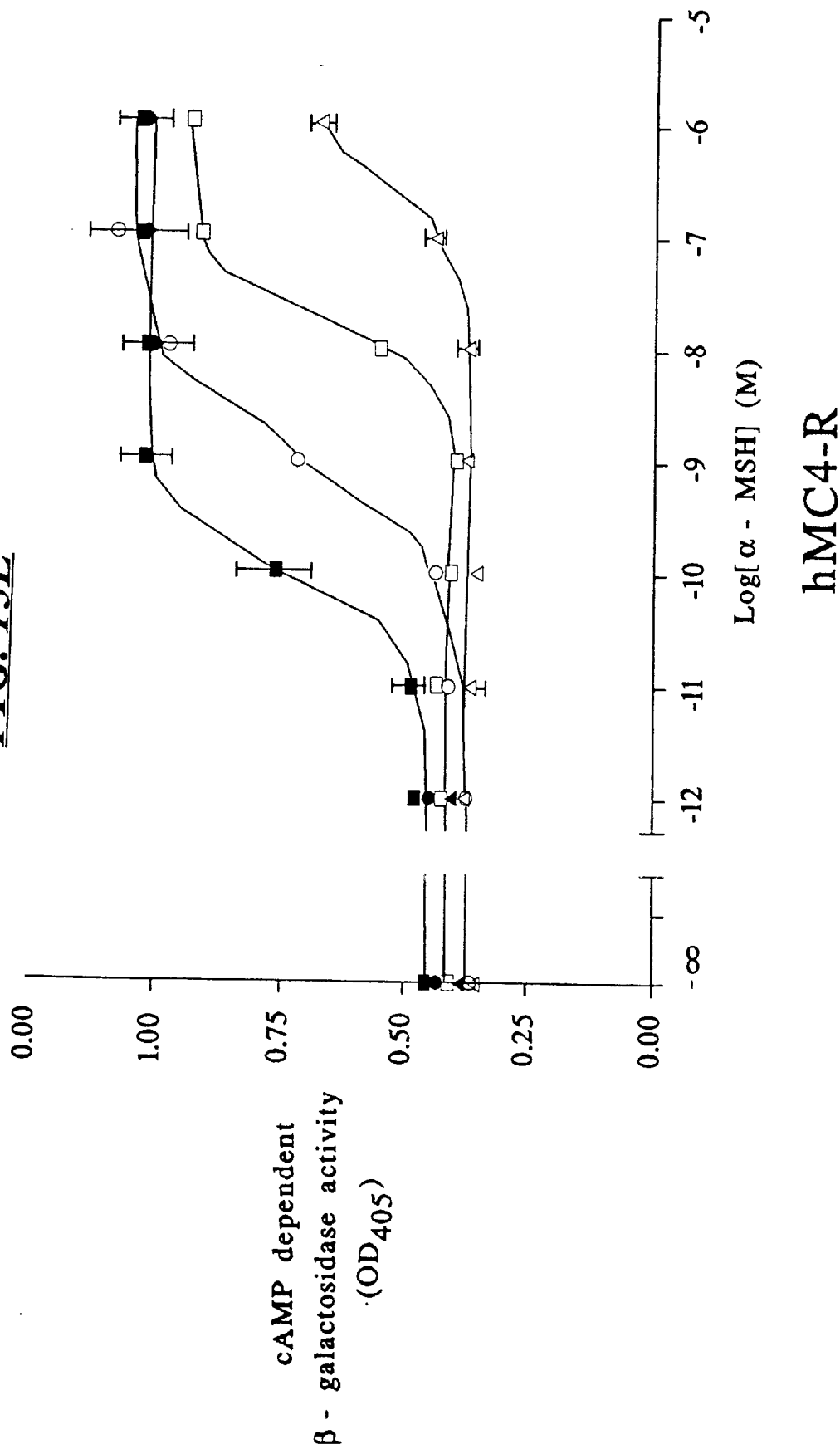
Figure 15F:
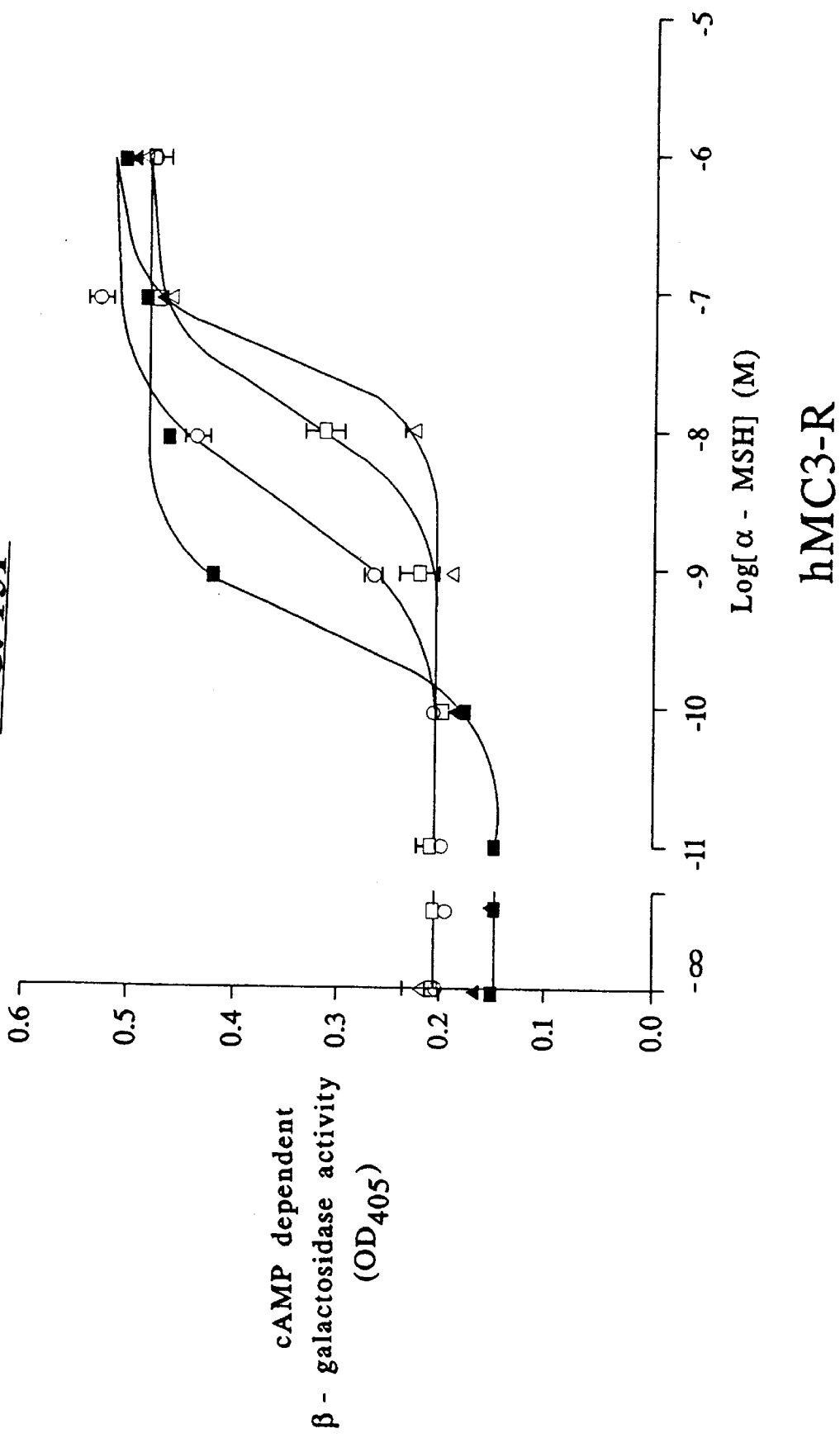
Figure 15G:
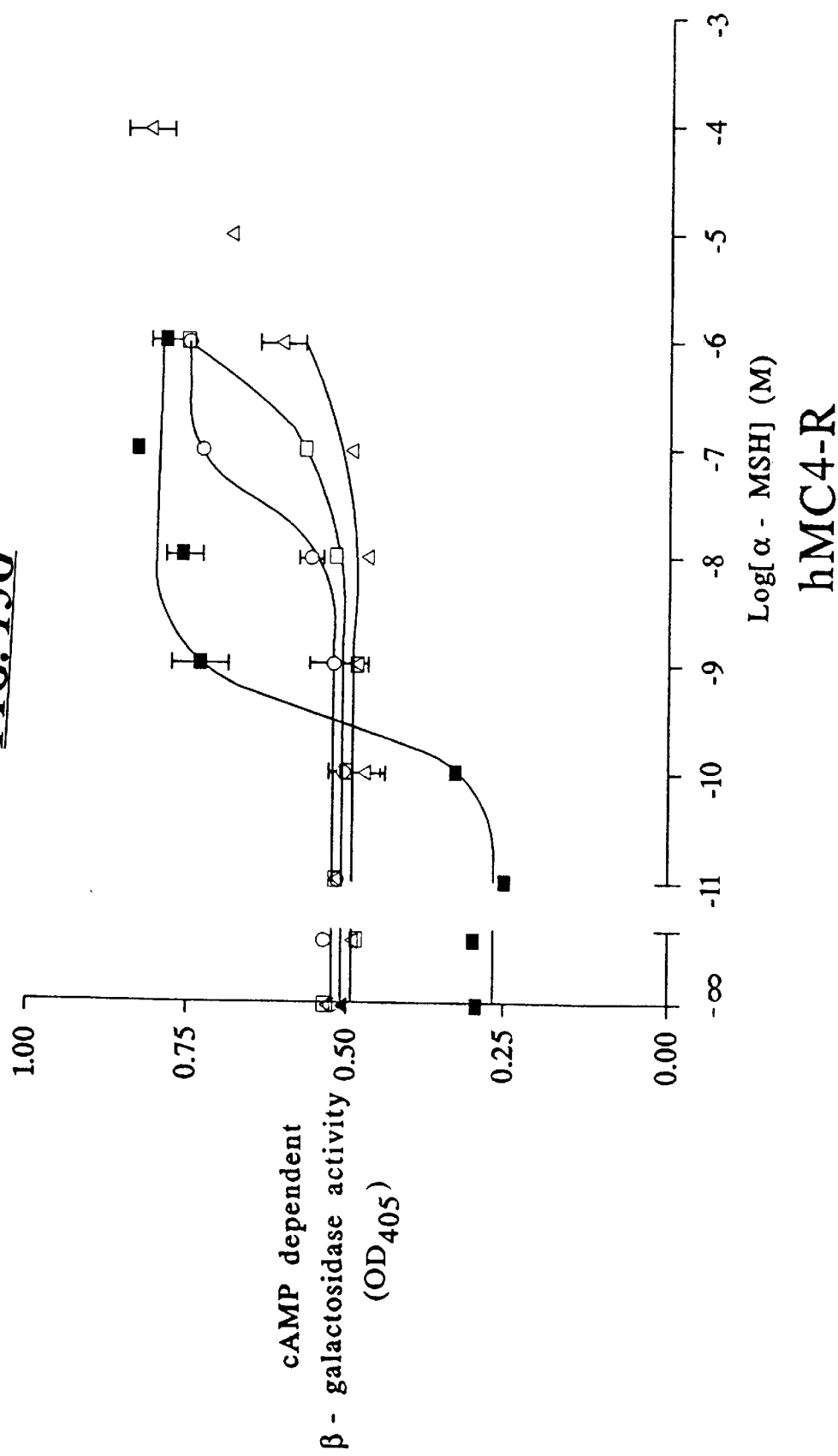

The results of these experiments are shown in FIGS. 15A and 15B. These Figures show the results of a β-galactosidase assay described above using cells expressing each of the MC1-R, MC3-R, MC4-R or MC5-R receptors and contacted with αMSH or a variety of αMSH analogues. These results showed that a particular MSH analogue (termed SHU9119; see co-owned and co-pending U.S. Ser. No. 08/706,281, filed Sep. 4, 1996, incorporated by reference herein) had relatively weak agonist activity for both human MC3-R and MC4-R receptors.

These results demonstrated the development of a colorimetric assay for cAMP accumulation as the result of melanocortin receptor binding by agonists or antagonists.

EXAMPLE 4

Preparation of Recombinant Targeting Vectors for Producing Mice Bearing a Homozygous Disruption of the MC5-R Gene Locus The cloned mouse MC5-R gene disclosed in Example 2G above was used to prepare recombinant genetic constructs for producing mice bearing homozygous disruption of the MC5-R gene locus as follows.

The purified MC5-R lambda genomic clone disclosed above contains the entire coding sequence, plus 5 kb of 5' noncoding sequence, as well as 7.8 kb of 3' noncoding sequence. A 9 kb SacI fragment was subcloned from the lambda genomic clone, shown schematically in FIG. 16, for subsequent manipulations. To make the "knock-out" construct, a 650 bp Apa I/MscI fragment that extends from −200 bp upstream (5') of the initiation codon to the middle of the TM3 domain of the receptor (at position 402 in SEQ ID No.:17) was replaced with the PGK-Neo cassette (as described in Rudnicki et al., 1992, Cell 71:383–390). The PGK-TK cassette (Rudnicki et al., 1992, ibid.) was placed 5' to the MC5-R coding sequence and with a transcriptional orientation opposite to the MC5-R gene sequences. The PGK-TK cassette was included in the construct to enrich homologous recombinants by negative selection against the thymidine kinase from herpes simplex virus (see Capecchi, 1989, Science 244:1288–1292). The resulting vector, termed pMC5-RKO thus contains 4.5 kb of MC5-R specific sequences derived from the 5' noncoding sequence of the cloned gene, and 1.2 kb comprising about 600 bp of MC5-R coding sequence and 600 bp of 3' untranslated sequences that are potential sites for gene disruption homologous recombination. The targeting construct can be linearized with XhoI.

EXAMPLE 5

Figure 16:
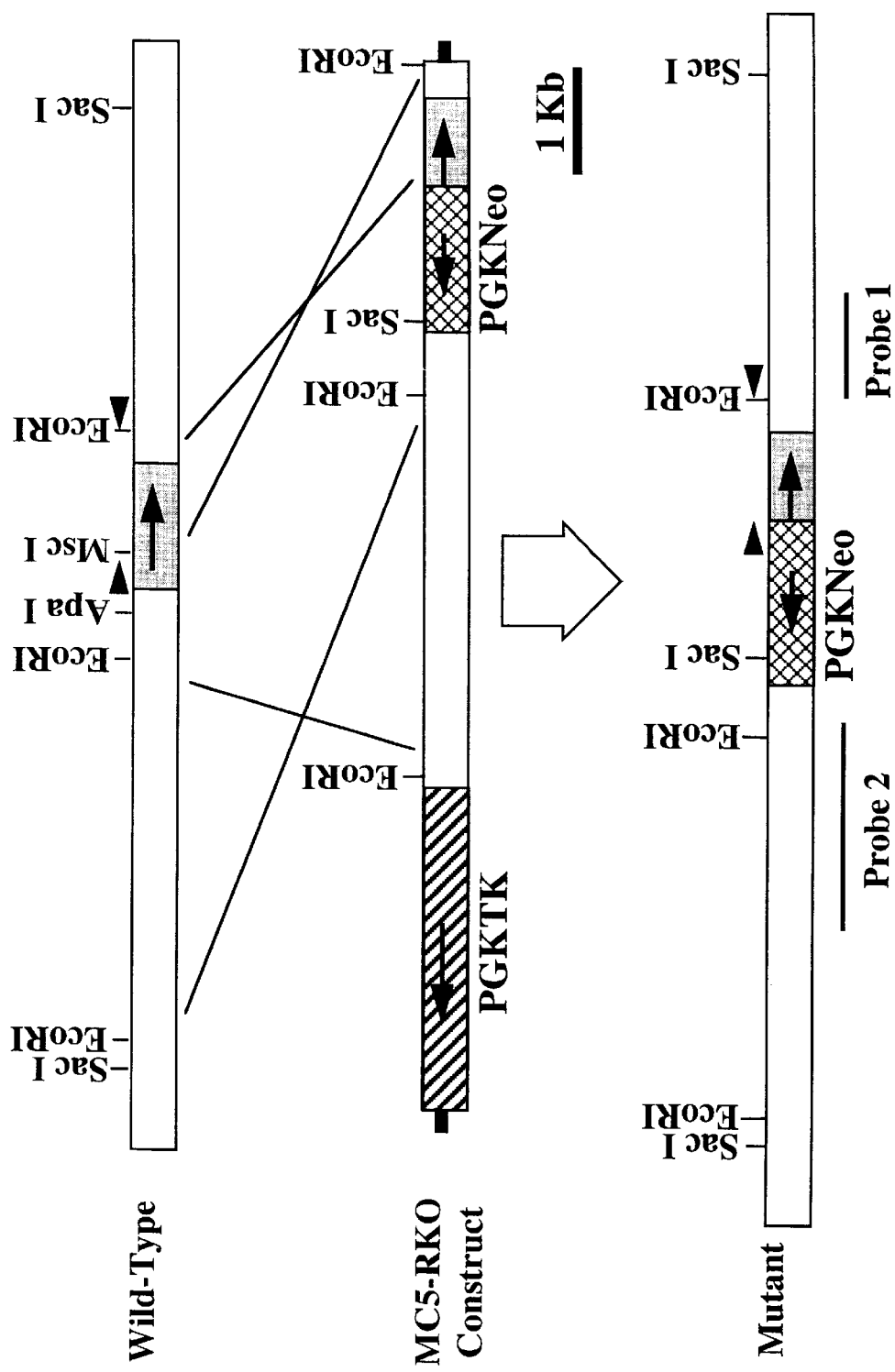
FIG. 16 shows a schematic drawing of the "knockout" construct described in Example 5. The shaded box in the wild-type allele represents the single coding exon of the murine MC5-R, with arrows in the boxes indicating the orientation of transcription. Small arrows above the boxes in the wild-type and mutant alleles stand for the sequences used as PCR primers for genotyping. The schematic drawing labeled "Mutant" shows the arrangement of mouse chromosomal sequences and pMC5-RKO sequences in homologous recombinant bearing mice. The sequences labeled "Probe 1" and "Probe 2" correspond to the probes used in Southern analysis of homologous recombinant bearing mice.

Use of Recombinant Targeting Vectors for Producing Mice Bearing a Homozygous Disruption of the MC5-R Gene Locus 1. Transfection of ES cells and blastocyst injection Twenty-five μg of XhoI-linearized pMC5-RKO DNA was electroporated into $10^7$ AK47 ES cells (which can be obtained, for example, from the American Type Culture Collection, Rockville, Md.). The cells were selected with G418 (400–1000 μg/mL) and gancyclovir at 24 hour after transfection. Individual colonies were identified one week after selection and expanded in 96 well plates. DNA from individual clones was screened by PCR analysis for homologous recombinants, using one primer specific for sequences outside of pMC5-RKO:

5'-CTAGGATAGGGGAACTGTAGT-3' SEQ ID No.: 20
and one primer specific for sequences comprising the PGK-Neo cassette:

5'-GAGGATTGGGAAGACAATAGCA-3' SEQ ID No. 21
under PCR conditions essentially equivalent to those disclosed in Example 1. Positive clones were confirmed by Southern analysis using MC5-R flanking sequences from both the 5' and 3' extents of the MC5-R gene, each comprising a naturally-occurring EcoRI site as shown in FIG. 16 as a probe. About 20% of clones obtained were found to be homologous recombinants using these methods. Selected clones were injected into blastocysts from C57/BL/6 mice, prepared using standard techniques (see Hogan et al., 1986, *Manipulating the Mouse Ember: A Laboratory Manual*, Cold Spring Harbor Laboratory Press: New York), and several chimeric mice were produced. Three independent chimeric lines were found to be transmitted through germline. Chimeric male mice were then breed with C57BL/6 or 129Sv mice: one clone was bred with 129Sv to produce inbred offspring, and the other two were backcrossed 7–9 generations with C57BL/6J mice to make congenic strains. Germline transmission of the "knockout" allele comprising pMC5-RKO sequences was identified using PCR analysis as described for ES cell analysis and in addition using a wild-type specific primer:

5'-ATGAACTCCTCCTCCACCCTG-3' SEQ ID No.: 22
and confirmed by Southern analysis. Heterozygotic males and females were breed to generate homozygous mutant mice. Continuous backcrossing with C57/BL/6 was carried out to obtain C57/BL/6-like congenic lines.

Figure 17A:
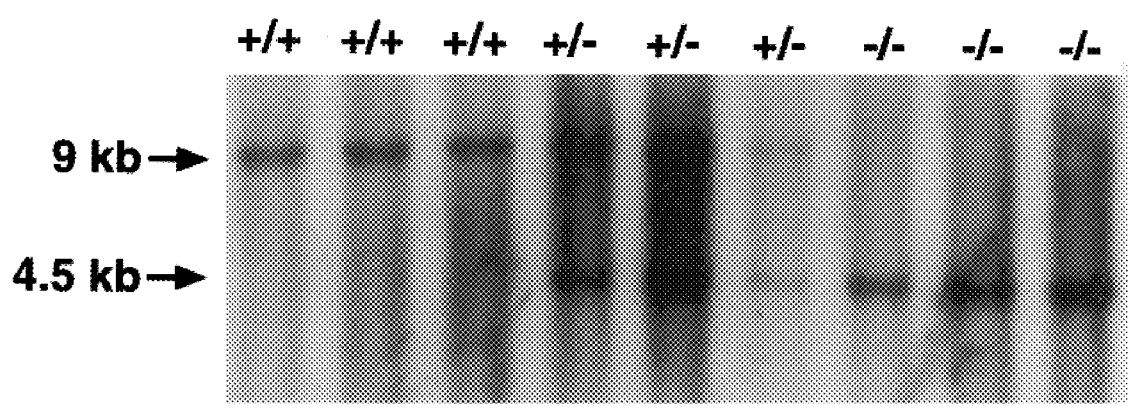
FIGS. 17A and 17B shows the results of Southern analysis from different genotypes of F1 offspring using Probe 1 and Probe 2 shown in FIG. 16. Genomic DNA of 21-day old progeny mice were isolated and their genotypes were determined using the mixture of three PCR primers as indicated in FIG. 16 and described in Example 5. Ten µg of DNA from putative wild-type, heterozygous and homozygous mutant mice was digested with Sac I for Southern analysis with probes 1 and 2. A 4.5 kb band shown in FIG. 17A and a 5.5 kb band shown in FIG. 17B represent the mutant, disrupted MC5-R allele.
Figure 17B:
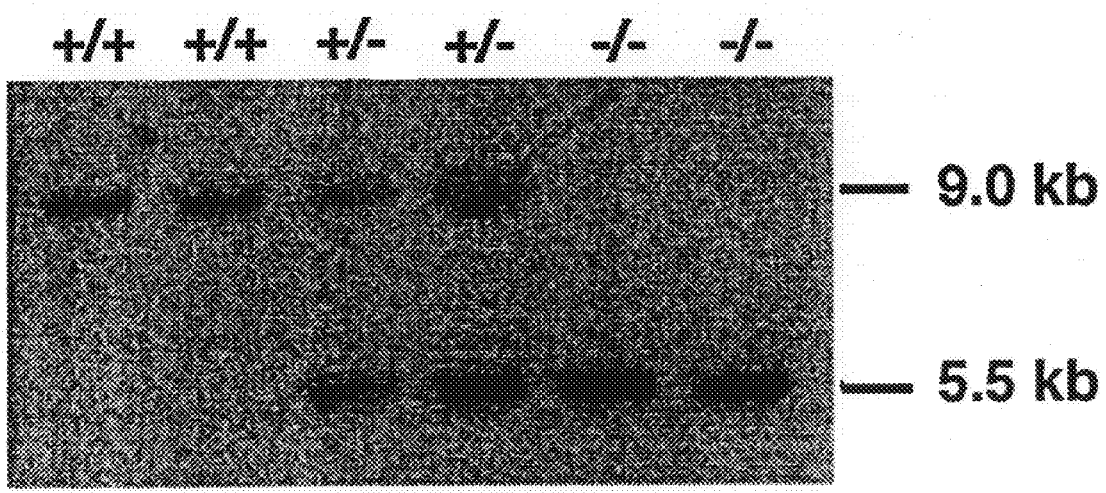
Figure 17C:
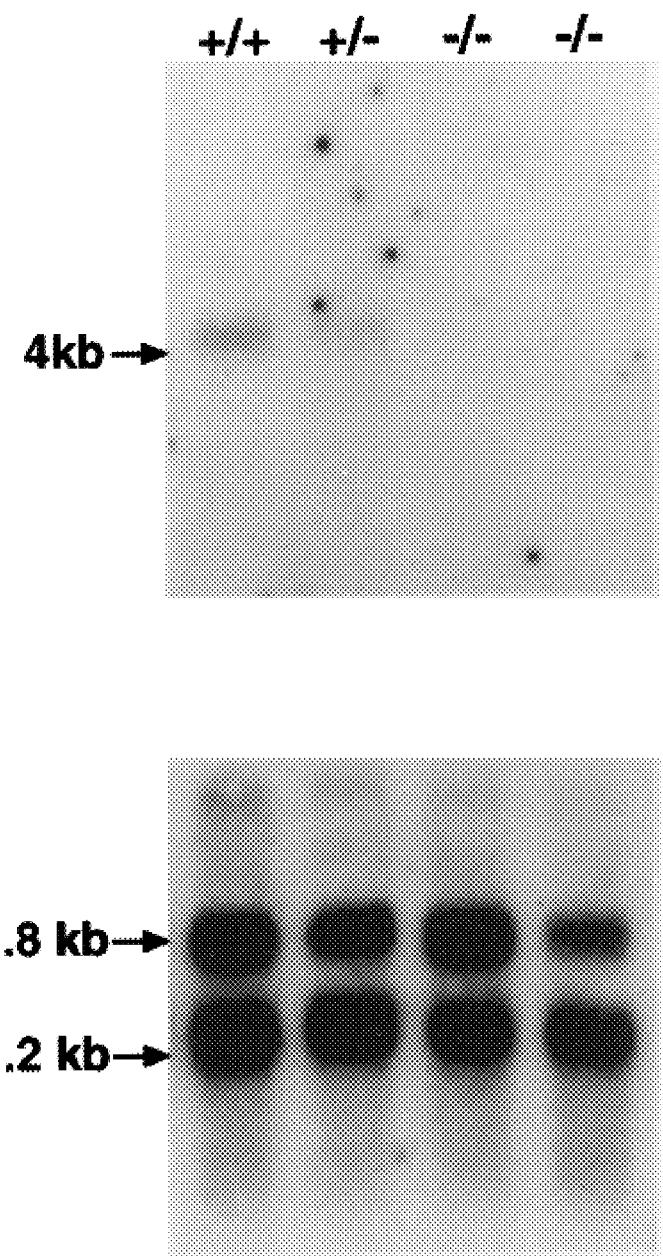
FIG. 17C shows the results of northern analysis of MC5-R mRNA expression in skeletal muscle tissue. Poly A⁺ mRNA from 250 1g of total RNA was loaded in each lane. After electrophoresis and transfer, the membrane was probed with a radioactively-labeled probe comprising a 650 bp Apa I/Msc I fragment.
Figure 17D:
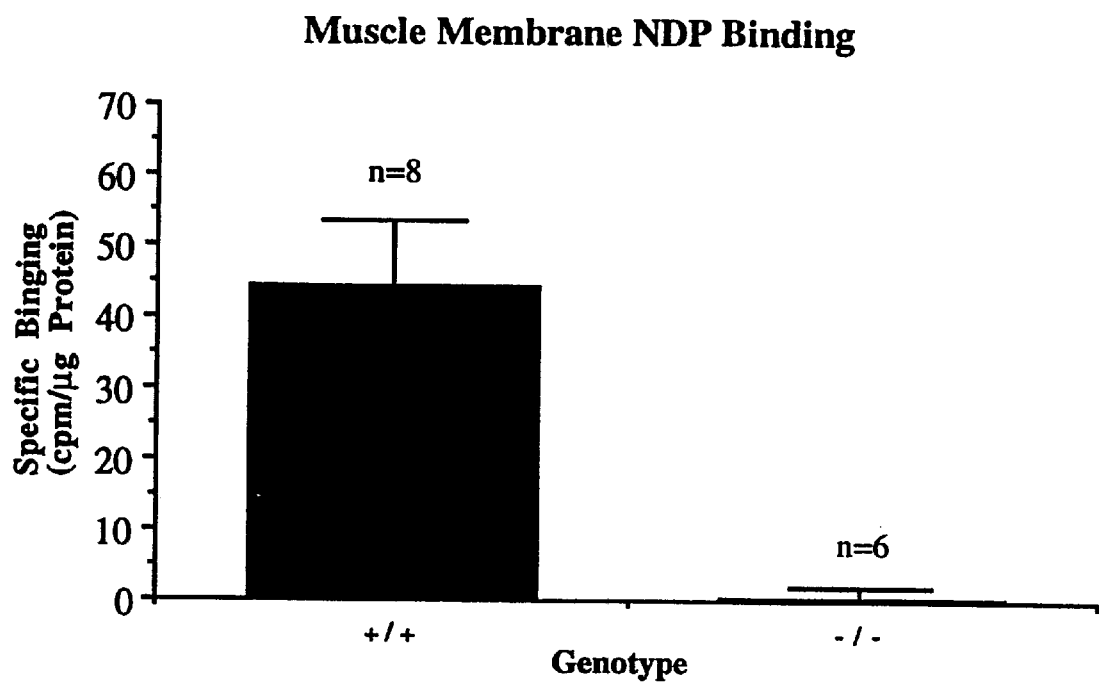
FIG. 17D shows radioligand binding to skeletal muscle membranes. Fresh skeletal muscles of the hind limbs from individual mice of each genotype were minced, homogenized, and crude plasma membranes isolated as described in Example 5. Total and non-specific binding was measured after incubation of the membranes with $^{125}$I-DMP-α-MSH (10,000 cpm/sample) in the presence or absence of 1 µM α-MSH. After extensive washing, specific binding was calculated and normalized to total protein.

The deficiency of MC5-R was confirmed by Southern hybridization (FIGS. 17A and 17B), northern analysis (FIG. 17C) and $^{125}$I-Nle$^4$, D-Phe$^7$-α-MSH (NDP-α-MSH) binding on crude plasma membranes from skeletal muscle (FIGS. 17D and 17E). MC5-R null mice were found to reproduce and thrive normally. There was no obvious anatomic or behavioral abnormalities in these mice, indicating that MC5-R expression is not essential for normal development and daily life under laboratory conditions.

2. Water retention assay and temperature measurement

Homozygous MC5-R "knockout" mice were analyzed to determine the physiological effects of homozygous MC5-R gene disruption using a variety of behavioral and physiological tests; in the absence of gross developmental or physical deformities, it was recognized that these effects could be subtle. No readily visible phenotype was apparent in mice bred to contain a homozygous deletion of the MC5-R, in either the C57B1/6J or 129Sv strain backgrounds. Appearance, behavior, growth, muscle mass, adipose mass, reproduction, and basal and stress-induced corticosterone, glucose, and insulin levels in these animals were indistinguishable from heterozygous or wild-type litter mates.

In order to identify more subtle physiological phenotypes in these "knockout" mice, the animals were examined for their response to exogenous melanocortin peptides in a number of adrenocortical-independent biological assays. Melanocortin peptide activities examined included anti-inflammatory activity of a-MSH in carageenan-induced ear-swelling (Macaluso et al., 1994, *J. Neurosci.* 14:2377–2382), enhanced recovery from sciatic nerve crush by α-MSH (Bijlsma, 1983, Eur. J. Pharmacol. 92:231–236; Strand et al., 1993, *Rev. Neurosci.* 4:321–363), and α-MSH induced inhibition of stress-induced analgesia (Belcher et al., 1982, *Brain Res.* 247:373–377; Smock and Fields, 1981, *Brain Res.* 212:202–206). The anti-inflammatory action of α-MSH is preserved in these mice, indicating MC5-R is not essential for this function. The mutant mice also have an apparently intact hypothalamic-pituitary-adrenal axis, suggesting MC5-R in the adrenal cortex is not essential for the stress response. Mutant mice were also indistinguishable from wild-type mice in swim-induced analgesia, excluding the involvement of MC5-R in the proposed inhibition of morphine-induced analgesia by ACTH (as suggested by Smock and Fields, 1981, ibid.). In summary, none of these assays produced identifiable differences between the wild type and knockout animals.

Figure 18A:
FIGS. 18A through 18F show defects in water repulsion and thermoregulation in MC5-RKO mice.
Figure 18B:
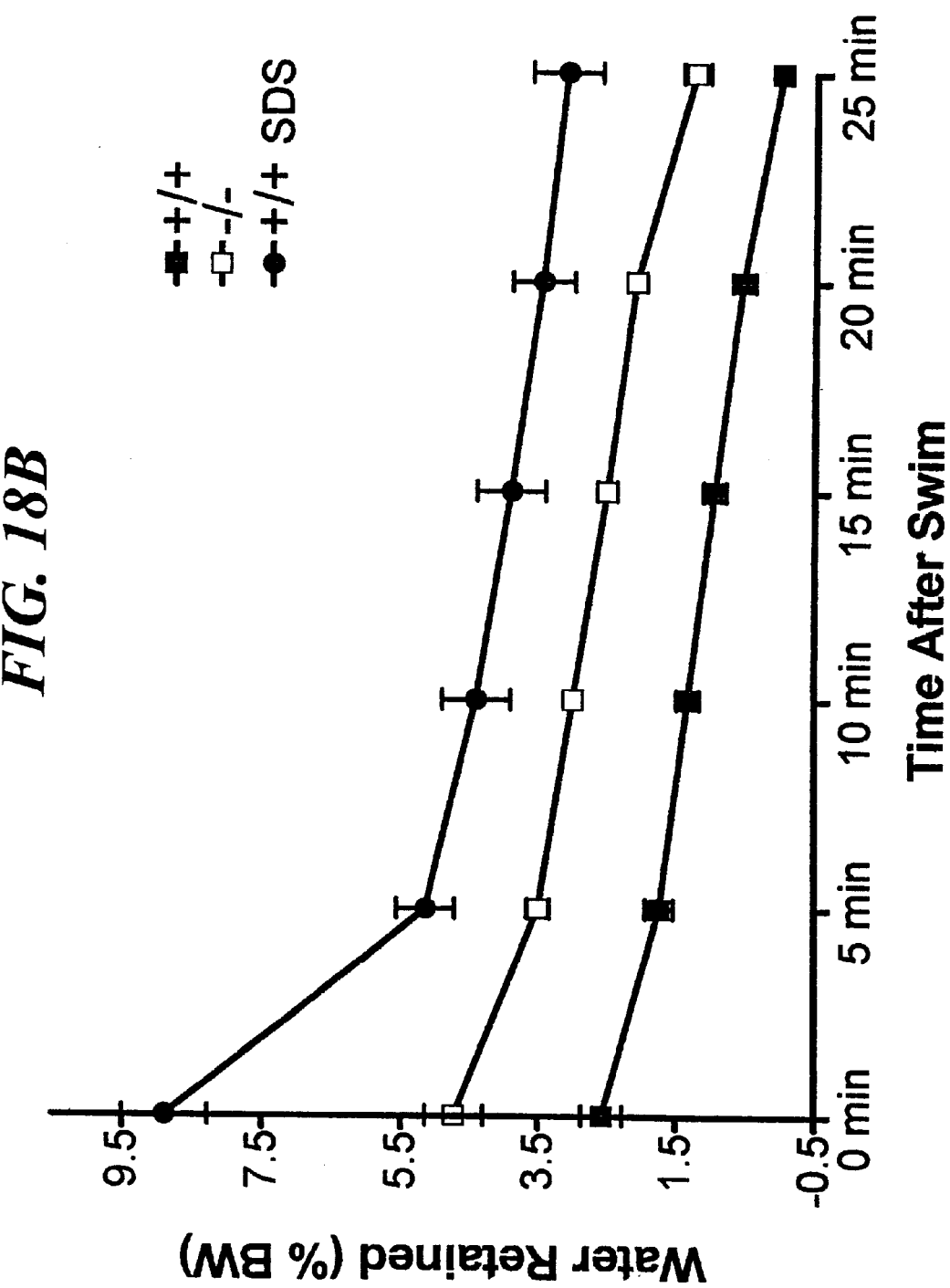
Figure 18C:
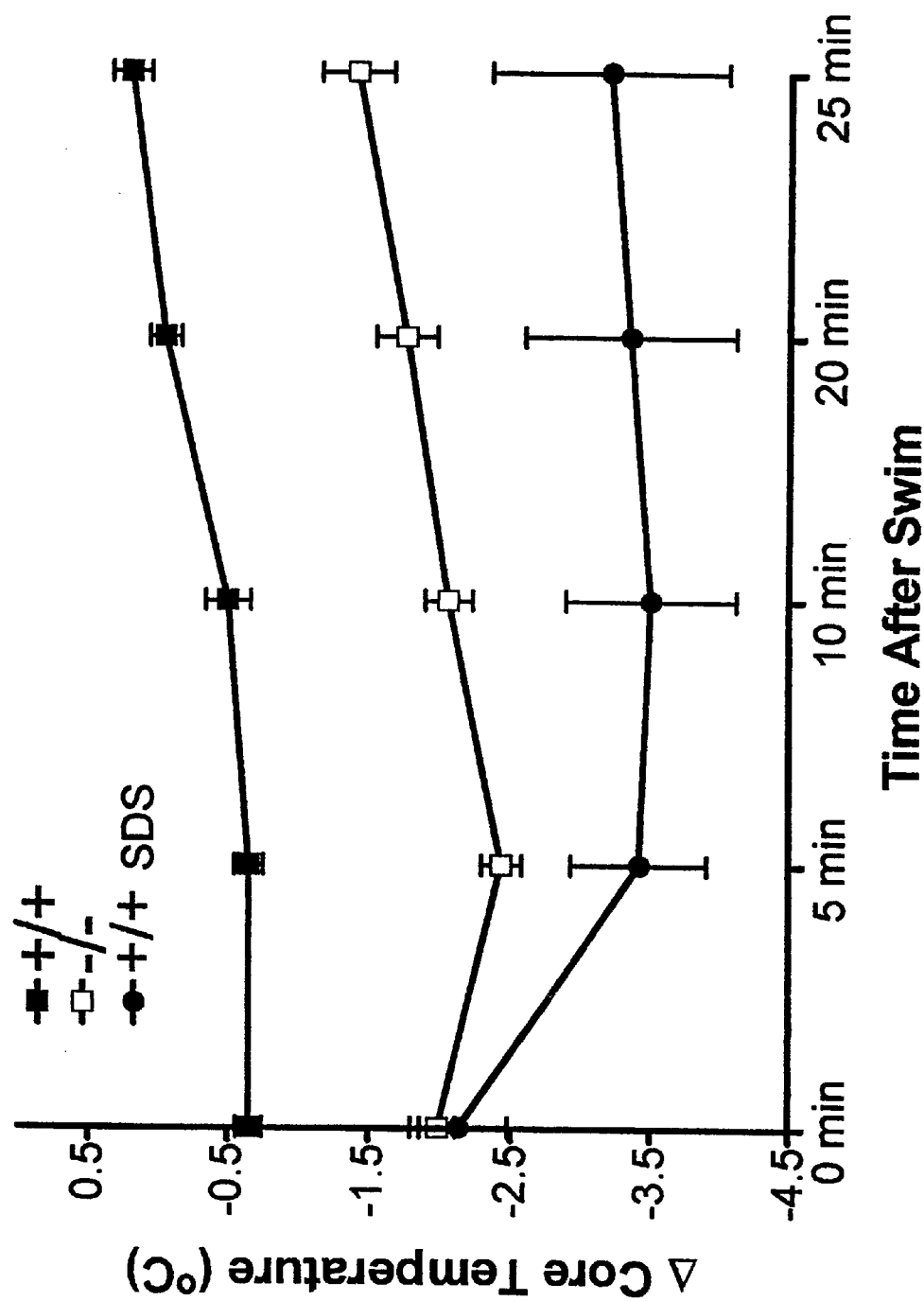
Figure 18D:
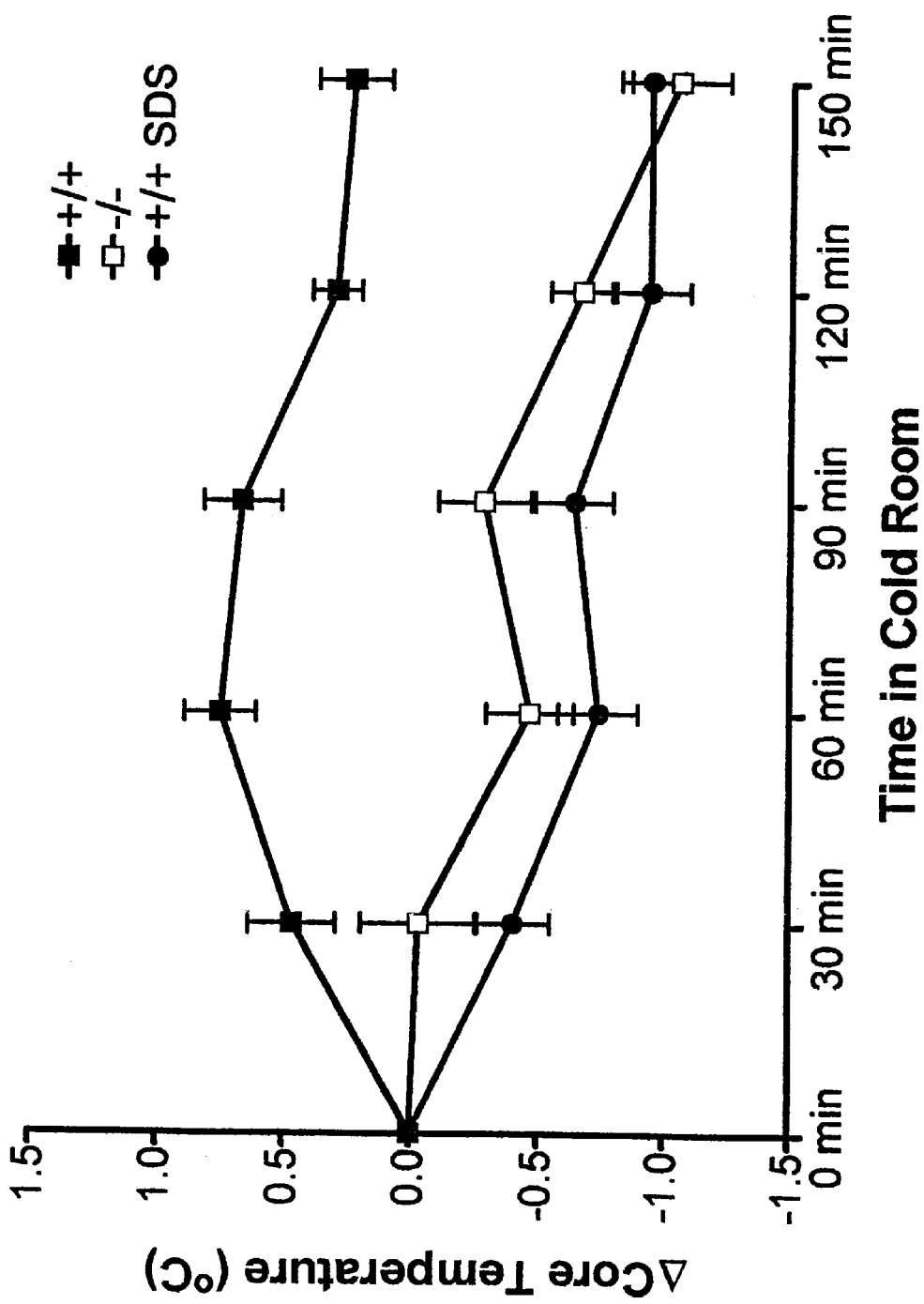

During a stress-induced analgesia assay in which the mice were made to swim for three minutes to activate the hypothalamic-pituitary-adrenal axis (Mogil, 1996, *Physiol. Behav.* 59:123–132), it was observed that the knockout animals had absorbed more water, needed more time for their fur to dry than their wild-type counterparts, and remained wet for a longer period of time than litter mate controls (shown in FIGS. 18A and 18B). This effect was then quantitated, and it was found that wild-type mice dried their hair in about 25 minutes on average after a 3 minutes swim at 32° C.; in contrast, it took MC5-RKO mice more than 40 minutes to dry (shown in FIG. 18B), resulting in severe thermoregulatory defects in the animal as well (FIGS. 18C and 18D).

To investigate this behavior, homozygous MC5-R "knockout" mice were subjected to a water retention/body temperature assay as follows. Core temperature was measured using an inserted rectal thermoprobe 2.5 cm inside each mouse. Five to 10 minutes prior to swim, the core temperature of each mouse was read 3 times to obtain the baseline. Mice were then weighed and immediately let swim in 32° C. water for 3 minutes. Mice were then removed from the water and placed on absorbent paper towels for about 5 seconds to eliminate excessive water. Mice were then weighed, their core body temperature recorded, and put into an empty Plexiglas cage. Weight and temperature was measured every five minutes for half an hour thereafter. The weight of absorbed water was calculated by subtracting pre-swim weight from the post-swimming weight.

These results indicated that the longer drying times found in the "knockout" mutant mice was due to impaired water repulsion by mouse skin and hair. MC5-RKO mice absorbed almost twice as much water as the wild type controls (results shown in FIG. 18B). The water absorbed by MC5-RKO mice totaled about 5% of their body mass, while that absorbed by wild-type controls amounted to only 2.5%. (The rate of evaporation, however, was comparable.) This defect in water repulsion appeared to be related to surface lipids, as shown by a reconstitution experiment using wildtype mice. Removal of skin and hair lipids from normal mice by washing the mice with a 5% SDS solution (termed "shampooed" mice) increased water absorption to 9% of body weight in wild type mice (see FIG. 18B), similar to the levels found in MC5-R knockout mutant mice.

These initial results prompted investigations on thermoregulation in the mice. Thermoregulation is a complex process involving many physiological responses including basal metabolic rate, vasodilation and constriction, shivering, non-shivering thermogenesis mediated by brown fat stores, sweating, panting, and lastly, insulation via the skin and coat. In addition to their obvious role in repelling water, dermal lipids (such as are produced by the sebaceous and Harderian glands) are critical for supporting the optimal insulating capabilities of the mammalian coat. For example, removal of the Harderian gland, a large bi-lobed gland found in the retroorbital region in most vertebrates, results in approximately 40–50% reduction in lipids extractable from the coat (Thiessen and Kittrell, 1980, *Physiol. Behav.* 24:417–424). This, in turn, results in a dramatic thermoregulatory defect in the gerbil (Thiessen and Kittrell, 1980, ibid.), reducing core body temperature 4.6° C. in response to a cold water bath in the Harderianectomized animal compared to 1.6° C. in the sham operated control. Likewise sebaceous lipids play an important thermoregulatory role, as has been demonstrated in the muskrats (Harlow, 1984, *Physiol. Zool.* 57:349–356).

The MC5-RKO and wild type animals had the same core body temperature at an ambient temperature at 26° C. However, the colonic temperature decreased 2° C. during a 3 minute swim at 32° C. in mutant mice, compared to 0.7° C. in the wild-type controls. In addition, colonic temperature dropped another 0.5° C. before the mutant mice recovered. No further decline in body core temperature was observed in wild-type mice, whereas the colonic temperature in MC5-RKO mice was still 1.5° C. below normal. This more severe and longer lasting hypothermia could be mimicked in wild-type mice by washing the mice with detergent as above (see FIG. 18C).

Lipids in the mammalian coat were also found to be important for optimal regulation in cold air as well as cold water. Mutant and wild-type mice were challenged with cold air (using a cold room held at 5–6° C.), and mutant and wild-type exhibited remarkable differences in their colonic temperature. Wild-type mice increased core temperature slightly at the beginning of the cold room incubation, and maintained above-normal body temperature for at least 3 hours. In contrast, MC5-RKO bearing knockout mice underwent a mild hypothermia (shown in FIG. 18D). As before, air hypothermia could be produced in wild-type mice by removing surface lipids with a 5% SDS solution (see FIG. 18D). These results suggested that MC5-RKO knockout mice differing from their litter mates solely by virtue of homologous genetic disruption of the MC5-R gene locus resulted in an impairment in water repulsion as well as a defect in the insulating properties of the coat in the mutant mice due to a deficiency in the production secretion or distribution of hair and/or skin lipids.

3. Hair lipids extraction and analysis

The results shown in Section 2 above prompted an analysis of hair lipids from wild-type and MC5-RKO mutant mice as follows.

Hair lipids were extracted as described by Ebling (1975, *J. Endocrinol.* 66:407–412) with modifications. Seventy to 100 mg of hair from each mouse was extracted with 20 mL of acetone for 15 minutes. The extractants were filtered and the hair was then washed with an additional 20 mL acetone. The pooled filtrant was let evaporate to about 5 mL in a chemical hood. The acetone was then transferred to a tared aluminum foil boat and evaporated to dryness. The aluminum foil was then reweighed. The amount of hair lipids obtained using this procedure was calculated by subtracting the predetermined weight of the foil from the weight obtained after evaporation of the lipid-extracting acetone, Hair lipids (100–150 $\mu$g) were recovered from the aluminum foil, loaded on a Silica gel 60 plate (Aldrich, Milwaukee, Wis.) and resolved by hexane/benzene (55:45 v/v). The positions of the lipids on the plate were developed by spraying the plate with sulfuric acid/ethanol (1:1) mixture, then charred in an 150° C. oven until appropriate color development occurred (as described by Stewart & Downing, 1991, *Adv. Lipid Res.* 24:263–301).

Figure 18E:
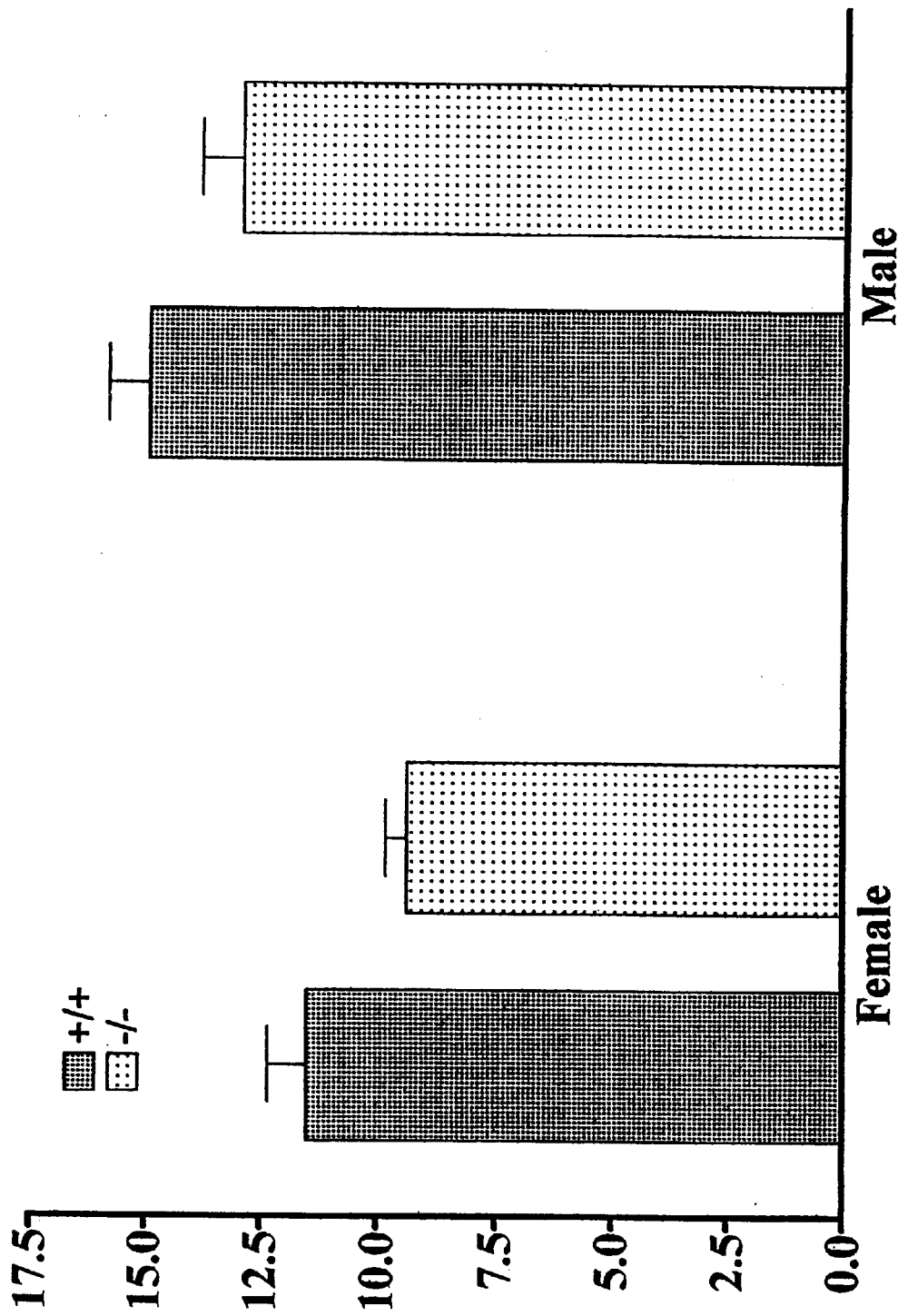

A 15–20% reduction of acetone-extractable material from hair lipids was found in both male and female MC5-RKO mice (shown in FIG. 18E). It was recognized that it is not unexpected to observe reduced sebum production by females because sebaceous gland activity is up regulated by androgens (found in greater concentrations in males; Thody et al., 1976, *J. Endocrinol.* 71:279–288). In order to determine whether the observed results represented a general or specific deficiency, surface lipids were analyzed by thin layer chromatography (TLC). A dramatic reduction of sterol esters in both male and female mutants was observed (FIG. 18F).

Figure 18F:
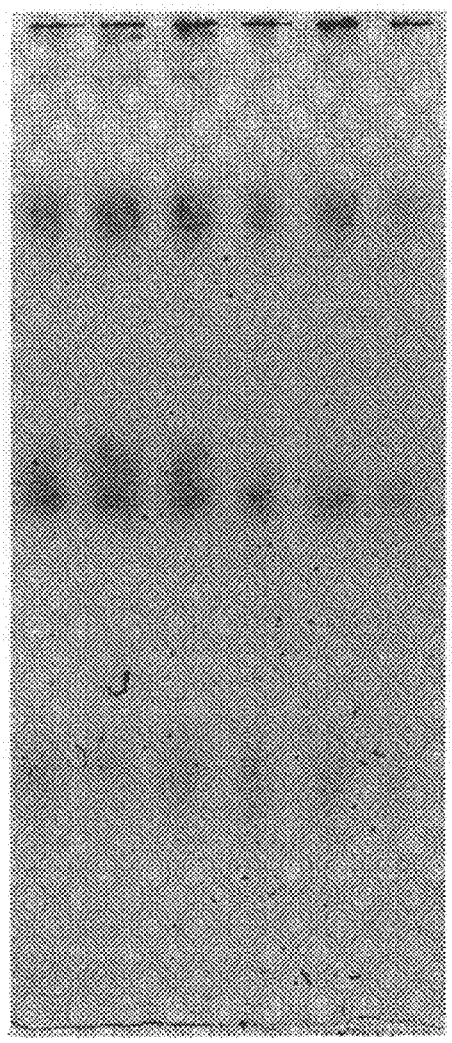

Sterol esters constitute more than 26% of the total acetone extractable lipids in wild-type mice, but only about 13% in the mutants (FIG. 18F). There was no other significant difference in other sebum components. As sterol esters are the most hydrophobic species of sebaceous lipids, their deficiency is consistent with impaired water repulsion seen in MC5-RKO mice.

4. MC5-R receptor expression in exocrine glands

A. The MC5-R receptor is expressed at high levels in multiple exocrine glands

The defect observed in MC5-RKO mutant mice disclosed above suggested a direct role for MC5-R receptor in sebaceous gland production. Expression of MC5-R receptor in sebaceous or other exocrine glands as not been previously reported. In order to assay for MC5-R expression in exocrine, specifically sebaceous, glands, in situ hybridization was performed on skin sections from wild-type mice, using a radiolabeled 650 bp ApaI/MscI MC5-R fragment as a probe (see FIG. 16). Results of these assays are shown in FIG. 19A, Panels A through D. Highly-abundant expression of MC5-R mRNA was found in hair follicle-associated sebaceous glands in wild-type skin (FIG. 19A, Panel A and Panel C), but not in MC5-RKO mutant mice (FIG. 19A, Panel B). Specificity of the observed hybridization was confirmed by performing in situ hybridization on wild-type skin sections using a sense-oriented MC5-R probe (FIG. 19A, Panel D).

Figure 19B:
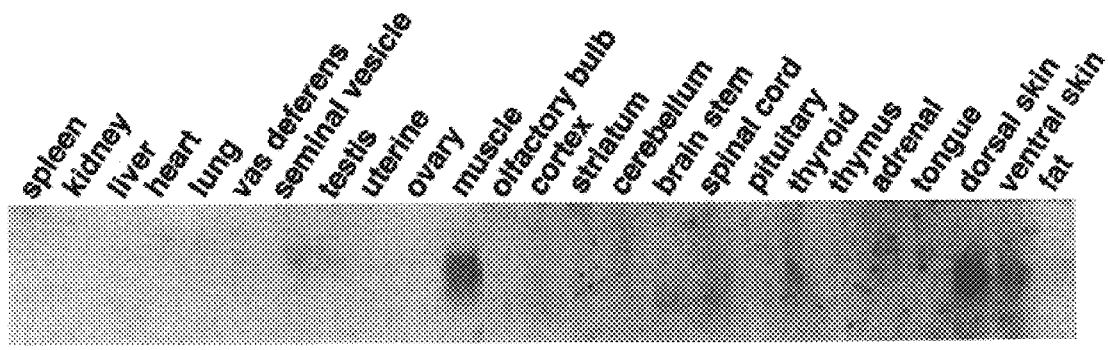
Figure 19C:
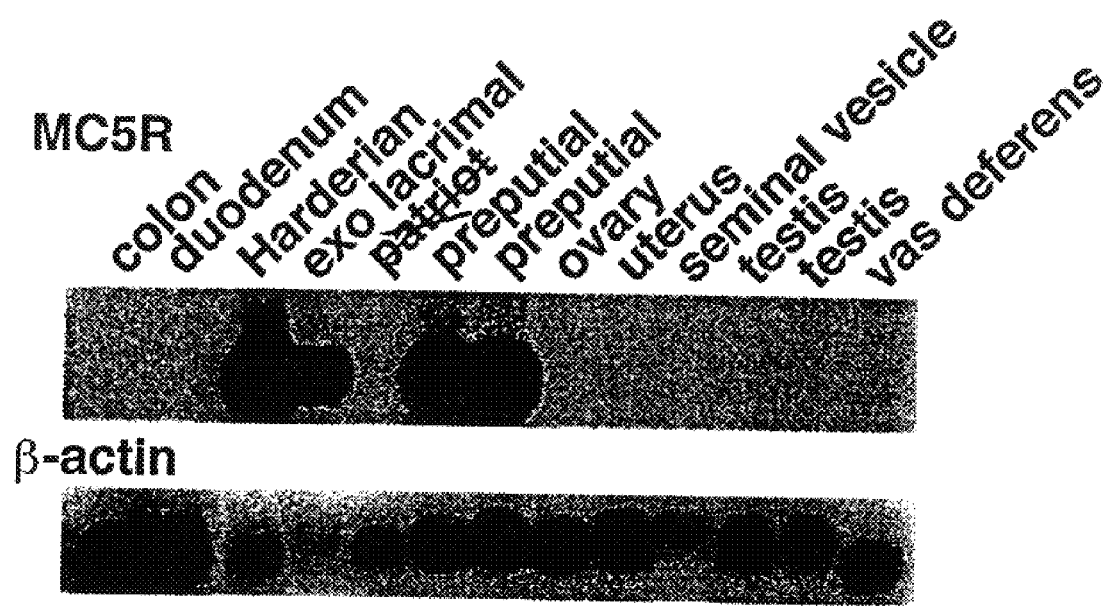

In view of the results disclosed above, and in view of previously disclosed findings that suggested an effect of αMSH on sebum production, the finding of MC5-R mRNA in sebaceous gland inspired a comprehensive search for MC5-R expression in other exocrine tissues including preputial gland (a specialized sebaceous gland), lacrimal gland and Harderian gland, as well as in a variety of previously-characterized tissues. In agreement with previous studies, MC5-R mRNA was detected at moderate levels in muscle and skin, and was present at very low levels in spinal cord, brain stem, and adipose tissues (FIG. 19B). Strikingly, however, MC5-R mRNA was found to be extremely abundant in the Harderian gland, lacrimal gland and preputial gland (FIG. 19C). The level of MC5-R in preputial gland is approximately 30 times higher than that in the skin (comparison shown in FIG. 19D).

B. Functional MC5 receptor protein is expressed in multiple exocrine glands and in spinal cord—Characterization of functional membrane receptor The results disclosed above demonstrated MC5-R mRNA expression in exocrine glands of wild-type mice and not of MC5-RKO knockout mutant mice. To further and complement analysis of the differences between wild-type and MC5-RKO mutant knockout mice, various exocrine glands and tissues were surveyed for functional MC5-R gene expression by performing agonist binding studies on membrane preparations. In these experiments, crude membranes were made from wild-type and "knockout" mouse exocrine glands and tissues as follows. Tissues were minced and homogenized with a Polytron. The homogenized tissue mixture was then subjected to 500×g by centrifugation, and the resulting supernatant fluid of the tissue homogenate was then centrifuged at 100,000×g for 40 minutes at 4° C. The pellet was rinsed twice with PBS and protein content determined using the method of Bradford (1976, *Analyt. Biochem.* 72:248–254). Specific $^{125}$I-NDP-α-MSH binding by membrane preparations containing 100 ug of protein was determined as described in co-owned U.S. Pat. No. 5,532,247, issued Jul. 2, 1996, incorporated by reference herein. To monitor ligand-induced cAMP production, excised tissues of interest were minced and incubated in DMEM containing 0.1 mg/mL BSA in the presence or absence of ligand for 20 minutes before being frozen in liquid nitrogen. cAMP was extracted with 60% ethanol and measured by RIA as described (Chen et al., 1995, ibid.). Protein in ethanol extracted pellets was determined by the method of Bradford as above. Protein assay studies were complemented by northern analysis of tissue-extracted mRNA in tissues showing differential MC5-R gene expression in wild-type and MC5-RKO mutant mice.

Figure 20A:
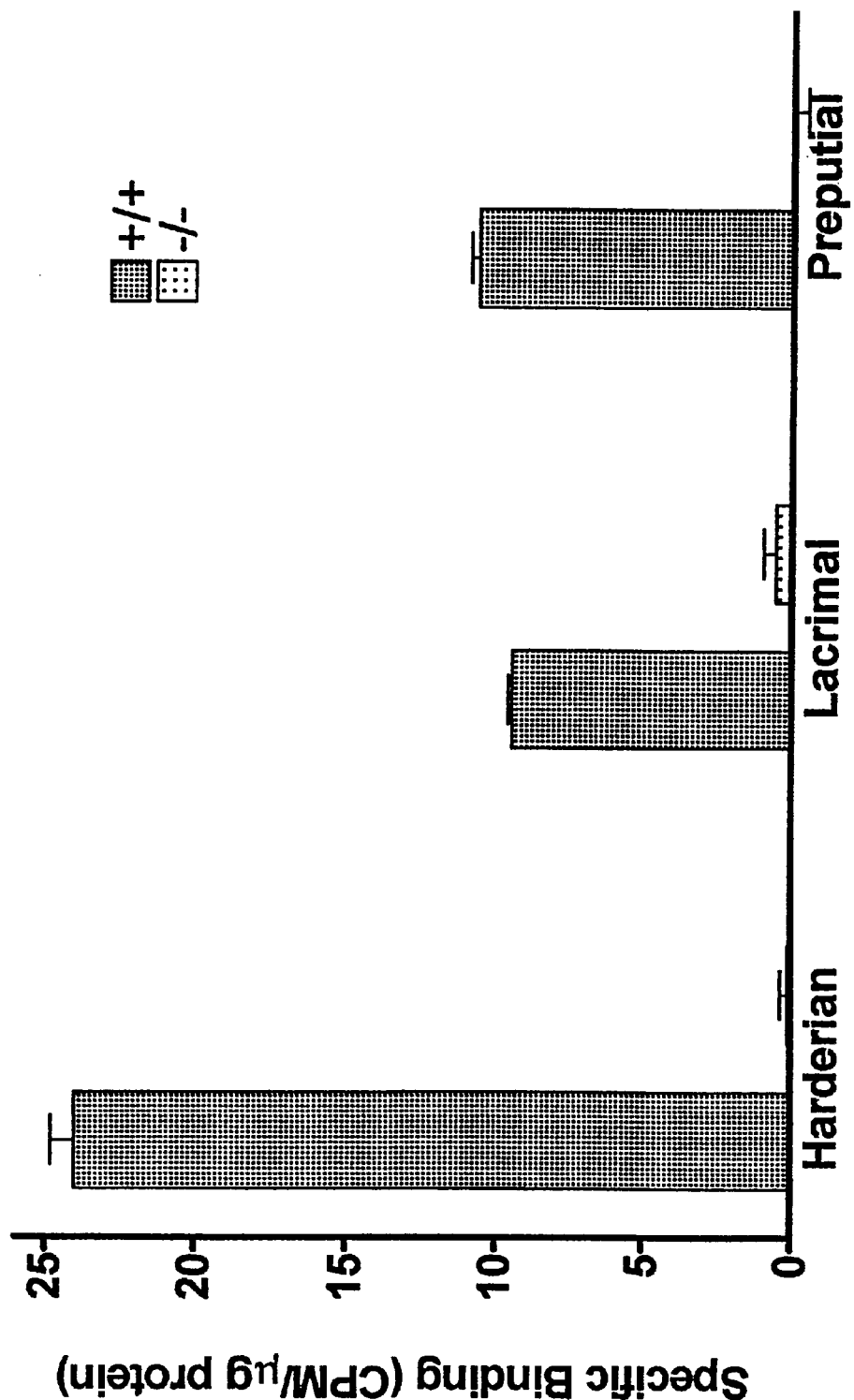
FIG. 20A through 20D illustrate that MC5-R is the only functional melanocortin receptor in several exocrine glands, and the primary melanocortin receptor in the spinal cord.
Figure 20B:
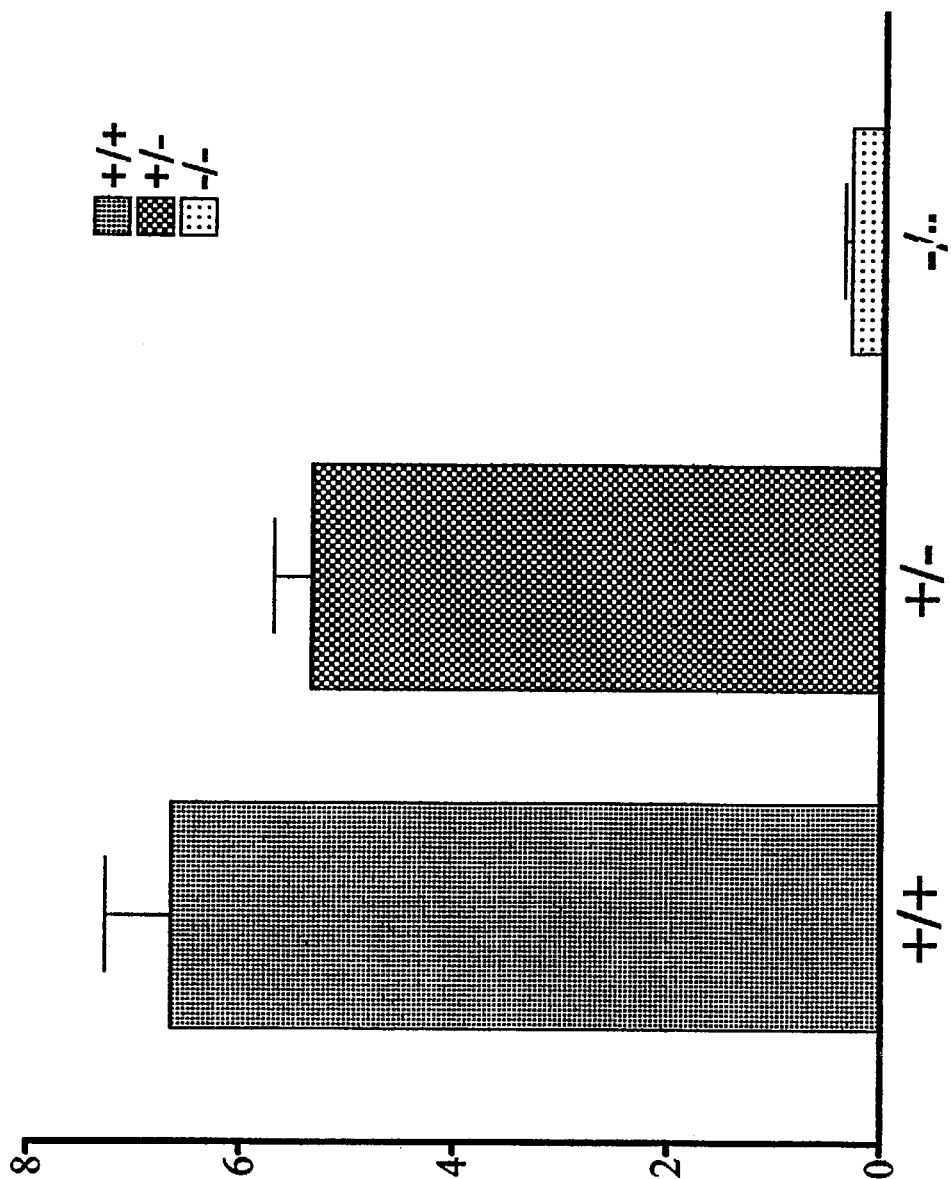

The results of these radioligand binding studies are shown in FIGS. 20A and 20B. As was previously observed in skeletal muscle membrane, there was strong and specific $^{125}$I-DNP-α-MSH binding in crude plasma membranes prepared from Harderian gland, preputial gland, and lacrimal gland of wild-type mice (FIG. 20A). When these binding experiments were conducted in membranes obtained from heterozygous MC5-RKO mice, intermediate levels of specific binding was found. Specific binding was absent in membranes from MC5-RKO mice, indicating the absence of significant levels of expression of MC1-R, MC3-R and MC4-R in these tissues (FIG. 20A).

Specific $^{125}$I-NDP-α-MSH binding was also seen in the spinal cord. The decreased binding in the heterozygotes and mutant mice indicates that MC5-R is the major melanocortin receptor in spinal cord (FIG. 20B). The residual binding may be due to MC4-R in this tissue.

Figure 20C:
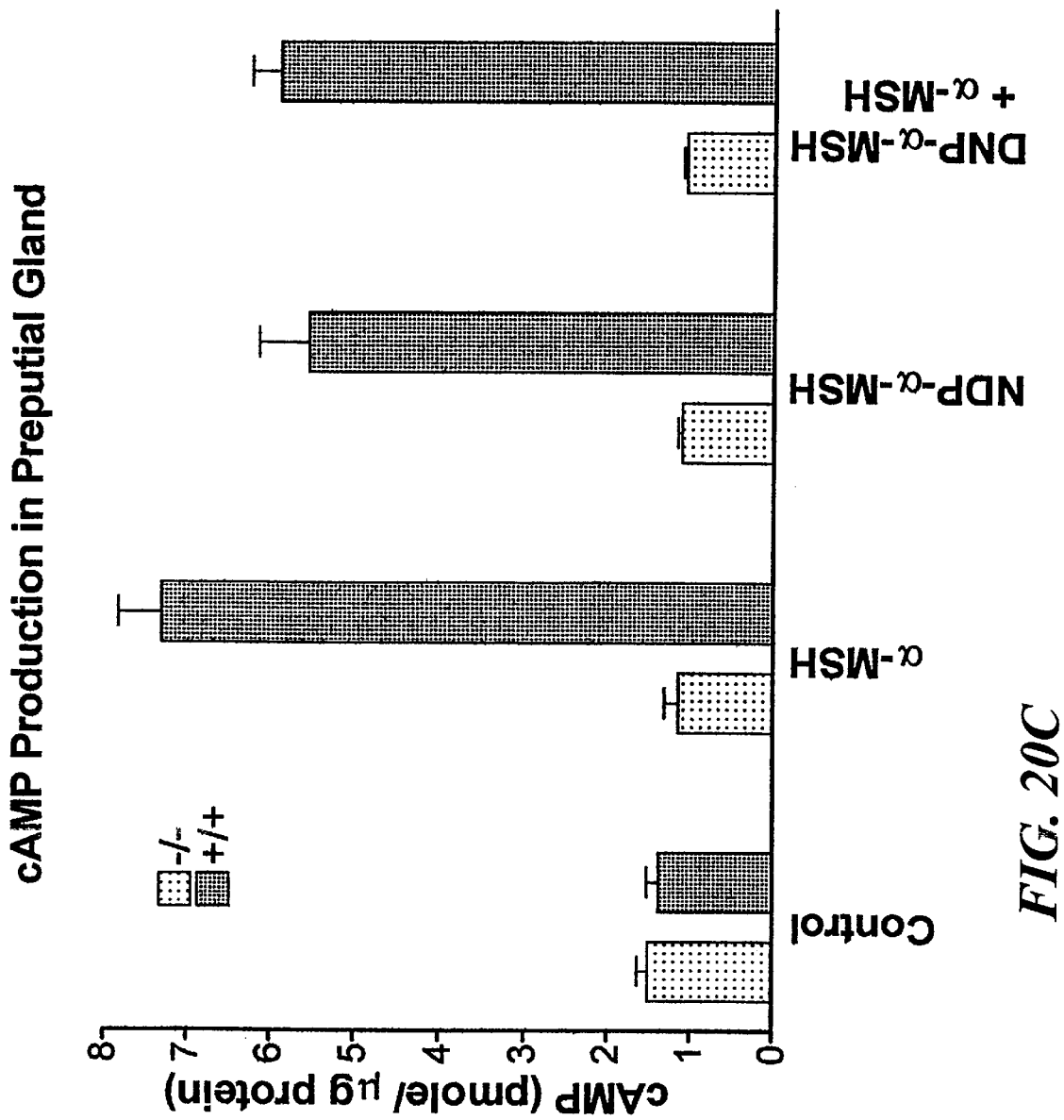
Figure 20D:
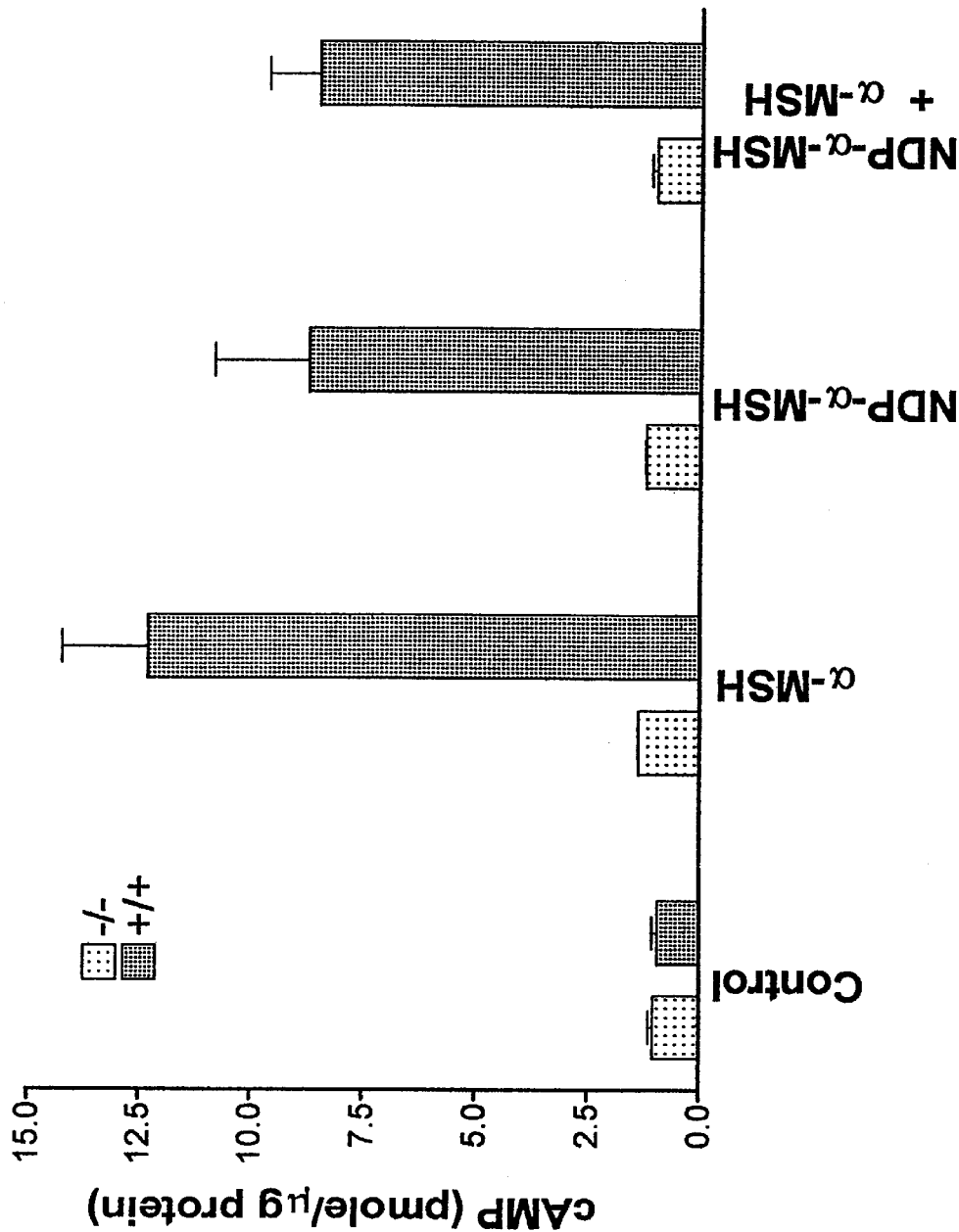

To further examine the functionality of the MC-5R receptor in these tissues, exocrine glands were exercised and cultured in vitro. Application of physiological levels of α-MSH and/or NDP-α-MSH to such cultures markedly stimulated cAMP synthesis in the cultures, further demonstrating the presence of functional receptor protein (as illustrated by preputial gland culture results, shown in FIGS. 20C and 20D). There was less stimulation of cAMP synthesis by the synthetic ligand NDP-a-MSH, suggesting that NDP-A-MSH may be a partial agonist at the MC5-R. This is consistent with data obtained from MC5-R expressed in HEK293 cells (Chen, unpublished data). The inhibition of α-MSH induced cAMP production by NDP-α-MSH suggests the compound may act as a mixed agonist/antagonist.

Thus, creation of the MC5-R knockout mouse disclosed herein permitted examination of the role of the MC5-R receptor in the in vivo expression of MSH binding sites, as assessed by the binding of radiolabeled $^{125}$I-NDP-a-MSH . Particularly striking was the high level of MC5-R binding sites expressed in spinal cord and skeletal muscle (FIG. 17D). These results suggest a role for the MC5-R receptor in mediating the effects of melanocortin peptides on nerve regeneration (Bijlsma, 1983, ibid), muscle satellite cell proliferation (Cossu, 1989, *Develop. Biol.* 131:331–336; De Angelis et al., 1992, *Develop. Biol.* 151:446–458), and muscle deuse deconditioning. These results also provide a pharmacological rationale for observed but unexplained regulation of the production of sebaceous and preputial lipids by exogenous A-MSH (Thody et al., 1976, ibid.).

5. MC5 Receptor Regulates Protein Secretion by the Lacrimal Gland

A. Measurement of lacrimal gland protein discharge

The lacrimal gland is the major source for the protein-rich aqueous layer of tear film. This gland is known to secrete both electrolytes and proteins, largely under parasympathetic control (Dartt, 1994, *Adv. Exp. Med. Biol.* 350:1–9). To assess the consequences of MC5-R ablation on lacrimal gland secretion, we measured melanocortin-stimulated protein secretion in the lacrimal gland fragments in culture.

Protein discharge from lacrimal glands was determined as described by Jahn (1982, ibid.). Mouse lacrimal glands were dissected and each cut into four pieces. The explants were incubated in 10 mL of Kreb-Ringer bicarbonate buffer (KRB) in the presence of 25 $\mu$Ci $^{3}$H-leucine for 20 minutes in a 37° C. chamber gassed with 5% $CO_2$ and 95% $O_2$. The tissues were rinsed three times with KRB and further incubated in KRB for 60 minutes to allow incorporation of radioactivity into protein. After another rinsing with KRB, 8 pieces of labeled tissue (corresponding to 2 glands) were put into one well of a 12-well plate, each well containing 2 mL of KRB. Buffer (0.5 mL) was taken from each well before returning the plate into the chamber. Fifteen minutes later, another 0.5 mL aliquot of buffer was removed from each well. Hormones to be tested were added to a final concentration of 50 nM, and the plate further incubated in the chamber for 30 minutes, after which time 0.5 mL of buffer was again removed from each well. Radioactivity produced in each sample was measured by liquid scintigraphy. The rate of protein discharge for each sample during the last 30 minutes of the assay was calculated as the net increase of radioactivity in the period divided by that in the previous 15 minutes. The relative secretion rate was computed by setting the rate of the wild-type control to be 1.

Figure 21A:
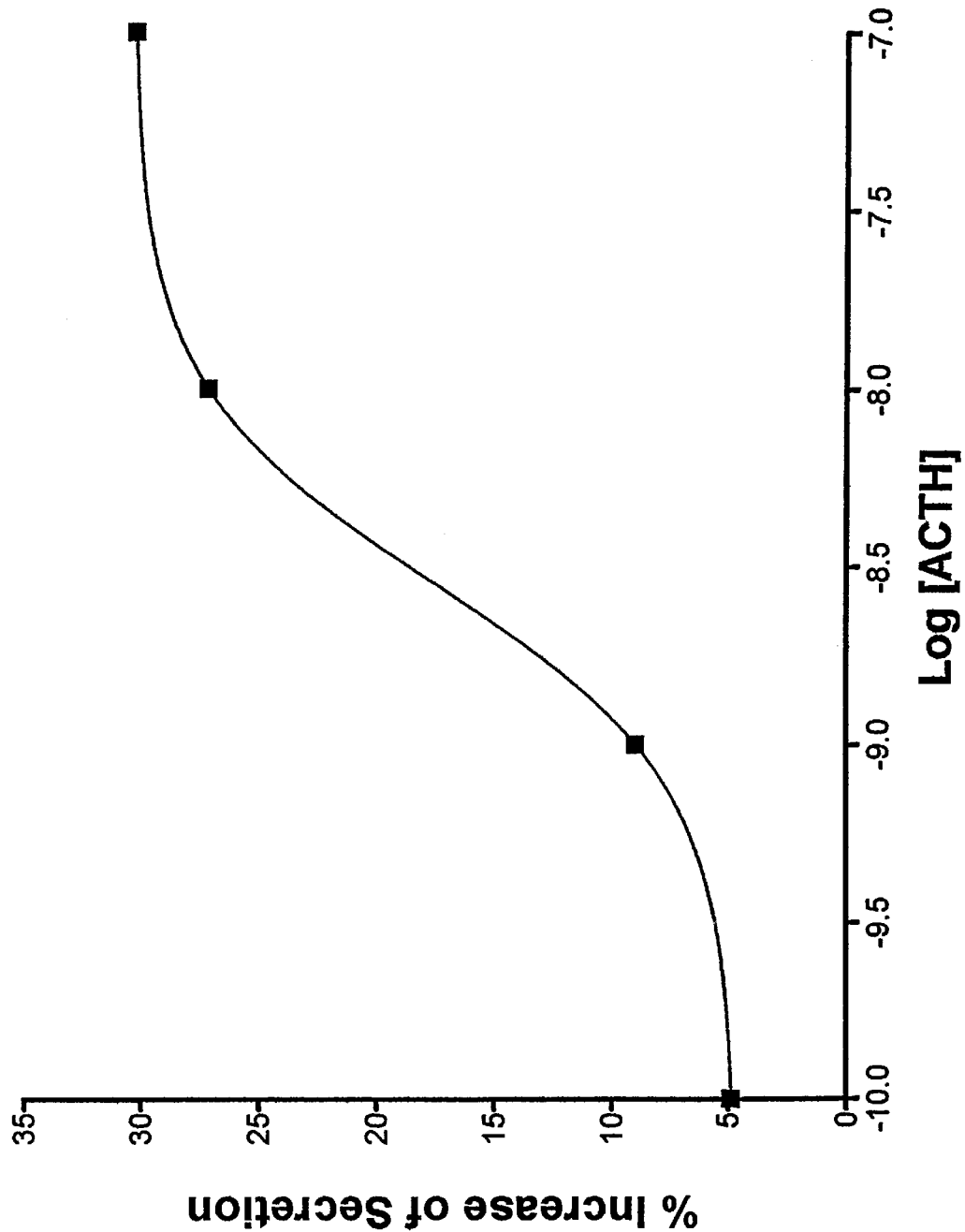
FIG. 21A shows MC5-R deficiency results in lacrimal gland dysfunction. MC5-RKO mice lack of melanocortin-stimulated protein secretion in lacrimal gland
Figure 21B:
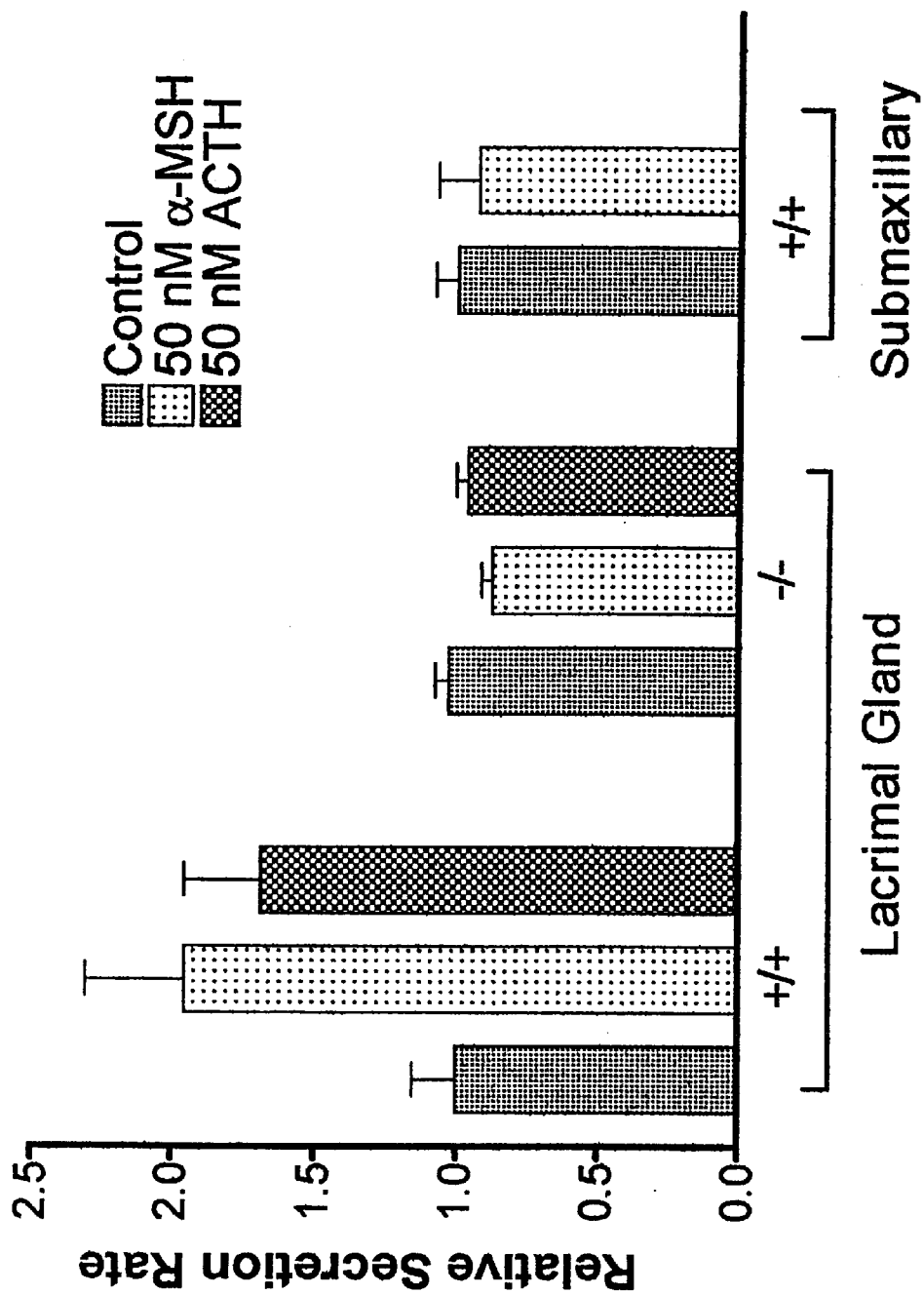
FIG. 21B shows a dose-response curve of ACTH stimulated protein secretion in lacrimal gland of C57/B1/6 mice.

These results are shown in FIGS. 21A and 21B. After lacrimal gland acini were pulsed with $^3$H-leucine, and then allowed further incubation to incorporate the radioactivity into newly synthesized proteins, the rate of protein secretion was determined by monitoring the rate of radioactivity discharge from the cells. Incubation of these tissue cultures with physiological levels of α-MSH and ACTH increased protein secretion about 80% in cultures prepared from glands of wild-type mice, but this increase was not observed in lacrimal gland cultures prepared from MC5-RKO mice (FIG. 21A). The rate of melanocortin stimulated protein discharge in gland cultures prepared from wild-type mice increased in a dose dependent fashion, with an $EC_{50}$ of 4 nM for ACTH (FIG. 21B).

It has been previously demonstrated that both ACTH and a-MSH increase total protein discharge 3–4 fold from lacrimal glands in culture (Jahn, 1982, ibid.; Leiba et al., 1990, *Eur. J. Pharmacol.* 181:71–82), and high affinity melanocortin binding sites have been demonstrated in lacrimal glands (Leiba et al., 1990, ibid.; Tatro and Reichlin, 1987, ibid). Furthermore, α-MSH stimulated peroxidase secretion in the lacrimal gland about as well as epinephrine and carbamylcholine, and was not blocked by atropine, propranolol, or phentolamine, suggesting that α-MSH is an independent secretagogue (Leiba et al., 1990, ibid.). The results disclosed herein establish that the receptor mediating these effects is the MC5-R, and the ACTH can stimulate total protein secretion from the lacrimal gland with an $EC_{50}$ of 4 nM (shown in FIG. 21B).

6. MC5-R receptor is required for porphyrin production in the Harderian gland

A. Measurement of Harderian Porphyrins

Another gland assayed in wild-type and MC5-RKO mutant mice was the Harderian gland. The Harderian gland is a bilobular retro-orbital structure that secrets primarily two products, lipids and prophyrins, into the eyes. These products are spread onto the body surface by grooming. Most vertebrates, with the exception of man, have Harderian glands, although their functional role is not well understood. In rodents, the lipid components are distributed along the coat of the animal by grooming behaviors, and play an important thermoregulatory role, suggesting that MC5-R receptors are expressed in these glands in view of the results disclosed in Sections 2 and 3 above. The porphyrins absorb UV light, and coat the cornea, where they could play some role in phototransduction. The porphyrins are co-secreted in abundance with lipids and thus an excellent marker of Harderian function.

Porphyrins in the Harderian gland were extracted as described (Margolis, 1971, *Arch. Biochem. Biophys.* 145:2377–2382). Briefly, the glands were removed from individual mice and homogenized by a motorized micropestle in 0.5 mL of an acetic acid/diethylether mixture (1:4). The homogenate was then centrifuged at 3000×g for 5 min and the resulting supernatant fluid removed and transferred to another assay tube. The centrifugation pellet was extracted twice more under identical conditions, with the resulting supernatant pooled for further analysis. Pooled extractants were concentrated in a speed-vac (Sorval) to dryness. The samples were then dissolved in 50 μL chloroform and 0.95 mL of a 0.25N HCl solution added to each assay tube. Porphyrin production from these samples were characterized by scanning spectrophotometry and spectrofluorimetry using an excitation wavelength of 402 nm.

Figure 22A:
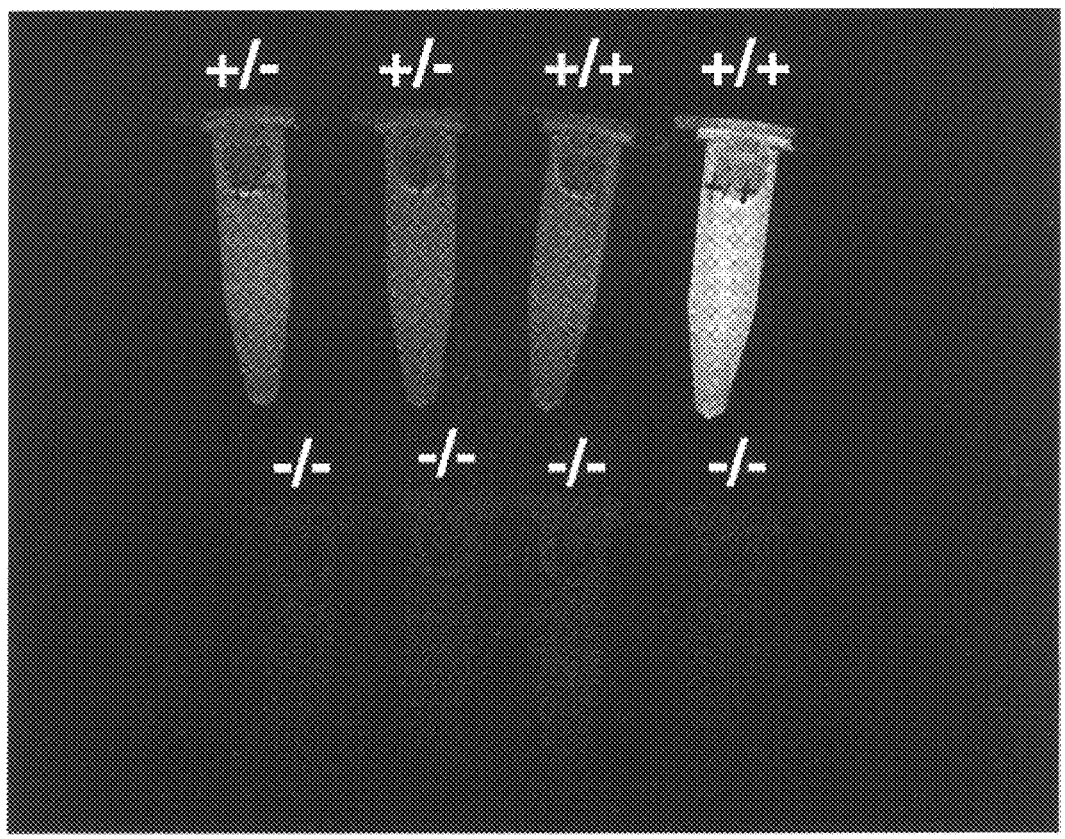
FIGS. 22A and 22B show MC5-R deficiency results in markedly reduced porphyrin content in the Harderian gland.
Figure 22B:
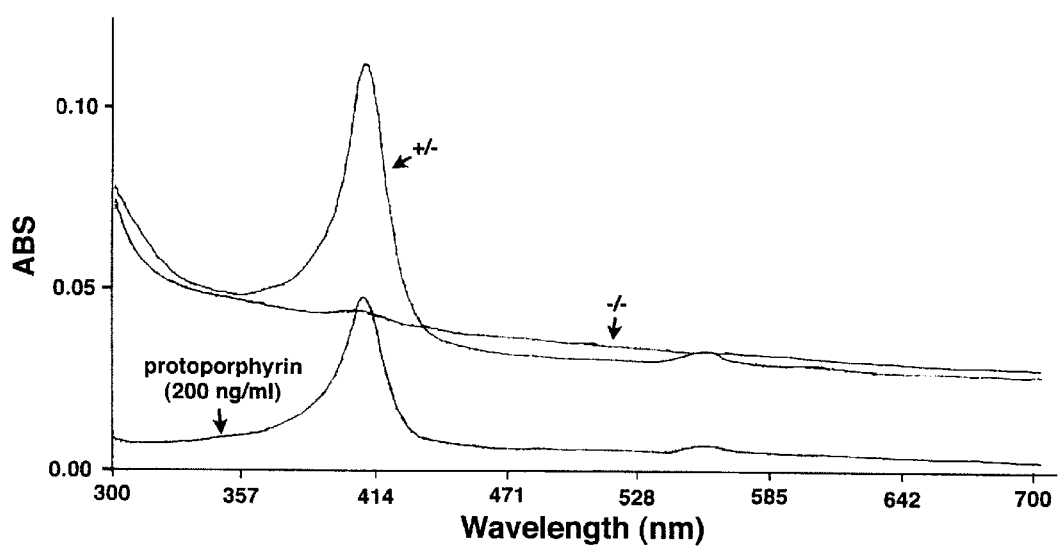

The results of these assays are shown in FIGS. 22A and 22B. Under UV light illumination, bright fluorescence was seen in organic extractants from Harderian glands of wild-type and heterozygous males; in contrast, no fluorescence was visible in those from mutant males (FIG. 22A). The extracted substances displayed two-peak absorbance at 402 and 560 nm, which confirmed the presence of porphyrins in wild-type Harderian glands. There was almost no visible absorbance at the two peaks in extracts using Harderian glands from MC5-RKO mutant mice, suggesting a nearly complete porphyrin deficiency in these animals (FIG. 22B). In addition, porphyrins from Harderian glands of wild-type and MC5-RKO mice were analyzed by scanning spectrofluorimetry, wherein one quarter of the total extract from individual mice was scanned in 0.2 mL of a 0.25 N HCl solution, using an excitation wavelength of 402 nm. For porphyrins isolated from Harderian glands of wild-type mice, a peak emission wavelength was found at 602 nm, characteristic for porphyrins. However, when excited with light at 402 nm, very little fluorescence at 602 nm was emitted from the mutant samples, compared with similar fluorescence emission obtained from porphyrins produced by Harderian glands from either wild-type or heterozygotic mice.

These results indicate that knockout mutant MC5-RKO mice are deficient in lacrimal, preputial and Harderian gland secretion, and that receptor occupancy by MC5-R receptors in these tissues in vivo regulates exocrine gland function in mammals independently of ACTH glucocorticosteroid stimulatory pathways or mechanisms. Ablation of MC5-R gene expression by homologous recombination resulted in the loss of detectable $^{125}$I-NDP-α-MSH binding to Harderian gland, lacrimal gland and preputial gland, as well as spinal cord and skeletal muscle. The binding sites demonstrated here were also shown to be effectively coupled to adenylate cyclase (FIGS. 20A and 20B) in Harderian, lacrimal, and preputial glands: in some cases, as much as a twenty-fold increase in intracellular cAMP could be seen following stimulation with 50 nM α-MSH. Thus, other biological activities of melanocortin peptides acting at these tissues are likely to be mediated by MC5-R.

EXAMPLE 6

Use of Exocrine Gland Tissue from Wild-type and MC5-R "Knockout" Mice in Assays for Detecting and Characterizing MC5-R Receptor Agonists and Antagonists The results obtained above provide reagents and methods for detecting and characterizing MC5-R receptor agonists and antagonists for use in modulating exocrine gland function.

In one example of the assays provided by this invention, primary cell cultures of exocrine gland tissue obtained from wild-type and MC5-RKO mutant mice as described in Example 5 above are prepared and the MC5-R receptor binding activity of test compounds for agonist and antagonist activity are assayed by cAMP assay and competition binding assays as described in Example 3. $EC_{50}$ values derived in these assays are used in comparison with known MC5-R agonist and antagonists to characterize the agonist/antagonist behavior of a particular test compound.

Specificity of MC5-R receptor agonists or antagonists as detected and characterized herein is also determined using a panel of recombinant cells or cells naturally expressing a melanocortin receptor gene or combinations thereof, provided that the panel comprises cells expressing each of the melanocortin receptor genes. cAMP assays, radiolabeled ligand binding assays, competitive assays and reporter-gene assays as described in Example 3 are used to determine the degree of specific binding to melanocortin receptors for such agonist and antagonist compounds.

These methods provide important means and assays for developing MC5-R specific agonists and antagonists to regulate exocrine gland function. Exocrine gland function is known to be coordinately controlled by the parasympathetic and sympathetic nervous system, with the former exerting a stimulatory effect in most cases. Hormonal regulation of exocrine gland function is also well characterized, such as the stimulation of sebaceous gland function by androgens involved in acne (Ebling et al., 1975, ibid.; Thody et al., 1976, ibid.). The disclosure herein that synthesis of lipids, proteins, and porphyrins in a variety of exocrine glands is regulated by the MC5-R suggests the existence of a coordinated system for hormonal control of exocrine gland function by melanocortin peptides.

Previous data on sebaceous gland function showed that testosterone and a-MSH are synergistic in their control of sebum production (Ebling et al., 1975, ibid.; Thody et al., 1976, ibid.). Hypophysectomy in mice (Ebling et al., 1969, *J. Endocrinol.* 45:257–263), and hypopituitarism in man (Goolamali et al., 1974, *J. Invest. Dermatol.* 63:253–255 ) decreases sebum production. The MC5-R is approximately five fold more sensitive to α-MSH than ACTH, and furthermore, ablation of the neurointermediate lobe, the source of circulating α-MSH, decreases sebum production as much as a total hypophysectomy, without decreasing testosterone levels (Thody and Shuster, 1973, ibid.). These data suggest that pituitary A-MSH regulates sebaceous gland function (Thody and Shuster, 1973, ibid.).

On the other hand, MC5-R remains very sensitive to ACTH, with $EC_{50}$ values reported in the low nM range (Fathi et al., 1995, *Neurochem. Res.* 20:107–113; Gantz et al., 1994, *Biochem. Biophys. Res. Commun.* 200:1214–1220; Griffon et al., 1994, *Biochem. Biophys. Res. Commun.* 200:1007–1014; Labbe et al., 1994, ibid.), comparable to the 1 nM $EC_{50}$ reported for activation of adenylate cyclase by the adrenocortical ACTH receptor, MC2-R (Buckley and Ramachandran, 1981, ibid.). While the affinity of the MC5-R for ACTH is somewhat lower than the MC2-R, activation of steroidogenic gene expression by the ACTH-R can be detected at ACTH levels as low as $10^{-11}$M, several logs below half-maximal receptor occupancy (Simpson, 1988). Furthermore, since circulating α-MSH is generally not detectable in man, a pituitary-derived melanocortin peptide involved in the regulation of sebaceous glands would, by necessity, have to be ACTH. Consequently, the existence of a hypothalamic-pituitary-exocrine axis would suggest the possibility of exocrine gland regulation by the stress axis.

Stress-mediated regulation of exocrine gland function via elevated levels of ACTH acting by binding to the MC5-R is also interesting with regard to pheromonally-mediated mammalian behaviors. This could provide a physiological pathway for the effects of stress on conspecific mammalian behavior via the regulation of olfactory cues, i.e., a mechanism for animals to "smell" stress. Preputial, Harderian, and sebaceous glands are all known to produce pheromones, and all express high levels of functional MC5-R (FIGS. 20A and 20B). α-MSH has been demonstrated to stimulate the release of a preputial odorant into the urine which stimulates aggressive attacks (Nowell et al., 1980, ibid). The preputial gland is also known to produce pheromones that function as sexual attractants (Bronson and Caroom, 1971, ibid.; Chipman and Alberecht, 1974, ibid.; Orsulak and Gawienowski, 1972, ibid.), as does the Harderian gland (Thiessen and Harriman, 1986, *J. Comp. Physiol.* 100:85–87).

The development of MC5-R receptor agonists and antagonists using the methods of the instant invention thus provides means and assays for developing compounds useful for the alleviation of a variety of exocrine gland-related diseases, dysfunctions and abnormal conditions, such methods being unavailable prior to the instant disclosures.

It should be understood that the foregoing disclosure emphasizes certain specific embodiments of the invention and that all modifications or alternatives equivalent thereto are within the spirit and scope of the invention as set forth in the appended claims.

SEQUENCE LISTING (1) GENERAL INFORMATION:

(iii) NUMBER OF SEQUENCES: 22

(2) INFORMATION FOR SEQ ID NO: 1:

(i) SEQUENCE CHARACTERISTICS:
      (A) LENGTH: 35 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: misc_feature
      (B) LOCATION: 1..35
      (D) OTHER INFORMATION: /function = "Degenerate oligonucleotide primer (sense)"
        /note= "The residue at positions 23 and 24 are
        inosine"

(xi) SEQUENCE DESCRIPTION: SEQ ID NO: 1:

GAGTCGACCT GTGYGYSATY RCNNTKGACM GSTAC                                        35

(2) INFORMATION FOR SEQ ID NO: 2:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..32
        (D) OTHER INFORMATION: /function = "Degenerate
            oligonucleotide primer (antisense)"
            /note= "The residue at position 18 is inosine"

(xi) SEQUENCE DESCRIPTION: SEQ ID NO: 2:

CAGAATTCAG WAGGGCANCC AGCAGASRYG AA                                           32

(2) INFORMATION FOR SEQ ID NO: 3:

(i) SEQUENCE CHARACTERISTICS:
        (A) LENGTH: 1260 base pairs
        (B) TYPE: nucleic acid
        (C) STRANDEDNESS: single
        (D) TOPOLOGY: linear (ii) MOLECULE TYPE: cDNA to mRNA (ix) FEATURE:
        (A) NAME/KEY: 5'UTR
        (B) LOCATION: 1..14

(ix) FEATURE:
        (A) NAME/KEY: CDS
        (B) LOCATION: 15..959

(ix) FEATURE:
        (A) NAME/KEY: 3'UTR
        (B) LOCATION: 960..1260

(xi) SEQUENCE DESCRIPTION: SEQ ID NO: 3:

TTCCTGACAA GACT ATG TCC ACT CAG GAG CCC CAG AAG AGT CTT CTG GGT               50
              Met Ser Thr Gln Glu Pro Gln Lys Ser Leu Leu Gly
               1               5                  10

TCT CTC AAC TCC AAT GCC ACC TCT CAC CTT GGA CTG GCC ACC AAC CAG               98
Ser Leu Asn Ser Asn Ala Thr Ser His Leu Gly Leu Ala Thr Asn Gln
         15                  20                  25

TCA GAG CCT TGG TGC CTG TAT GTG TCC ATC CCA GAT GGC CTC TTC CTC              146
Ser Glu Pro Trp Cys Leu Tyr Val Ser Ile Pro Asp Gly Leu Phe Leu
     30                  35                  40

AGC CTA GGG CTG GTG AGT CTG GTG GAG AAT GTG CTG GTT GTG ATA GCC              194
Ser Leu Gly Leu Val Ser Leu Val Glu Asn Val Leu Val Val Ile Ala
 45                  50                  55                  60

ATC ACC AAA AAC CGC AAC CTG CAC TCG CCC ATG TAT TAC TTC ATC TGC              242
Ile Thr Lys Asn Arg Asn Leu His Ser Pro Met Tyr Tyr Phe Ile Cys
                 65                  70                  75

TGC CTG GCC CTG TCT GAC CTG ATG GTA AGT GTC AGC ATC GTG CTG GAG              290
Cys Leu Ala Leu Ser Asp Leu Met Val Ser Val Ser Ile Val Leu Glu
         80                  85                  90

```
ACT ACT ATC ATC CTG CTG CTG GAG GTG GGC ATC CTG GTG GCC AGA GTG       338
Thr Thr Ile Ile Leu Leu Leu Glu Val Gly Ile Leu Val Ala Arg Val
        95              100             105

GCT TTG GTG CAG CAG CTG GAC AAC CTC ATT GAC GTG CTC ATC TGT GGC       386
Ala Leu Val Gln Gln Leu Asp Asn Leu Ile Asp Val Leu Ile Cys Gly
    110             115             120

TCC ATG GTG TCC AGT CTC TGC TTC CTG GGC ATC ATT GCT ATA GAC CGC       434
Ser Met Val Ser Ser Leu Cys Phe Leu Gly Ile Ile Ala Ile Asp Arg
125             130             135             140

TAC ATC TCC ATC TTC TAT GCG CTG CGT TAT CAC AGC ATC GTG ACG CTG       482
Tyr Ile Ser Ile Phe Tyr Ala Leu Arg Tyr His Ser Ile Val Thr Leu
            145             150             155

CCC AGA GCA CGA CGG GCT GTC GTG GGC ATC TGG ATG GTC AGC ATC GTC       530
Pro Arg Ala Arg Arg Ala Val Val Gly Ile Trp Met Val Ser Ile Val
        160             165             170

TCC AGC ACC CTC TTT ATC ACC TAC TAC AAG CAC ACA GCC GTT CTG CTC       578
Ser Ser Thr Leu Phe Ile Thr Tyr Tyr Lys His Thr Ala Val Leu Leu
    175             180             185

TGC CTC GTC ACT TTC TTT CTA GCC ATG CTG GCA CTC ATG GCG ATT CTG       626
Cys Leu Val Thr Phe Phe Leu Ala Met Leu Ala Leu Met Ala Ile Leu
190             195             200

TAT GCC CAC ATG TTC ACG AGA GCG TGC CAG CAC GTC CAG GGC ATT GCC       674
Tyr Ala His Met Phe Thr Arg Ala Cys Gln His Val Gln Gly Ile Ala
205             210             215             220

CAG CTC CAC AAA AGG CGG CGG TCC ATC CGC CAA GGC TTC TGC CTC AAG       722
Gln Leu His Lys Arg Arg Arg Ser Ile Arg Gln Gly Phe Cys Leu Lys
            225             230             235

GGT GCT GCC ACC CTT ACT ATC CTT CTG GGG ATT TTC TTC CTG TGC TGG       770
Gly Ala Ala Thr Leu Thr Ile Leu Leu Gly Ile Phe Phe Leu Cys Trp
        240             245             250

GGC CCC TTC TTC CTG CAT CTC TTG CTC ATC GTC CTC TGC CCT CAG CAC       818
Gly Pro Phe Phe Leu His Leu Leu Leu Ile Val Leu Cys Pro Gln His
    255             260             265

CCC ACC TGC AGC TGC ATC TTC AAG AAC TTC AAC CTC TTC CTC CTC CTC       866
Pro Thr Cys Ser Cys Ile Phe Lys Asn Phe Asn Leu Phe Leu Leu Leu
270             275             280

ATC GTC CTC AGC TCC ACT GTT GAC CCC CTC ATC TAT GCT TTC CGC AGC       914
Ile Val Leu Ser Ser Thr Val Asp Pro Leu Ile Tyr Ala Phe Arg Ser
285             290             295             300

CAG GAG CTC CGC ATG ACA CTC AAG GAG GTG CTG CTG TGC TCC TGG           959
Gln Glu Leu Arg Met Thr Leu Lys Glu Val Leu Leu Cys Ser Trp
            305             310             315

TGATCAGAGG GCGCTGGGCA GAGGGTGACA GTGATATCCA GTGGCCTGCA TCTGTGAGAC    1019

CACAGGTACT CATCCCTTCC TGATCTCCAT TTGTCTAAGG GTCGACAGGA TGAGCTTTAA    1079

AATAGAAACC CAGAGTGCCT GGGGCCAGGA GAAAGGGTAA CTGTGACTGC AGGGCTCACC    1139

CAGGGCAGCT ACGGGAAGTG GAGGAGACAG GGATGGGAAC TCTAGCCCTG AGCAAGGGTC    1199

AGACCACAGG CTCCTGAAGA GCTTCACCTC TCCCCACCTA CAGGCAACTC CTGCTCAAGC    1259

C                                                                   1260

(2) INFORMATION FOR SEQ ID NO: 4:

(i) SEQUENCE CHARACTERISTICS:
        (A) LENGTH: 315 amino acids
        (B) TYPE: amino acid
        (D) TOPOLOGY: linear (ii) MOLECULE TYPE: protein (xi) SEQUENCE DESCRIPTION: SEQ ID NO: 4:
```

```
Met Ser Thr Gln Glu Pro Gln Lys Ser Leu Leu Gly Ser Leu Asn Ser
 1               5                  10                  15

Asn Ala Thr Ser His Leu Gly Leu Ala Thr Asn Gln Ser Glu Pro Trp
            20                  25                  30

Cys Leu Tyr Val Ser Ile Pro Asp Gly Leu Phe Leu Ser Leu Gly Leu
            35                  40                  45

Val Ser Leu Val Glu Asn Val Leu Val Ile Ala Ile Thr Lys Asn
        50                  55                  60

Arg Asn Leu His Ser Pro Met Tyr Tyr Phe Ile Cys Cys Leu Ala Leu
 65                  70                  75                  80

Ser Asp Leu Met Val Ser Val Ser Ile Val Leu Glu Thr Thr Ile Ile
                85                  90                  95

Leu Leu Leu Glu Val Gly Ile Leu Val Ala Arg Val Ala Leu Val Gln
                100                 105                 110

Gln Leu Asp Asn Leu Ile Asp Val Leu Ile Cys Gly Ser Met Val Ser
            115                 120                 125

Ser Leu Cys Phe Leu Gly Ile Ile Ala Ile Asp Arg Tyr Ile Ser Ile
        130                 135                 140

Phe Tyr Ala Leu Arg Tyr His Ser Ile Val Thr Leu Pro Arg Ala Arg
145                 150                 155                 160

Arg Ala Val Val Gly Ile Trp Met Val Ser Ile Val Ser Ser Thr Leu
                165                 170                 175

Phe Ile Thr Tyr Tyr Lys His Thr Ala Val Leu Leu Cys Leu Val Thr
            180                 185                 190

Phe Phe Leu Ala Met Leu Ala Leu Met Ala Ile Leu Tyr Ala His Met
        195                 200                 205

Phe Thr Arg Ala Cys Gln His Val Gln Gly Ile Ala Gln Leu His Lys
    210                 215                 220

Arg Arg Arg Ser Ile Arg Gln Gly Phe Cys Leu Lys Gly Ala Ala Thr
225                 230                 235                 240

Leu Thr Ile Leu Leu Gly Ile Phe Phe Leu Cys Trp Gly Pro Phe Phe
                245                 250                 255

Leu His Leu Leu Leu Ile Val Leu Cys Pro Gln His Pro Thr Cys Ser
            260                 265                 270

Cys Ile Phe Lys Asn Phe Asn Leu Phe Leu Leu Leu Ile Val Leu Ser
        275                 280                 285

Ser Thr Val Asp Pro Leu Ile Tyr Ala Phe Arg Ser Gln Glu Leu Arg
    290                 295                 300

Met Thr Leu Lys Glu Val Leu Leu Cys Ser Trp
305                 310                 315
```

(2) INFORMATION FOR SEQ ID NO: 5:

(i) SEQUENCE CHARACTERISTICS:
        (A) LENGTH: 1633 base pairs
        (B) TYPE: nucleic acid
        (C) STRANDEDNESS: single
        (D) TOPOLOGY: linear (ii) MOLECULE TYPE: cDNA to mRNA (ix) FEATURE:
        (A) NAME/KEY: 5'UTR
        (B) LOCATION: 1..461

(ix) FEATURE:
        (A) NAME/KEY: CDS
        (B) LOCATION: 462..1415

(ix) FEATURE:
    (A) NAME/KEY: 3'UTR
    (B) LOCATION: 1416..1633

(xi) SEQUENCE DESCRIPTION: SEQ ID NO: 5:

```
CCCGCATGTG GCCGCCCTCA ATGGAGGGCT CTGAGAACGA CTTTTAAAAC GCAGAGAAAA      60

AGCTCCATTC TTCCCAGACC TCAGCGCAGC CCTGGCCCAG GAAGGGAGGA GACAGAGGCC     120

AGGACGGTCC AGAGGTGTCG AAATGTCCTG GGAACCTGAG CAGCAGCCAC CAGGGAAGAG     180

GCAGGGAGGG AGCTGAGGAC CAGGCTTGGT TGTGAGAATC CCTGAGCCCA GGCGGTTGAT     240

GCCAGGAGGT GTCTGGACTG GCTGGGCCAT GCCTGGGCTG ACCTGTCCAG CCAGGGAGAG     300

GGTGTGAGGG CAGATCTGGG GGTGCCCAGA TGGAAGGAGG CAGGCATGGG GACACCCAAG     360

GCCCCCTGGC AGCACCATGA ACTAAGCAGG ACACCTGGAG GGGAAGAACT GTGGGGACCT     420

GGAGGCCTCC AACGACTCCT TCCTGCTTCC TGGACAGGAC T ATG GCT GTG CAG         473
                                             Met Ala Val Gln
                                               1
```

| | | | | | | | | | | | | | | | |
|---|---|---|---|---|---|---|---|---|---|---|---|---|---|---|---|
| GGA | TCC | CAG | AGA | AGA | CTT | CTG | GGC | TCC | CTC | AAC | TCC | ACC | CCC | ACA | GCC | 521
| Gly | Ser | Gln | Arg | Arg | Leu | Leu | Gly | Ser | Leu | Asn | Ser | Thr | Pro | Thr | Ala |
| 5 | | | | 10 | | | | | 15 | | | | | 20 | |

```
ATC CCC CAG CTG GGG CTG GCT GCC AAC CAG ACA GGA GCC CGG TGC CTG     569
Ile Pro Gln Leu Gly Leu Ala Ala Asn Gln Thr Gly Ala Arg Cys Leu
            25                  30                  35

GAG GTG TCC ATC TCT GAC GGG CTC TTC CTC AGC CTG GGG CTG GTG AGC     617
Glu Val Ser Ile Ser Asp Gly Leu Phe Leu Ser Leu Gly Leu Val Ser
                40                  45                  50

TTG GTG GAG AAC GCG CTG GTG GTG GCC ACC ATC GCC AAG AAC CGG AAC     665
Leu Val Glu Asn Ala Leu Val Val Ala Thr Ile Ala Lys Asn Arg Asn
        55                  60                  65

CTG CAC TCA CCC ATG TAC TGC TTC ATC TGC TGC CTG GCC TTG TCG GAC     713
Leu His Ser Pro Met Tyr Cys Phe Ile Cys Cys Leu Ala Leu Ser Asp
    70                  75                  80

CTG CTG GTG AGC GGG ACG AAC GTG CTG GAG ACG GCC GTC ATC CTC CTG     761
Leu Leu Val Ser Gly Thr Asn Val Leu Glu Thr Ala Val Ile Leu Leu
85                  90                  95                 100

CTG GAG GCC GGT GCA CTG GTG GCC CGG GCT GCG GTG CTG CAG CAG CTG     809
Leu Glu Ala Gly Ala Leu Val Ala Arg Ala Ala Val Leu Gln Gln Leu
                105                 110                 115

GAC AAT GTC ATT GAC GTG ATC ACC TGC AGC TCC ATG CTG TCC AGC CTC     857
Asp Asn Val Ile Asp Val Ile Thr Cys Ser Ser Met Leu Ser Ser Leu
            120                 125                 130

TGC TTC CTG GGC GCC ATC GCC GTG GAC CGC TAC ATC TCC ATC TTC TAC     905
Cys Phe Leu Gly Ala Ile Ala Val Asp Arg Tyr Ile Ser Ile Phe Tyr
        135                 140                 145

GCA CTG CGC TAC CAC AGC ATC GTG ACC CTG CCG CGG GCG CCG CGA GCC     953
Ala Leu Arg Tyr His Ser Ile Val Thr Leu Pro Arg Ala Pro Arg Ala
    150                 155                 160

GTT GCG GCC ATC TGG GTG GCC AGT GTC GTC TTC AGC ACG CTC TTC ATC    1001
Val Ala Ala Ile Trp Val Ala Ser Val Val Phe Ser Thr Leu Phe Ile
165                 170                 175                 180

GGC TAC TAC GAC CAC GTG GCC GTC CTG CTG TGC CTC GTG GTC TTC TTC    1049
Gly Tyr Tyr Asp His Val Ala Val Leu Leu Cys Leu Val Val Phe Phe
                185                 190                 195

CTG GCT ATG CTG GTG CTC ATG GCC GTG CTG TAC GTC CAC ATG CTG GCC    1097
Leu Ala Met Leu Val Leu Met Ala Val Leu Asp Val His Met Leu Ala
            200                 205                 210

CGG GCC TGC CAG CAC GCC CAG GGC ATC GCC CGG CTC CAC AAG AGG CAG    1145
Arg Ala Cys Gln His Ala Gln Gly Ile Ala Arg Leu His Lys Arg Gln
```

-continued

```
           215                 220                 225
CGC CCG GTC CAC CAG GGC TTT GGC CTT AAA GGC GCT GTC ACC CTC ACC    1193
Arg Pro Val His Gln Gly Phe Gly Leu Lys Gly Ala Val Thr Leu Thr
    230                 235                 240

ATC CTG CTG GGC ATT TTC TTC CTC TGC TGG GGC CCC TTC TTC CTG CAT    1241
Ile Leu Leu Gly Ile Phe Phe Leu Cys Trp Gly Pro Phe Phe Leu His
245                 250                 255                 260

CTC ACA CTC ATC GTC CTC TGC CCC GAG CAC CCC ACG TGC GGC TGC ATC    1289
Leu Thr Leu Ile Val Leu Cys Pro Glu His Pro Thr Cys Gly Cys Ile
                265                 270                 275

TTC AAG AAC TTC AAC CTC TTT CTC GCC CTC ATC ATC TGC AAT GCC ATC    1337
Phe Lys Asn Phe Asn Leu Phe Leu Ala Leu Ile Ile Cys Asn Ala Ile
            280                 285                 290

ATC GAC CCC CTC ATC TAC GCC TTC CAC AGC CAG GAG CTC CGC AGG ACG    1385
Ile Asp Pro Leu Ile Tyr Ala Phe His Ser Gln Glu Leu Arg Arg Thr
        295                 300                 305

CTC AAG GAG GTG CTG ACA TGC TCC TGG TGA GCGCGGTGCA CGCGCTTTAA       1435
Leu Lys Glu Val Leu Thr Cys Ser Trp *
    310                 315

GTGTGCTGGG CAGAGGGAGG TGGTGATATT GTGGTCTGGT TCCTGTGTGA CCCTGGGCAG    1495

TTCCTTACCT CCCTGGTCCC CGTTTGTCAA AGAGGATGGA CTAAATGATC TCTGAAAGTG    1555

TTGAAGCGCG GACCCTTCTG GGCAGGGAGG GGTCCTGCAA AACTCCAGGC AGGACTTCTC    1615

ACCAGCAGTC GTGGGAAC                                                  1633
```

(2) INFORMATION FOR SEQ ID NO: 6:

(i) SEQUENCE CHARACTERISTICS:
        (A) LENGTH: 317 amino acids
        (B) TYPE: amino acid
        (D) TOPOLOGY: linear (ii) MOLECULE TYPE: protein (xi) SEQUENCE DESCRIPTION: SEQ ID NO: 6:

```
Met Ala Val Gln Gly Ser Gln Arg Arg Leu Leu Gly Ser Leu Asn Ser
1               5                   10                  15

Thr Pro Thr Ala Ile Pro Gln Leu Gly Leu Ala Ala Asn Gln Thr Gly
                20                  25                  30

Ala Arg Cys Leu Glu Val Ser Ile Ser Asp Gly Leu Phe Leu Ser Leu
            35                  40                  45

Gly Leu Val Ser Leu Val Glu Asn Ala Leu Val Val Ala Thr Ile Ala
        50                  55                  60

Lys Asn Arg Asn Leu His Ser Pro Met Tyr Cys Phe Ile Cys Cys Leu
65                  70                  75                  80

Ala Leu Ser Asp Leu Leu Val Ser Gly Thr Asn Val Leu Glu Thr Ala
                85                  90                  95

Val Ile Leu Leu Leu Glu Ala Gly Ala Leu Val Ala Arg Ala Ala Val
                100                 105                 110

Leu Gln Gln Leu Asp Asn Val Ile Asp Val Ile Thr Cys Ser Ser Met
            115                 120                 125

Leu Ser Ser Leu Cys Phe Leu Gly Ala Ile Ala Val Asp Arg Tyr Ile
        130                 135                 140

Ser Ile Phe Tyr Ala Leu Arg Tyr His Ser Ile Val Thr Leu Pro Arg
145                 150                 155                 160

Ala Pro Arg Ala Val Ala Ala Ile Trp Val Ala Ser Val Val Phe Ser
                165                 170                 175
```

```
Thr Leu Phe Ile Gly Tyr Tyr Asp His Val Ala Val Leu Leu Cys Leu
            180                 185                 190

Val Val Phe Phe Leu Ala Met Leu Val Leu Met Ala Val Leu Asp Val
            195                 200                 205

His Met Leu Ala Arg Ala Cys Gln His Ala Gln Gly Ile Ala Arg Leu
    210                 215                 220

His Lys Arg Gln Arg Pro Val His Gln Gly Phe Gly Leu Lys Gly Ala
225                 230                 235                 240

Val Thr Leu Thr Ile Leu Leu Gly Ile Phe Phe Leu Cys Trp Gly Pro
                245                 250                 255

Phe Phe Leu His Leu Thr Leu Ile Val Leu Cys Pro Glu His Pro Thr
            260                 265                 270

Cys Gly Cys Ile Phe Lys Asn Phe Asn Leu Phe Leu Ala Leu Ile Ile
            275                 280                 285

Cys Asn Ala Ile Ile Asp Pro Leu Ile Tyr Ala Phe His Ser Gln Glu
    290                 295                 300

Leu Arg Arg Thr Leu Lys Glu Val Leu Thr Cys Ser Trp
305                 310                 315

(2) INFORMATION FOR SEQ ID NO: 7:

(i) SEQUENCE CHARACTERISTICS:
        (A) LENGTH: 2012 base pairs
        (B) TYPE: nucleic acid
        (C) STRANDEDNESS: single
        (D) TOPOLOGY: linear (ii) MOLECULE TYPE: cDNA to mRNA (ix) FEATURE:
        (A) NAME/KEY: 5'UTR
        (B) LOCATION: 1..693

(ix) FEATURE:
        (A) NAME/KEY: CDS
        (B) LOCATION: 694..1587

(ix) FEATURE:
        (A) NAME/KEY: 3'UTR
        (B) LOCATION: 1588..2012

(xi) SEQUENCE DESCRIPTION: SEQ ID NO: 7:

ACAACACTTT ATATATATTT TTATAAATGT AAGGGGTACA AAGGTGCCAT TTTGTTACAT      60

GGATATACCG TGTAGTGGTG AAGCCTGGGC TTTTAGTGTA TCTGTCATCA GAATAACATA     120

CGTGTTACCC ATAGGAATTT CTCATCACCC GCCCCCTCCA CCCTTCGAGT CTCCAATGTC     180

CATTCCACAC TCTATATCCA CGTGTATGCA TATAGCTCCA CATATAAGTG AGAACATGTA     240

GTATTTGACT TCCTCTTTCT GAGTTATTTC ACTTTGATAA TGGCCTCCAC TTCCATCCAT     300

GTTGCTGCAA AAGACATGAC CTTATTCTTT TTGATAGCTG GGGAGTACTC CATTGTGTAT     360

ATGTACCACA TTTCTTTATC CATTCACCCA TTGAGAACAC TTAGTTGATT CCATATCTTT     420

GCTATTGTCA CTAGTGCTGC AATAAACATA CATGTGCAGG CTCCTTCTAA TATACTGATT     480

TATATTTTAT GGAGAGAGAT AGAGTTCTTA GCGAGTGTGC TGTTTATTTC TAGTGTACTT     540

GCAACTAATA TTCTGTATAC TCCCTTTAGG TGATTGGAGA TTTAACTTAG ATCTCCAGCA     600

AGTGCTACAA GAAGAAAAGA TCCTGAAGAA TCAATCAAGT TTCCGTGAAG TCAAGTCCAA     660

GTAACATCCC CGCCTTAACC ACAAGCAGGA GAA ATG AAG CAC ATT ATC AAC TCG     714
                                    Met Lys His Ile Ile Asn Ser
                                      1               5

TAT GAA AAC ATC AAC AAC ACA GCA AGA AAT AAT TCC GAC TGT CCT CGT      762
```

-continued

```
            Tyr Glu Asn Ile Asn Asn Thr Ala Arg Asn Asn Ser Asp Cys Pro Arg
                    10                  15                  20
TGT GTT TTG CCG GAG GAG ATA TTT TTC ACA ATT TCC ATT GTT GGA GTT            810
Cys Val Leu Pro Glu Glu Ile Phe Phe Thr Ile Ser Ile Val Gly Val
        25                  30                  35

TTG GAG AAT CTG ATC GTC CTG CTG GCT GTG TTC AAG AAT AAG AAT CTC            858
Leu Glu Asn Leu Ile Val Leu Leu Ala Val Phe Lys Asn Lys Asn Leu
 40                  45                  50                  55

CAG GCA CCC ATG TAC TTT TTC ATC TGT AGC TTG GCC ATA TCT GAT ATG            906
Gln Ala Pro Met Tyr Phe Phe Ile Cys Ser Leu Ala Ile Ser Asp Met
                60                  65                  70

CTG GGC AGC CTA TAT AAG ATC TTG GAA AAT ATC CTG ATC ATA TTG AGA            954
Leu Gly Ser Leu Tyr Lys Ile Leu Glu Asn Ile Leu Ile Ile Leu Arg
            75                  80                  85

AAC ATG GGC ATA CTC AAG CCA CGT GGC AGT TTT GAA ACC ACA GCC CAT           1002
Asn Met Gly Ile Leu Lys Pro Arg Gly Ser Phe Glu Thr Thr Ala His
        90                  95                 100

GAC ATC ATC GAC TCC CTG TTT CTG CTC TCC CGT CTT GGC TCC ATC TTC           1050
Asp Ile Ile Asp Ser Leu Phe Leu Leu Ser Arg Leu Gly Ser Ile Phe
    105                 110                 115

GAC CTG CTC GTG ATT GCT GCG GAC CGC TAC ATC ACC ATC TTC CAC GCA           1098
Asp Leu Leu Val Ile Ala Ala Asp Arg Tyr Ile Thr Ile Phe His Ala
120                 125                 130                 135

CTG CGG TAC CAC AGC ATC GTG ACC ATG CGC CGC ACT GTG GTG GTG CTT           1146
Leu Arg Tyr His Ser Ile Val Thr Met Arg Arg Thr Val Val Val Leu
                140                 145                 150

ACG GTC ATC TGG ACG TTC TGC ACG GGG ACT GGC ATC ACC ATG GTG ATC           1194
Thr Val Ile Trp Thr Phe Cys Thr Gly Thr Gly Ile Thr Met Val Ile
            155                 160                 165

TTC TCC CAT CAT GTG CCC CAC GTG ATC ACC TTC ACG TCG CTG TTC CCG           1242
Phe Ser His His Val Pro His Val Ile Thr Phe Thr Ser Leu Phe Pro
        170                 175                 180

CTG ATG CTG GTC TTC ATC CTG TGC CTC TAT GTG CAC ATG TTC CTG CTG           1290
Leu Met Leu Val Phe Ile Leu Cys Leu Tyr Val His Met Phe Leu Leu
    185                 190                 195

GCT CGA TGG CAC ACC AGG AAG ATC TCC ACC CTC CCC AGA GCC AAC ATG           1338
Ala Arg Trp His Thr Arg Lys Ile Ser Thr Leu Pro Arg Ala Asn Met
200                 205                 210                 215

AAA GGG GCC ATG ACA CTG ACC ATC CTG CTC GGG GTC TTC ATC TTC TGC           1386
Lys Gly Ala Met Thr Leu Thr Ile Leu Leu Gly Val Phe Ile Phe Cys
                220                 225                 230

TGG GCC CCC TTT GTG CTT CAT GTC CTC TTG ATG ACA TTC TGC CCA AGT           1434
Trp Ala Pro Phe Val Leu His Val Leu Leu Met Thr Phe Cys Pro Ser
            235                 240                 245

AAC CCC TAC TGC GCC TGC TAC ATG TCT CTC TTC CAG GTG AAC GGC ATG           1482
Asn Pro Tyr Cys Ala Cys Tyr Met Ser Leu Phe Gln Val Asn Gly Met
        250                 255                 260

TTG ATC ATG TGC AAT GCC GTC ATT GAC CCC TTC ATA TAT GCC TTC CGG           1530
Leu Ile Met Cys Asn Ala Val Ile Asp Pro Phe Ile Tyr Ala Phe Arg
    265                 270                 275

AGC CCA GAG CTC AGG GAC GCA TTC AAA AAG ATG ATC TTC TGC AGC AGG           1578
Ser Pro Glu Leu Arg Asp Ala Phe Lys Lys Met Ile Phe Cys Ser Arg
280                 285                 290                 295

TAC TGG TAG AATGGCTGAT CCCTGGTTTT AGAATCCATG GGAATAACGT                   1627
Tyr Trp *

TGCCAAGTGC CAGAATAGTG TAACATTCCA ACAAATGCCA GTGCTCCTCA CTGGCCTTCC         1687

TTCCCTAATG GATGCAAGGA TGACCCACCA GCTAGTGTTT CTGAATACTA TGGCCAGGAA         1747

CAGTCTATTG TAGGGGCAAC TCTATTTGTG ACTGGACAGA TAAAACGTGT AGTAAAAGAA         1807
```

```
GGATAGAATA CAAAGTATTA GGTACAAAAG TAATTAGGTT TGCATTACTT ATGACAAATG    1867

CATTACTTTT GCACCAATCT AGTAAAACAG CAATAAAAAT TCAAGGGCTT TGGGCTAAGG    1927

CAAAGACTTG CTTTCCTGTG GACATTAACA AGCCAGTTCT GAGGCGGCCT TTCCAGGTGG    1987

AGGCCATTGC AGCCAATTTC AGAGT                                          2012
```

(2) INFORMATION FOR SEQ ID NO: 8:

(i) SEQUENCE CHARACTERISTICS:
        (A) LENGTH: 297 amino acids
        (B) TYPE: amino acid
        (D) TOPOLOGY: linear (ii) MOLECULE TYPE: protein (xi) SEQUENCE DESCRIPTION: SEQ ID NO: 8:

```
Met Lys His Ile Ile Asn Ser Tyr Glu Asn Ile Asn Asn Thr Ala Arg
 1               5                  10                  15

Asn Asn Ser Asp Cys Pro Arg Cys Val Leu Pro Glu Glu Ile Phe Phe
            20                  25                  30

Thr Ile Ser Ile Val Gly Val Leu Glu Asn Leu Ile Val Leu Leu Ala
        35                  40                  45

Val Phe Lys Asn Lys Asn Leu Gln Ala Pro Met Tyr Phe Phe Ile Cys
 50                  55                  60

Ser Leu Ala Ile Ser Asp Met Leu Gly Ser Leu Tyr Lys Ile Leu Glu
 65                  70                  75                  80

Asn Ile Leu Ile Ile Leu Arg Asn Met Gly Ile Leu Lys Pro Arg Gly
                85                  90                  95

Ser Phe Glu Thr Thr Ala His Asp Ile Ile Asp Ser Leu Phe Leu Leu
            100                 105                 110

Ser Arg Leu Gly Ser Ile Phe Asp Leu Leu Val Ile Ala Ala Asp Arg
        115                 120                 125

Tyr Ile Thr Ile Phe His Ala Leu Arg Tyr His Ser Ile Val Thr Met
130                 135                 140

Arg Arg Thr Val Val Val Leu Thr Val Ile Trp Thr Phe Cys Thr Gly
145                 150                 155                 160

Thr Gly Ile Thr Met Val Ile Phe Ser His His Val Pro His Val Ile
                165                 170                 175

Thr Phe Thr Ser Leu Phe Pro Leu Met Leu Val Phe Ile Leu Cys Leu
            180                 185                 190

Tyr Val His Met Phe Leu Leu Ala Arg Trp His Thr Arg Lys Ile Ser
        195                 200                 205

Thr Leu Pro Arg Ala Asn Met Lys Gly Ala Met Thr Leu Thr Ile Leu
    210                 215                 220

Leu Gly Val Phe Ile Phe Cys Trp Ala Pro Phe Val Leu His Val Leu
225                 230                 235                 240

Leu Met Thr Phe Cys Pro Ser Asn Pro Tyr Cys Ala Cys Tyr Met Ser
                245                 250                 255

Leu Phe Gln Val Asn Gly Met Leu Ile Met Cys Asn Ala Val Ile Asp
            260                 265                 270

Pro Phe Ile Tyr Ala Phe Arg Ser Pro Glu Leu Arg Asp Ala Phe Lys
        275                 280                 285

Lys Met Ile Phe Cys Ser Arg Tyr Trp
290                 295
```

(2) INFORMATION FOR SEQ ID NO: 9:

(i) SEQUENCE CHARACTERISTICS:
        (A) LENGTH: 1108 base pairs
        (B) TYPE: nucleic acid
        (C) STRANDEDNESS: single
        (D) TOPOLOGY: linear (ii) MOLECULE TYPE: cDNA to mRNA (ix) FEATURE:
        (A) NAME/KEY: 5'UTR
        (B) LOCATION: 1..132

(ix) FEATURE:
        (A) NAME/KEY: CDS
        (B) LOCATION: 133..1026

(ix) FEATURE:
        (A) NAME/KEY: 3'UTR
        (B) LOCATION: 1027..1106

(xi) SEQUENCE DESCRIPTION: SEQ ID NO: 9:

```
GGGGCCAGAA AGTTCCTGCT TCAGAGCAGA AGATCTTCAG CAAGAACTAC AAAGAAGAAA        60

AGATTCTGGA GAATCAATCA AGTTTCCTGT CAAGTTCCAG TAACGTTTCT GTCTTAACTG       120

CACACAGGAA AG ATG AAA CAC ATT CTC AAT CTG TAT GAA AAC CTC AAC           168
              Met Lys His Ile Leu Asn Leu Tyr Glu Asn Leu Asn
                1               5                  10

AGT ACA GCA AGA AAT AAC TCA GAC TGT CCT GCT GTG ATT TTG CCA GAA         216
Ser Thr Ala Arg Asn Asn Ser Asp Cys Pro Ala Val Ile Leu Pro Glu
            15                  20                  25

GAG ATA TTT TTC ACA GTA TCC ATT GTT GGG GTT TTG GAG AAC CTG ATG         264
Glu Ile Phe Phe Thr Val Ser Ile Val Gly Val Leu Glu Asn Leu Met
        30                  35                  40

GTC CTT CTG GCT GTG GCC AAG AAT AAG ATG CTT CAG TCG CCC ATG TAC         312
Val Leu Leu Ala Val Ala Lys Asn Lys Met Leu Gln Ser Pro Met Tyr
 45                  50                  55                  60

TTT TTC ATC TGC AGC TTG GCT ATT TCC GAT ATG CTG GGG AGC ATG TAC         360
Phe Phe Ile Cys Ser Leu Ala Ile Ser Asp Met Leu Gly Ser Met Tyr
                65                  70                  75

AAG ATT TTG GAA AAC GTT CTG ATC ATG TTC AAA AAC ATG GGT TAC CTC         408
Lys Ile Leu Glu Asn Val Leu Ile Met Phe Lys Asn Met Gly Tyr Leu
            80                  85                  90

GAG CCT CGA GGC AGT TTT GAA AGC ACA GCA GAT GAT GTG GTG GAC TCC         456
Glu Pro Arg Gly Ser Phe Glu Ser Thr Ala Asp Asp Val Val Asp Ser
        95                  100                 105

CTG TTC ATC CTC TCC CTT CTC GGC TCC ATC TGC AGC CTG TCT GTG ATT         504
Leu Phe Ile Leu Ser Leu Leu Gly Ser Ile Cys Ser Leu Ser Val Ile
 110                 115                 120

GCC GCT GAC CGC TAC ACT ACA ATC TTC CAC GCT CTG CAG TAC CAC CGC         552
Ala Ala Asp Arg Tyr Thr Thr Ile Phe His Ala Leu Gln Tyr His Arg
125                 130                 135                 140

ATC ATG ACC CCC GCA CCG TGC CCT CGT CAT CTG ACG GTC CTC TGG CGA         600
Ile Met Thr Pro Ala Pro Cys Pro Arg His Leu Thr Val Leu Trp Arg
                145                 150                 155

GGC TGC ACA GGC AGT GGC ATT ACC ATC GTG ACC TTC TCC CAT CAC GTC         648
Gly Cys Thr Gly Ser Gly Ile Thr Ile Val Thr Phe Ser His His Val
            160                 165                 170

CCC ACA GTG ATC GCC TTC ACA GCG CTG TTC CCG CTG ATG CTG GCC TTC         696
Pro Thr Val Ile Ala Phe Thr Ala Leu Phe Pro Leu Met Leu Ala Phe
        175                 180                 185

ATC CTG TGC CTC TAC GTG CAC ATG TTC CTG CTG GCC CGC TCC CAC ACC         744
Ile Leu Cys Leu Tyr Val His Met Phe Leu Leu Ala Arg Ser His Thr
    190                 195                 200
```

```
AGG AGG ACC CCC TCC CTT CCC AAA GCC AAC ATG AGA GGG GCC GTC ACA      792
Arg Arg Thr Pro Ser Leu Pro Lys Ala Asn Met Arg Gly Ala Val Thr
205             210                 215                 220

CTG ACT GTC CTG CTC GGG GTC TTC ATT TTC TGT TGG GCA CCC TTT GTC      840
Leu Thr Val Leu Leu Gly Val Phe Ile Phe Cys Trp Ala Pro Phe Val
                225                 230                 235

CTT CAT GTC CTC TTG ATG ACA TTC TGC CCA GCT GAC CCC TAC TGT GCC      888
Leu His Val Leu Leu Met Thr Phe Cys Pro Ala Asp Pro Tyr Cys Ala
                240                 245                 250

TGC TAC ATG TCC CTC TTC CAG GTG AAT GGT GTG TTG ATC ATG TGT AAT      936
Cys Tyr Met Ser Leu Phe Gln Val Asn Gly Val Leu Ile Met Cys Asn
            255                 260                 265

GCC ATC ATC GAC CCC TTC ATA TAT GCC TTT CGG AGC CCA GAG CTC AGG      984
Ala Ile Ile Asp Pro Phe Ile Tyr Ala Phe Arg Ser Pro Glu Leu Arg
270                 275                 280

GTC GCA TTC AAA AAG ATG GTT ATC TGC AAC TGT TAC CAG TAG             1026
Val Ala Phe Lys Lys Met Val Ile Cys Asn Cys Tyr Gln *
285                 290                 295

AATGATTGGT CCCTGATTTT AGGAGCCACA GGGATATACT GTCAGGGACA GAGTAGCGTG   1086

ACAGACCAAC AACACTAGGA CT                                           1108

(2) INFORMATION FOR SEQ ID NO: 10:

(i) SEQUENCE CHARACTERISTICS:
        (A) LENGTH: 297 amino acids
        (B) TYPE: amino acid
        (D) TOPOLOGY: linear (ii) MOLECULE TYPE: protein (xi) SEQUENCE DESCRIPTION: SEQ ID NO: 10:

Met Lys His Ile Leu Asn Leu Tyr Glu Asn Leu Asn Ser Thr Ala Arg
 1               5                  10                  15

Asn Asn Ser Asp Cys Pro Ala Val Ile Leu Pro Glu Glu Ile Phe Phe
                20                  25                  30

Thr Val Ser Ile Val Gly Val Leu Glu Asn Leu Met Val Leu Leu Ala
            35                  40                  45

Val Ala Lys Asn Lys Met Leu Gln Ser Pro Met Tyr Phe Phe Ile Cys
 50                  55                  60

Ser Leu Ala Ile Ser Asp Met Leu Gly Ser Met Tyr Lys Ile Leu Glu
65                  70                  75                  80

Asn Val Leu Ile Met Phe Lys Asn Met Gly Tyr Leu Glu Pro Arg Gly
                85                  90                  95

Ser Phe Glu Ser Thr Ala Asp Asp Val Val Asp Ser Leu Phe Ile Leu
                100                 105                 110

Ser Leu Leu Gly Ser Ile Cys Ser Leu Ser Val Ile Ala Ala Asp Arg
            115                 120                 125

Tyr Thr Thr Ile Phe His Ala Leu Gln Tyr His Arg Ile Met Thr Pro
130                 135                 140

Ala Pro Cys Pro Arg His Leu Thr Val Leu Trp Arg Gly Cys Thr Gly
145                 150                 155                 160

Ser Gly Ile Thr Ile Val Thr Phe Ser His His Val Pro Thr Val Ile
                165                 170                 175

Ala Phe Thr Ala Leu Phe Pro Leu Met Leu Ala Phe Ile Leu Cys Leu
            180                 185                 190

Tyr Val His Met Phe Leu Leu Ala Arg Ser His Thr Arg Arg Thr Pro
        195                 200                 205
```

```
Ser Leu Pro Lys Ala Asn Met Arg Gly Ala Val Thr Leu Thr Val Leu
    210                 215                 220

Leu Gly Val Phe Ile Phe Cys Trp Ala Pro Phe Val Leu His Val Leu
225                 230                 235                 240

Leu Met Thr Phe Cys Pro Ala Asp Pro Tyr Cys Ala Cys Tyr Met Ser
                245                 250                 255

Leu Phe Gln Val Asn Gly Val Leu Ile Met Cys Asn Ala Ile Ile Asp
            260                 265                 270

Pro Phe Ile Tyr Ala Phe Arg Ser Pro Glu Leu Arg Val Ala Phe Lys
        275                 280                 285

Lys Met Val Ile Cys Asn Cys Tyr Gln
    290                 295
```

(2) INFORMATION FOR SEQ ID NO: 11:

(i) SEQUENCE CHARACTERISTICS:
        (A) LENGTH: 1338 base pairs
        (B) TYPE: nucleic acid
        (C) STRANDEDNESS: single
        (D) TOPOLOGY: linear (ii) MOLECULE TYPE: cDNA to mRNA (ix) FEATURE:
        (A) NAME/KEY: 5'UTR
        (B) LOCATION: 1..297

(ix) FEATURE:
        (A) NAME/KEY: CDS
        (B) LOCATION: 298..1269

(ix) FEATURE:
        (A) NAME/KEY: 3'UTR
        (B) LOCATION: 1270..1338

(xi) SEQUENCE DESCRIPTION: SEQ ID NO: 11:

```
GGCTGTAACT GTAGCAACCG GTGTTGGGTG GGGATGAGAA GAGACCAGAG AGAGAGAGGG      60

TCAGAGCGAC AGGGGATGAG ACAGGCTGGT CAGAGTCTGC ACTGATTGTT GGAGACGCAA     120

AGGAAAGTTT TTTCTATGTC TCCAACCTCC CCCTCCTCCC CCGTTTCTCT CTGGAGAAAC     180

TAAAATGTAG ACTGGACAGC ATCCACAAGA GAAGCACCTA GAAGAAGATT TTTTTTTCCC     240

AGCAGCTTGC TCAGGACCCT GCAGGAGCTG CAGCCGGAAC TGGTCCCGCC GATAACC       297

ATG AAC TCT TCC TGC TGC CCG TCC TCC TCT TAT CCG ACG CTG CCT AAC       345
Met Asn Ser Ser Cys Cys Pro Ser Ser Ser Tyr Pro Thr Leu Pro Asn
  1               5                   10                  15

CTC TCC CAG CAC CCT GCA GCC CCC TCT GCC AGC AAC CGG AGT GGC AGT       393
Leu Ser Gln His Pro Ala Ala Pro Ser Ala Ser Asn Arg Ser Gly Ser
              20                  25                  30

GGG TTC TGC GAG CAG GTT TTC ATC AAG CCA GAG GTC TTC CTG GCA CTG       441
Gly Phe Cys Glu Gln Val Phe Ile Lys Pro Glu Val Phe Leu Ala Leu
          35                  40                  45

GGC ATC GTC AGT CTG ATG GAA AAC ATC CTG GTG ATC CTG GCT GTG GTG       489
Gly Ile Val Ser Leu Met Glu Asn Ile Leu Val Ile Leu Ala Val Val
     50                  55                  60

AGG AAC GGC AAC CTG CAC TCC CCC ATG TAC TTC TTC CTG CTG AGC CTG       537
Arg Asn Gly Asn Leu His Ser Pro Met Tyr Phe Phe Leu Leu Ser Leu
 65                  70                  75                  80

CTG CAG GCC GAC CTG CTG GTG AGC CTG TCC AAC TCC CTG GAG ACC ATC       585
Leu Gln Ala Asp Leu Leu Val Ser Leu Ser Asn Ser Leu Glu Thr Ile
                 85                  90                  95

ATG ATC GTG GTT ATC AAC AGC GAC TCC CTG ACC TTG GAG GAC CAA TTC       633
```

```
Met Ile Val Val Ile Asn Ser Asp Ser Leu Thr Leu Glu Asp Gln Phe
            100                 105                 110

ATC CAG CAC ATG GAC AAC ATC TTC GAC TCT ATG ATC TGC ATC TCC CTG        681
Ile Gln His Met Asp Asn Ile Phe Asp Ser Met Ile Cys Ile Ser Leu
        115                 120                 125

GTG GCC TCC ATC TGC AAC CTC CTG GCC ATC GCC GTG GAC AGG TAC GTC        729
Val Ala Ser Ile Cys Asn Leu Leu Ala Ile Ala Val Asp Arg Tyr Val
    130                 135                 140

ACC ATC TTC TAT GCC CTC CGT TAC CAC AGC ATC ATG ACG GTT AGG AAA        777
Thr Ile Phe Tyr Ala Leu Arg Tyr His Ser Ile Met Thr Val Arg Lys
145                 150                 155                 160

GCC CTC TCC TTG ATC GTG GCC ATC TGG GTC TGC TGT GGC ATC TGC GGC        825
Ala Leu Ser Leu Ile Val Ala Ile Trp Val Cys Cys Gly Ile Cys Gly
                165                 170                 175

GTG ATG TTC ATC GTC TAC TCC GAG AGC AAG ATG GTC ATC GTG TGC CTC        873
Val Met Phe Ile Val Tyr Ser Glu Ser Lys Met Val Ile Val Cys Leu
            180                 185                 190

ATC ACC ATG TTC TTC GCC ATG GTG CTC CTC ATG GGC ACC CTG TAC ATC        921
Ile Thr Met Phe Phe Ala Met Val Leu Leu Met Gly Thr Leu Tyr Ile
        195                 200                 205

CAC ATG TTC CTC TTC GCC AGG CTG CAC GTC CAG CGC ATC GCG GCA CTG        969
His Met Phe Leu Phe Ala Arg Leu His Val Gln Arg Ile Ala Ala Leu
    210                 215                 220

CCA CCT GCT GAC GGG CTA GCC CCG CAG CAG CAC TCG TGC ATG AAG GGG       1017
Pro Pro Ala Asp Gly Leu Ala Pro Gln Gln His Ser Cys Met Lys Gly
225                 230                 235                 240

GCC GTC ACC ATC ACC ATC CTG CTG GGG GTT TTC ATC TTC TGC TGG GCG       1065
Ala Val Thr Ile Thr Ile Leu Leu Gly Val Phe Ile Phe Cys Trp Ala
                245                 250                 255

CCT TTC TTC CTC CAC CTG GTC CTC ATC ATC ACC TGC CCC ACC AAC CCC       1113
Pro Phe Phe Leu His Leu Val Leu Ile Ile Thr Cys Pro Thr Asn Pro
            260                 265                 270

TAC TGC ATC TGC TAC ACG GCG CAC TTC AAC ACC TAC CTG GTT CTC ATC       1161
Tyr Cys Ile Cys Tyr Thr Ala His Phe Asn Thr Tyr Leu Val Leu Ile
        275                 280                 285

ATG TGC AAC TCT GTC ATC GAC CCC CTC ATC TAC GCC TTC CGC AGC CTG       1209
Met Cys Asn Ser Val Ile Asp Pro Leu Ile Tyr Ala Phe Arg Ser Leu
    290                 295                 300

GAG CTG CGA AAC ACC TTC AAG GAG ATT CTC TGC GGT TGC AAT GGC ATG       1257
Glu Leu Arg Asn Thr Phe Lys Glu Ile Leu Cys Gly Cys Asn Gly Met
305                 310                 315                 320

AAC GTG GGC TAG GAACCCCCGA GGAGGTGTTC CACGGCTAGC AAGAGAGAA            1309
Asn Val Gly *

AAGCAATGCT CAGGTGAGAC ACAGAAGGG                                       1338

(2) INFORMATION FOR SEQ ID NO: 12:

(i) SEQUENCE CHARACTERISTICS:
        (A) LENGTH: 323 amino acids
        (B) TYPE: amino acid
        (D) TOPOLOGY: linear (ii) MOLECULE TYPE: protein (xi) SEQUENCE DESCRIPTION: SEQ ID NO: 12:

Met Asn Ser Ser Cys Cys Pro Ser Ser Tyr Pro Thr Leu Pro Asn
 1               5                   10                  15

Leu Ser Gln His Pro Ala Ala Pro Ser Ala Ser Asn Arg Ser Gly Ser
            20                  25                  30

Gly Phe Cys Glu Gln Val Phe Ile Lys Pro Glu Val Phe Leu Ala Leu
```

|       |       |       | 35    |       |       |       | 40    |       |       |       | 45    |       |       |
|-------|-------|-------|-------|-------|-------|-------|-------|-------|-------|-------|-------|-------|-------|

Gly Ile Val Ser Leu Met Glu Asn Ile Leu Val Ile Leu Ala Val Val
                50                      55                      60

Arg Asn Gly Asn Leu His Ser Pro Met Tyr Phe Leu Leu Ser Leu
 65              70                  75                      80

Leu Gln Ala Asp Leu Leu Val Ser Leu Ser Asn Ser Leu Glu Thr Ile
                85                      90                      95

Met Ile Val Val Ile Asn Ser Asp Ser Leu Thr Leu Glu Asp Gln Phe
                100                     105                     110

Ile Gln His Met Asp Asn Ile Phe Asp Ser Met Ile Cys Ile Ser Leu
            115                     120                     125

Val Ala Ser Ile Cys Asn Leu Leu Ala Ile Ala Val Asp Arg Tyr Val
            130                     135                     140

Thr Ile Phe Tyr Ala Leu Arg Tyr His Ser Ile Met Thr Val Arg Lys
145                     150                     155                     160

Ala Leu Ser Leu Ile Val Ala Ile Trp Val Cys Cys Gly Ile Cys Gly
                165                     170                     175

Val Met Phe Ile Val Tyr Ser Glu Ser Lys Met Val Ile Val Cys Leu
                180                     185                     190

Ile Thr Met Phe Phe Ala Met Val Leu Leu Met Gly Thr Leu Tyr Ile
            195                     200                     205

His Met Phe Leu Phe Ala Arg Leu His Val Gln Arg Ile Ala Ala Leu
            210                     215                     220

Pro Pro Ala Asp Gly Leu Ala Pro Gln Gln His Ser Cys Met Lys Gly
225                     230                     235                     240

Ala Val Thr Ile Thr Ile Leu Leu Gly Val Phe Ile Phe Cys Trp Ala
                245                     250                     255

Pro Phe Phe Leu His Leu Val Leu Ile Ile Thr Cys Pro Thr Asn Pro
                260                     265                     270

Tyr Cys Ile Cys Tyr Thr Ala His Phe Asn Thr Tyr Leu Val Leu Ile
            275                     280                     285

Met Cys Asn Ser Val Ile Asp Pro Leu Ile Tyr Ala Phe Arg Ser Leu
            290                     295                     300

Glu Leu Arg Asn Thr Phe Lys Glu Ile Leu Cys Gly Cys Asn Gly Met
305                     310                     315                     320

Asn Val Gly (2) INFORMATION FOR SEQ ID NO: 13:

(i) SEQUENCE CHARACTERISTICS:
    (A) LENGTH: 30 base pairs
    (B) TYPE: nucleic acid
    (C) STRANDEDNESS: single
    (D) TOPOLOGY: linear (ii) MOLECULE TYPE: DNA (genomic)

(ix) FEATURE:
    (A) NAME/KEY: misc_feature
    (B) LOCATION: 1..30
    (D) OTHER INFORMATION: /function = "Degenerate
      oligonucleotide primer (sense)"

(xi) SEQUENCE DESCRIPTION: SEQ ID NO: 13:

GAGTCGACCR CCCATGTAYT DYTTCATCTG                 30

(2) INFORMATION FOR SEQ ID NO: 14:

-continued

```
    (i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..30
        (D) OTHER INFORMATION: /function = "Degenerate
            oligonucleotide primer (sense)"

(xi) SEQUENCE DESCRIPTION: SEQ ID NO: 14:

CAGAATTCGG AARGCRTAKA TGARGGGGTC                                         30

(2) INFORMATION FOR SEQ ID NO: 15:

(i) SEQUENCE CHARACTERISTICS:
        (A) LENGTH: 1671 base pairs
        (B) TYPE: nucleic acid
        (C) STRANDEDNESS: single
        (D) TOPOLOGY: linear (ii) MOLECULE TYPE: cDNA to mRNA (ix) FEATURE:
        (A) NAME/KEY: 5'UTR
        (B) LOCATION: 1..393

(ix) FEATURE:
        (A) NAME/KEY: CDS
        (B) LOCATION: 394..1389

(ix) FEATURE:
        (A) NAME/KEY: 3'UTR
        (B) LOCATION: 1390..1671

(xi) SEQUENCE DESCRIPTION: SEQ ID NO: 15:

AGCTTCCGAG AGGCAGCCGA TGTGAGCATG TGCGCACAGA TTCGTCTCCC AATGGCATGG         60

CAGCTTCAAG GAAAATTATT TTGAACAGAC TTGAATGCAT AAGATTAAAG TTAAAGCAGA        120

AGTGAGAACA AGAAAGCAAA GAGCAGACTC TTTCAACTGA GAATGAATAT TTTGAAGCCC        180

AAGATTTTAA CGTGATGATG ATTAGAGTCG TACCTAAAAG AGACTAAAAA CTCCATGTCA        240

AGCTCTGGAC TTGTGACATT TACTCACAGC AGGCATGGCA ATTTTAGCCT CACAACTTTC        300

AGACAGATAA AGACTTGGAG GAAATAACTG AGACGACTCC CTGACCCAGG AGGTTAAATC        360

AATTCAGGGG GACACTGGAA TTCTCCTGCC AGC ATG GTG AAC TCC ACC CAC CGT        414
                                    Met Val Asn Ser Thr His Arg
                                      1               5

GGG ATG CAC ACT TCT CTG CAC CTC TGG AAC CGC AGC AGT TAC AGA CTG        462
Gly Met His Thr Ser Leu His Leu Trp Asn Arg Ser Ser Tyr Arg Leu
 10                  15                  20

CAC AGC AAT GCC AGT GAG TCC CTT GGA AAA GGC TAC TCT GAT GGA GGG        510
His Ser Asn Ala Ser Glu Ser Leu Gly Lys Gly Tyr Ser Asp Gly Gly
         25                  30                  35

TGC TAC GCG CAA CTT TTT GTC TCT CCT GAG GTG TTT GTG ACT CTG GGT        558
Cys Tyr Ala Gln Leu Phe Val Ser Pro Glu Val Phe Val Thr Leu Gly
 40                  45                  50                  55

GTG ATC AGC TTG TTG GAG AAT ATC TTA GAG ATT GTG GCA ATA GCC AAG        606
Val Ile Ser Leu Leu Glu Asn Ile Leu Glu Ile Val Ala Ile Ala Lys
                 60                  65                  70

AAC AAG AAT CTG CAT TCA CCC ATG TAC TTT TTC ATC TGC AGC TTG GCT        654
Asn Lys Asn Leu His Ser Pro Met Tyr Phe Phe Ile Cys Ser Leu Ala
         75                  80                  85
```

-continued

```
GTG GCT GAT ATG CTG GTG AGC GTT TCA AAT GGA TCA GAA ACC ATT ATC        702
Val Ala Asp Met Leu Val Ser Val Ser Asn Gly Ser Glu Thr Ile Ile
        90                  95                 100

ATC ACC CTA TTA AAC CGT ACA GAT ACG GAT GCA CAG AGT TTC ACA GTG        750
Ile Thr Leu Leu Asn Arg Thr Asp Thr Asp Ala Gln Ser Phe Thr Val
    105                 110                 115

AAT ATT GAT AAT GTC ATT GAC TCG GTG ATC TGT AGC TCC TTG CTT GCA        798
Asn Ile Asp Asn Val Ile Asp Ser Val Ile Cys Ser Ser Leu Leu Ala
120                 125                 130                 135

TCC ATT TGC AGC CTG CTT TCA ATT GCA GTG GAC AGG TAC TTT ACT ATC        846
Ser Ile Cys Ser Leu Leu Ser Ile Ala Val Asp Arg Tyr Phe Thr Ile
                140                 145                 150

TTC TAT GCT CTC CAG TAC CAT AAC ATT ATG ACA GTT AAG CGG GTT GGG        894
Phe Tyr Ala Leu Gln Tyr His Asn Ile Met Thr Val Lys Arg Val Gly
            155                 160                 165

ATC AGC ATA AGT TGT ATC TGG GCA GCT TGC ACG GTT TCA GGT ATT TTG        942
Ile Ser Ile Ser Cys Ile Trp Ala Ala Cys Thr Val Ser Gly Ile Leu
        170                 175                 180

TTC ATC ATT TAC TCA GAT AGT AGT GCT GTC ATC ATC TGC CTC ATC ACC        990
Phe Ile Ile Tyr Ser Asp Ser Ser Ala Val Ile Ile Cys Leu Ile Thr
    185                 190                 195

ATG TTC TTC ACC ATG CTG GCT CTC ATG GCT TCT CTC TAT GTC CAC CTG       1038
Met Phe Phe Thr Met Leu Ala Leu Met Ala Ser Leu Tyr Val His Leu
200                 205                 210                 215

TTC CTG ATG GCC AGG CTT CAC ATT AAG AGG ATT GCT GTC CTC CCC GGC       1086
Phe Leu Met Ala Arg Leu His Ile Lys Arg Ile Ala Val Leu Pro Gly
                220                 225                 230

ACT GGT GCC ATC CGC CAA GGT GCC AAT ATG AAG GGA GCG ATT ACC TTG       1134
Thr Gly Ala Ile Arg Gln Gly Ala Asn Met Lys Gly Ala Ile Thr Leu
            235                 240                 245

ACC ATC CTG ATT GGC GTC TTT GTT GTC TGC TGG GCC CCA TTC TTC CTC       1182
Thr Ile Leu Ile Gly Val Phe Val Val Cys Trp Ala Pro Phe Phe Leu
        250                 255                 260

CAC TTA ATA TTC TAC ATC TCT TGT CCT CAG AAT CCA TAT TGT GTG TGC       1230
His Leu Ile Phe Tyr Ile Ser Cys Pro Gln Asn Pro Tyr Cys Val Cys
    265                 270                 275

TTC ATG TCT CAC TTT AAC TTG TAT CTC ATA CTG ATC ATG TGT AAT TCA       1278
Phe Met Ser His Phe Asn Leu Tyr Leu Ile Leu Ile Met Cys Asn Ser
280                 285                 290                 295

ATC ATC GAT CCT CTG ATT TAT GCA CTC CGG AGT CAA GAA CTG AGG AAA       1326
Ile Ile Asp Pro Leu Ile Tyr Ala Leu Arg Ser Gln Glu Leu Arg Lys
                300                 305                 310

ACC TTC AAA GAG ATC ATC TCT TCC TAT CCC CTG GGA GGC CTT TGT GAC       1374
Thr Phe Lys Glu Ile Ile Ser Ser Tyr Pro Leu Gly Gly Leu Cys Asp
            315                 320                 325

TTG TCT AGC AGA TAT TAAATGGGA CAGAGCACGC AATATAGGAA CATCCATAAG        1429
Leu Ser Ser Arg Tyr
        330

AGACTTTTTC ACTCTTACCC TACCTGAATA TTCTACTTCT GCAACAGCTT TCTCTTCCGT     1489

GTAGGGTACT GGTTGAGATA TCCATTGTGT AAATTTAAGC CTATGATTTT TAATGAGAAA     1549

AAATGCCCAG TCTCTGTATT ATTTCCAATC TCATGCTACT TTTTTGGCCA TAAAATATGA    1609

ATCTATGTTA TAGGTTGTAG GCACTGTGGA TTTACAAAAA GAAAAGTCCT TATTAAAAGA    1669

TT                                                                   1671
```

(2) INFORMATION FOR SEQ ID NO: 16:

(i) SEQUENCE CHARACTERISTICS:
        (A) LENGTH: 332 amino acids (B) TYPE: amino acid
        (D) TOPOLOGY: linear (ii) MOLECULE TYPE: protein (xi) SEQUENCE DESCRIPTION: SEQ ID NO: 16:

Met Val Asn Ser Thr His Arg Gly Met His Thr Ser Leu His Leu Trp
  1               5                  10                  15

Asn Arg Ser Ser Tyr Arg Leu His Ser Asn Ala Ser Glu Ser Leu Gly
                 20                  25                  30

Lys Gly Tyr Ser Asp Gly Gly Cys Tyr Ala Gln Leu Phe Val Ser Pro
             35                  40                  45

Glu Val Phe Val Thr Leu Gly Val Ile Ser Leu Leu Glu Asn Ile Leu
 50                  55                  60

Glu Ile Val Ala Ile Ala Lys Asn Lys Asn Leu His Ser Pro Met Tyr
 65                  70                  75                  80

Phe Phe Ile Cys Ser Leu Ala Val Ala Asp Met Leu Val Ser Val Ser
                 85                  90                  95

Asn Gly Ser Glu Thr Ile Ile Ile Thr Leu Leu Asn Arg Thr Asp Thr
                100                 105                 110

Asp Ala Gln Ser Phe Thr Val Asn Ile Asp Asn Val Ile Asp Ser Val
            115                 120                 125

Ile Cys Ser Ser Leu Leu Ala Ser Ile Cys Ser Leu Leu Ser Ile Ala
130                 135                 140

Val Asp Arg Tyr Phe Thr Ile Phe Tyr Ala Leu Gln Tyr His Asn Ile
145                 150                 155                 160

Met Thr Val Lys Arg Val Gly Ile Ser Ile Ser Cys Ile Trp Ala Ala
                165                 170                 175

Cys Thr Val Ser Gly Ile Leu Phe Ile Ile Tyr Ser Asp Ser Ser Ala
            180                 185                 190

Val Ile Ile Cys Leu Ile Thr Met Phe Phe Thr Met Leu Ala Leu Met
            195                 200                 205

Ala Ser Leu Tyr Val His Leu Phe Leu Met Ala Arg Leu His Ile Lys
            210                 215                 220

Arg Ile Ala Val Leu Pro Gly Thr Gly Ala Ile Arg Gln Gly Ala Asn
225                 230                 235                 240

Met Lys Gly Ala Ile Thr Leu Thr Ile Leu Ile Gly Val Phe Val Val
                245                 250                 255

Cys Trp Ala Pro Phe Phe Leu His Leu Ile Phe Tyr Ile Ser Cys Pro
            260                 265                 270

Gln Asn Pro Tyr Cys Val Cys Phe Met Ser His Phe Asn Leu Tyr Leu
            275                 280                 285

Ile Leu Ile Met Cys Asn Ser Ile Ile Asp Pro Leu Ile Tyr Ala Leu
290                 295                 300

Arg Ser Gln Glu Leu Arg Lys Thr Phe Lys Glu Ile Ile Ser Ser Tyr
305                 310                 315                 320

Pro Leu Gly Gly Leu Cys Asp Leu Ser Ser Arg Tyr
                325                 330

(2) INFORMATION FOR SEQ ID NO: 17:

(i) SEQUENCE CHARACTERISTICS:
        (A) LENGTH: 978 base pairs
        (B) TYPE: nucleic acid
        (C) STRANDEDNESS: single
        (D) TOPOLOGY: linear (ii) MOLECULE TYPE: DNA (genomic)

(ix) FEATURE:
   (A) NAME/KEY: CDS
   (B) LOCATION: 1..975

(xi) SEQUENCE DESCRIPTION: SEQ ID NO: 17:

```
ATG AAC TCC TCC TCC ACC CTG ACT GTA TTG AAT CTT ACC CTG AAC GCC        48
Met Asn Ser Ser Ser Thr Leu Thr Val Leu Asn Leu Thr Leu Asn Ala
 1               5                  10                  15

TCA GAG GAT GGC ATT TTA GGA TCA AAT GTC AAG AAC AAG TCT TTG GCC        96
Ser Glu Asp Gly Ile Leu Gly Ser Asn Val Lys Asn Lys Ser Leu Ala
                20                  25                  30

TGT GAA GAA ATG GGC ATT GCC GTG GAG GTG TTC CTG ACC CTG GGT CTC       144
Cys Glu Glu Met Gly Ile Ala Val Glu Val Phe Leu Thr Leu Gly Leu
        35                  40                  45

GTC AGC CTC TTA GAG AAC ATC CTG GTC ATT GGG GCC ATA GTA AAG AAC       192
Val Ser Leu Leu Glu Asn Ile Leu Val Ile Gly Ala Ile Val Lys Asn
50                  55                  60

AAA AAC CTG CAC TCA CCC ATG TAC TTC TTT GTG GGC AGC TTA GCC GTG       240
Lys Asn Leu His Ser Pro Met Tyr Phe Phe Val Gly Ser Leu Ala Val
65                  70                  75                  80

GCC GAC ATG CTG GTG AGC ATG TCC AAT GCC TGG GAG ACT GTC ACC ATA       288
Ala Asp Met Leu Val Ser Met Ser Asn Ala Trp Glu Thr Val Thr Ile
                85                  90                  95

TAC TTG CTA AAT AAT AAA CAC CTG GTG ATA GCC GAC ACC TTT GTG CGA       336
Tyr Leu Leu Asn Asn Lys His Leu Val Ile Ala Asp Thr Phe Val Arg
            100                 105                 110

CAC ATC GAC AAC GTG TTC GAC TCC ATG ATC TGC ATC TCT GTG GTG GCC       384
His Ile Asp Asn Val Phe Asp Ser Met Ile Cys Ile Ser Val Val Ala
        115                 120                 125

TCG ATG TGC AGT TTG CTG GCC ATT GCG GTG GAT AGG TAC ATC ACC ATC       432
Ser Met Cys Ser Leu Leu Ala Ile Ala Val Asp Arg Tyr Ile Thr Ile
130                 135                 140

TTC TAT GCC TTG CGC TAC CAC CAC ATC ATG ACC GCG AGG CGC TCG GGG       480
Phe Tyr Ala Leu Arg Tyr His His Ile Met Thr Ala Arg Arg Ser Gly
145                 150                 155                 160

GTG ATC ATC GCC TGC ATT TGG ACC TTC TGC ATA AGC TGC GGC ATT GTT       528
Val Ile Ile Ala Cys Ile Trp Thr Phe Cys Ile Ser Cys Gly Ile Val
                165                 170                 175

TTC ATC ATC TAC TAT GAG TCC AAG TAT GTG ATC ATT TGC CTC ATC TCC       576
Phe Ile Ile Tyr Tyr Glu Ser Lys Tyr Val Ile Ile Cys Leu Ile Ser
            180                 185                 190

ATG TTC TTC ACC ATG CTG TTC TTC ATG GTG TCT CTG TAT ATA CAC ATG       624
Met Phe Phe Thr Met Leu Phe Phe Met Val Ser Leu Tyr Ile His Met
        195                 200                 205

TTC CTC CTG GCC CGG AAC CAT GTC AAG CGG ATA GCA GCT TCC CCC AGA       672
Phe Leu Leu Ala Arg Asn His Val Lys Arg Ile Ala Ala Ser Pro Arg
210                 215                 220

TAC AAC TCC GTG AGG CAA AGG ACC AGC ATG AAG GGG GCT ATT ACC CTC       720
Tyr Asn Ser Val Arg Gln Arg Thr Ser Met Lys Gly Ala Ile Thr Leu
225                 230                 235                 240

ACC ATG CTA CTG GGG ATT TTC ATT GTC TGC TGG TCT CCC TTC TTT CTT       768
Thr Met Leu Leu Gly Ile Phe Ile Val Cys Trp Ser Pro Phe Phe Leu
                245                 250                 255

CAC CTT ATC TTA ATG ATC TCC TGC CCT CAG AAC GTC TAC TGC TCT TGC       816
His Leu Ile Leu Met Ile Ser Cys Pro Gln Asn Val Tyr Cys Ser Cys
            260                 265                 270

TTT ATG TCT TAC TTC AAC ATG TAC CTT ATA CTC ATC ATG TGC AAC TCC       864
Phe Met Ser Tyr Phe Asn Met Tyr Leu Ile Leu Ile Met Cys Asn Ser
        275                 280                 285
```

```
GTG ATC GAT CCT CTC ATC TAC GCC CTC CGC AGC CAA GAG ATG CGG AGG      912
Val Ile Asp Pro Leu Ile Tyr Ala Leu Arg Ser Gln Glu Met Arg Arg
    290                 295                 300

ACC TTT AAG GAG ATC GTC TGT TGT CAC GGA TTC CGG CGA CCT TGT AGG      960
Thr Phe Lys Glu Ile Val Cys Cys His Gly Phe Arg Arg Pro Cys Arg
305                 310                 315                 320

CTC CTT GGC GGG TAT TAA                                              978
Leu Leu Gly Gly Tyr
                325
```

(2) INFORMATION FOR SEQ ID NO: 18:

(i) SEQUENCE CHARACTERISTICS:
        (A) LENGTH: 325 amino acids
        (B) TYPE: amino acid
        (D) TOPOLOGY: linear (ii) MOLECULE TYPE: protein (xi) SEQUENCE DESCRIPTION: SEQ ID NO: 18:

```
Met Asn Ser Ser Thr Leu Thr Val Leu Asn Leu Thr Leu Asn Ala
 1               5                  10                  15

Ser Glu Asp Gly Ile Leu Gly Ser Asn Val Lys Asn Lys Ser Leu Ala
                20                  25                  30

Cys Glu Glu Met Gly Ile Ala Val Glu Val Phe Leu Thr Leu Gly Leu
                35                  40                  45

Val Ser Leu Leu Glu Asn Ile Leu Val Ile Gly Ala Ile Val Lys Asn
    50                  55                  60

Lys Asn Leu His Ser Pro Met Tyr Phe Phe Val Gly Ser Leu Ala Val
65                  70                  75                  80

Ala Asp Met Leu Val Ser Met Ser Asn Ala Trp Glu Thr Val Thr Ile
                85                  90                  95

Tyr Leu Leu Asn Asn Lys His Leu Val Ile Ala Asp Thr Phe Val Arg
                100                 105                 110

His Ile Asp Asn Val Phe Asp Ser Met Ile Cys Ile Ser Val Val Ala
                115                 120                 125

Ser Met Cys Ser Leu Leu Ala Ile Ala Val Asp Arg Tyr Ile Thr Ile
    130                 135                 140

Phe Tyr Ala Leu Arg Tyr His His Ile Met Thr Ala Arg Arg Ser Gly
145                 150                 155                 160

Val Ile Ile Ala Cys Ile Trp Thr Phe Cys Ile Ser Cys Gly Ile Val
                165                 170                 175

Phe Ile Ile Tyr Tyr Glu Ser Lys Tyr Val Ile Ile Cys Leu Ile Ser
                180                 185                 190

Met Phe Phe Thr Met Leu Phe Phe Met Val Ser Leu Tyr Ile His Met
                195                 200                 205

Phe Leu Leu Ala Arg Asn His Val Lys Arg Ile Ala Ala Ser Pro Arg
    210                 215                 220

Tyr Asn Ser Val Arg Gln Arg Thr Ser Met Lys Gly Ala Ile Thr Leu
225                 230                 235                 240

Thr Met Leu Leu Gly Ile Phe Ile Val Cys Trp Ser Pro Phe Leu
                245                 250                 255

His Leu Ile Leu Met Ile Ser Cys Pro Gln Asn Val Tyr Cys Ser Cys
                260                 265                 270

Phe Met Ser Tyr Phe Asn Met Tyr Leu Ile Leu Ile Met Cys Asn Ser
                275                 280                 285
```

```
Val Ile Asp Pro Leu Ile Tyr Ala Leu Arg Ser Gln Glu Met Arg Arg
    290                 295                 300

Thr Phe Lys Glu Ile Val Cys Cys His Gly Phe Arg Arg Pro Cys Arg
305                 310                 315                 320

Leu Leu Gly Gly Tyr
                325
```

(2) INFORMATION FOR SEQ ID NO: 19:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..32
        (D) OTHER INFORMATION: /function = "Degenerate
            oligonucleotide primer (antisense)"

(xi) SEQUENCE DESCRIPTION: SEQ ID NO: 19:

GAATTCGACG TCACAGTATG ACGGCCATGG                               30

(2) INFORMATION FOR SEQ ID NO: 20:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 20:

CTAGGATAGG GGAACTGTAG T                                           21

(2) INFORMATION FOR SEQ ID NO: 21:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 21:

GAGGATTGGG AAGACAATAG CA                                        22

(2) INFORMATION FOR SEQ ID NO: 22:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 22:

ATGAACTCCT CCTCCACCCT G                                            21

We claim:

1. A method of assaying a test compound for binding to a mammalian, MC-5 melanocortin receptor, the method comprising the following steps:
   (a) providing a first primary eukaryotic cell culture derived from a tissue in a mouse expressing the endogenous MC5-R melanocortin receptor;
   (b) providing a second primary eukaryotic cell culture derived from a second mouse wherein the genome of said second mouse comprises a homozygous disruption of the genetic sequence encoding the MC5-R melanocortin receptor wherein the disrupted allele cannot produce the MC5-R melanocortin receptor in the cell, wherein the second primary cell culture is derived from a tissue of the second mouse that corresponds to the tissue from which the first primary cell culture is derived;
   (c) contacting the eukaryotic cell culture of subpart (a) and the eukaryotic cell culture of subpart (b) with the test compound;
   (d) detecting binding of the test compound to the cells of the eukaryotic cell culture of subpart (a) and the eukaryotic cell culture of subpart (b);
   (e) comparing binding of the test compound to the cells of the eukaryotic cell culture of subpart (a) with binding of the test compound to cells of the eukaryotic cell culture of subpart (b); and
   (f) identifying mammalian MC5-R melanocyte receptor binding compounds as those compounds that bind to the eukaryotic cell culture of subpart (a) but do not bind to the eukaryotic cell culture of subpart (b).

2. The method of claim 1 wherein the test compound is detectably labeled.

3. The method of claim 2 wherein the test compound is detectably labeled with a radioisotope, a fluorescent label, a hapten, an enzymatic label or an antigenic label.

4. The method of claim 1 wherein binding of the test compound to the cells of the eukaryotic cell cultures of subpart (a) or subpart (b) is detected by assaying for a metabolite produced in the cells that bind the test compound.

5. The method of claim 4 wherein the metabolite is cyclic adenosine monophosphate (cAMP).

6. The method of claim 1, wherein the eukaryotic cell cultures of subpart (a) or subpart (b) further comprise a recombinant expression construct encoding a cAMP responsive element transcription factor binding site operatively linked to a nucleic acid sequence encoding a protein that produces a detectable metabolite.

7. The method of claim 6 wherein the nucleic acid sequence encodes β-galactosidase.

8. The method of claim 1, further comprising the steps of:
   (a) contacting the cells of the eukaryotic cell culture of subparts (a) and (b) with a detectably-labeled MCR-5 melanocortin receptor agonist or antagonist prior to contacting the eukaryotic cell cultures with the test compound;
   (b) comparing binding of the detectably labeled MCR-5 melanocortin agonist or antagonist in the presence and absence of the test compound for each of the eukaryotic cell cultures of subparts (a) and (b); and
   (c) comparing inhibition of binding of the detectably-labeled MCR-5 melanocortin receptor agonist or antagonist by the test compound to the cells of the eukaryotic cell culture of subpart (a) with inhibition of binding of the detectably-labeled MCR-5 melanocortin receptor agonist of antagonist by the test compound to cells of the eukaryotic cell culture of subpart (b).

9. The method of claim 8 wherein the detectably-labeled, MCR-5 melanocortin receptor agonist or antagonist is detectably labeled with a radioisotope, a fluorescent label, a hapten, an enzymatic label or an antigenic label.

10. The method of claim 8 wherein binding of the test compound to the cells of the eukaryotic cell cultures of subpart (a) or subpart (b) is detected by assaying for a metabolite produced in the cells that bind the test compound.

11. The method of claim 10 wherein the metabolite is cyclic adenosine monophosphate (cAMP).

12. The method of claim 8, wherein the eukaryotic cell cultures of subpart (a) or subpart (b) further comprise a recombinant expression construct encoding a cAMP responsive element transcription factor binding site operatively linked to a nucleic acid sequence encoding a protein that produces a detectable metabolite.

13. The method of claim 12 wherein the nucleic acid sequence encodes β-galactosidase.

* * * * *